United States Patent [19]
Waksman et al.

[11] Patent Number: 5,899,882
[45] Date of Patent: * May 4, 1999

[54] CATHETER APPARATUS FOR RADIATION TREATMENT OF A DESIRED AREA IN THE VASCULAR SYSTEM OF A PATIENT

[75] Inventors: Ron Waksman, Rockville, Md.;
Thomas D. Weldon, Gainesville, Ga.;
Raphael F. Meloul, Atlanta, Ga.;
Richard A. Hillstead, Duluth, Ga.;
Jonathan J. Rosen, Alpharetta, Ga.;
George K. Bonnoitt, Jr., Decatur, Ga.;
David S. Halpern, Alpharetta, Ga.;
Charles E. Larsen, Cumming, Ga.; Ian R. Crocker, Stone Mountain, Ga.

[73] Assignees: Novoste Corporation, Norcross;
Emory University, Atlanta, both of Ga.

[ * ] Notice: This patent issued on a continued prosecution application filed under 37 CFR 1.53(d), and is subject to the twenty year patent term provisions of 35 U.S.C. 154(a)(2).

[21] Appl. No.: 08/628,231

[22] Filed: Apr. 4, 1996

Related U.S. Application Data

[63] Continuation-in-part of application No. 08/330,327, Oct. 27, 1994, Pat. No. 5,683,345.

[51] Int. Cl.⁶ .................................................. A61M 29/00
[52] U.S. Cl. ............................... 604/96; 604/19; 604/280
[58] Field of Search .................................. 604/19, 27, 43, 604/96, 102, 264, 280; 606/192, 194

[56] References Cited

U.S. PATENT DOCUMENTS 1,406,509   2/1922   Viol .
1,786,373   12/1930  Walker .

(List continued on next page.)

FOREIGN PATENT DOCUMENTS 1197631   12/1985  Canada .

| | | |
|---|---|---|
| 0 152 124    | 8/1985  | European Pat. Off. . |
| 0 433 011    | 6/1991  | European Pat. Off. . |
| 0 448 004    | 8/1991  | European Pat. Off. . |
| 0 447 745 A2 | 9/1991  | European Pat. Off. . |
| 0 497 495    | 8/1992  | European Pat. Off. . |
| 0 593 136 A1 | 4/1994  | European Pat. Off. . |
| 0 688 580 A1 | 12/1995 | European Pat. Off. . |
| 1 065 989    | 9/1959  | Germany . |
| 1 095 963    | 12/1960 | Germany . |
| 1095963      | 12/1960 | Germany . |
| 1 466 774    | 6/1969  | Germany . |
| 3620123      | 12/1987 | Germany . |
| 3 643 893 A1 | 6/1988  | Germany . |
| 3739749 A1   | 6/1989  | Germany . |

(List continued on next page.)

OTHER PUBLICATIONS

Nicolini, F. et al., "Biology of Restenosis and Therapeutic Approach", *Endovascular Surgery*, vol. 72, No. 4, pp. 919–935 (Aug. 1922).

(List continued on next page.)

*Primary Examiner*—Corrine McDermott
*Attorney, Agent, or Firm*—Cook, McFarron & Manzo, Ltd.

[57] ABSTRACT

Apparatus and method are described for delivery of a treating element, such as a radiation source, through a catheter to a desired site in the intraluminal passageways of a patient, such as a coronary artery, for inhibiting the formation of scar tissue such as may occur in restenosis following balloon angioplasty. The apparatus includes an elongated flexible catheter tube having proximal and distal end portions, with a lumen extending therebetween, and a diameter sufficiently small for insertion in to a patient's intraluminal passageways. One or more treating elements, such as a capsule or pellet containing radioactive material, is positionable within the lumen and movable between the proximal and distal end portions under the force of liquid flowing through the lumen. A method for using such apparatus, including a method for using such apparatus simultaneously with a balloon angioplasty procedure, is disclosed.

36 Claims, 26 Drawing Sheets

U.S. PATENT DOCUMENTS

| | | |
|---|---|---|
| 2,750,517 | 6/1956 | Baum . |
| 2,830,190 | 4/1958 | Karp . |
| 2,965,761 | 12/1960 | Horvath . |
| 3,088,032 | 4/1963 | Brunton . |
| 3,145,181 | 8/1964 | Courtois et al. . |
| 3,154,501 | 10/1964 | Hertz . |
| 3,168,092 | 2/1965 | Silverman . |
| 3,324,847 | 6/1967 | Zoumboulis . |
| 3,351,049 | 11/1967 | Lawrence . |
| 3,532,888 | 10/1970 | Masefield . |
| 3,589,356 | 6/1971 | Silverman . |
| 3,600,568 | 8/1971 | Weyrauch . |
| 3,632,520 | 1/1972 | Garber . |
| 3,659,107 | 4/1972 | Selle et al. . |
| 3,669,093 | 6/1972 | Sauerwein et al. . |
| 3,674,006 | 7/1972 | Holmer . |
| 3,811,426 | 5/1974 | Culver et al. . |
| 3,872,856 | 3/1975 | Clayton . |
| 3,927,325 | 12/1975 | Hungate et al. . |
| 4,096,862 | 6/1978 | DeLuca . |
| 4,202,323 | 5/1980 | Zweig et al. . |
| 4,233,517 | 11/1980 | van't Hooft . |
| 4,250,887 | 2/1981 | Dardik et al. ............................ 604/150 |
| 4,292,960 | 10/1981 | Paglione . |
| 4,323,055 | 4/1982 | Kubiatowicz . |
| 4,385,635 | 5/1983 | Ruiz . |
| 4,434,788 | 3/1984 | Nakatsugawa . |
| 4,471,765 | 9/1984 | Strauss et al. ............................... 600/5 |
| 4,562,001 | 12/1985 | Vietzke et al. . |
| 4,578,061 | 3/1986 | Lemelson . |
| 4,584,991 | 4/1986 | Tokita et al. . |
| 4,588,395 | 5/1986 | Lemelson . |
| 4,654,171 | 3/1987 | Boncoeur et al. . |
| 4,676,258 | 6/1987 | Inokuchi et al. . |
| 4,697,575 | 10/1987 | Horowitz . |
| 4,706,652 | 11/1987 | Horowitz . |
| 4,726,916 | 2/1988 | Aubert et al. . |
| 4,733,653 | 3/1988 | Leung et al. ............................... 600/1 |
| 4,733,665 | 3/1988 | Palmaz . |
| 4,762,129 | 8/1988 | Bonzel . |
| 4,768,507 | 9/1988 | Fischell et al. . |
| 4,770,653 | 9/1988 | Shturman . |
| 4,815,449 | 3/1989 | Horowitz . |
| 4,819,618 | 4/1989 | Liprie . |
| 4,842,590 | 6/1989 | Tanabe et al. . |
| 4,851,694 | 7/1989 | Rague et al. . |
| 4,861,520 | 8/1989 | van't Hooft et al. . |
| 4,878,492 | 11/1989 | Sinofsky et al. . |
| 4,881,937 | 11/1989 | van't Hooft et al. . |
| 4,883,459 | 11/1989 | Calderon . |
| 4,897,076 | 1/1990 | Puthawala et al. . |
| 4,946,435 | 8/1990 | Suthanthiran et al. . |
| 4,955,895 | 9/1990 | Sugiyama et al. ..................... 606/194 |
| 5,019,075 | 5/1991 | Spears et al. . |
| 5,030,194 | 7/1991 | Van't Hooft . |
| 5,040,548 | 8/1991 | Yock . |
| 5,053,033 | 10/1991 | Clarke . |
| 5,059,166 | 10/1991 | Fischell et al. . |
| 5,084,001 | 1/1992 | van'Hooft et al. . |
| 5,084,002 | 1/1992 | Liprie . |
| 5,106,360 | 4/1992 | Ishiwara et al. . |
| 5,116,864 | 5/1992 | March et al. . |
| 5,120,973 | 6/1992 | Rohe et al. . |
| 5,147,282 | 9/1992 | Kan . |
| 5,183,455 | 2/1993 | Hayman et al. . |
| 5,199,939 | 4/1993 | Dake et al. . |
| 5,213,561 | 5/1993 | Weinstein et al. . |
| 5,267,960 | 12/1993 | Hayman et al. . |
| 5,282,781 | 2/1994 | Liprie . |
| 5,302,168 | 4/1994 | Hess . |
| 5,304,228 | 4/1994 | Prince . |
| 5,306,244 | 4/1994 | Shiber . |
| 5,327,885 | 7/1994 | Griffith ................................. 128/772 |
| 5,334,154 | 8/1994 | Samson et al. ......................... 604/102 |
| 5,354,257 | 10/1994 | Roubin et al. . |
| 5,354,774 | 10/1994 | Deckelbaum et al. . |
| 5,411,466 | 5/1995 | Hess . |
| 5,413,557 | 5/1995 | Solar ........................................ 604/96 |
| 5,417,653 | 5/1995 | Sahota et al. ........................... 604/606 |
| 5,472,403 | 12/1995 | Cornacchia et al. ........................ 600/4 |
| 5,474,531 | 12/1995 | Carter ....................................... 604/22 |
| 5,484,384 | 1/1996 | Fearnot . |
| 5,503,613 | 4/1996 | Weinberger . |
| 5,540,659 | 7/1996 | Teirstein ................................. 604/104 |
| 5,545,137 | 8/1996 | Rudie et al. .............................. 604/49 |
| 5,624,392 | 4/1997 | Saab ......................................... 604/43 |

FOREIGN PATENT DOCUMENTS

| | | |
|---|---|---|
| 91 02 312 U1 | 8/1992 | Germany . |
| 58-78654 | 3/1982 | Japan . |
| 279814 | 7/1975 | U.S.S.R. ................................ 128/603 |
| 793158 | 4/1958 | United Kingdom ....................... 600/8 |
| 1219604 | 1/1971 | United Kingdom . |
| 1558127 | 12/1977 | United Kingdom . |
| WO 90/03827 | 4/1990 | WIPO . |
| WO 93/04735 | 3/1993 | WIPO . |

OTHER PUBLICATIONS

Weidermann, J. et al, Abstract: "Intracoronary Irradiation Acutely Impairs Endothelial and Smooth Muscle Function as Assessed by Intravascular Ultrasound", Supplement to *Circulation*, vol. 86, No. 4, p. I–188, Abstract No. 0750 (Oct. 1992).

Herrman, J. et al., "Pharmacological Approaches to the Prevention of Restenosis Following Angioplasty", *Drugs*, 46(1): pp. 18–52 (1993).

Lange, R. et al., "Southwestern Internal Medicine Conference: Restenosis: The Achilles Heel of Coronary Angioplasty", *Amer. J. of the Medical Sciences*, vol. 306, pp. 265–273 (Oct. 1993).

Myler, R. et al., "Restenosis After Coronary Angioplasty: Pathophysiology and Therapeutic Implications (Part 1 of Two Parts)", *J. of Invasive Cardiology*, vol. 5, No. 8, pp. 278–285 (Oct. 1993).

Weidermann, J. et al, Abstract: "Intracoronary Irradiation Markedly Reduces Restenosis After Balloon Angioplasty in a Porcine Model", Supplement to *Circulation*, vol. 88, No. 4, pt.2, p. I–655, Abstract No. 3529 (Oct. 1993).

Landau, C. et al., "Percutaneous Transluminal Coronary Angioplasty", *New England J. of Med.*, vol. 3330, No. 14, pp. 981–993 (Apr. 7, 1994).

Paranandi, S., et al. "Contemporary Clincal Trials of Restenosis", *J. of Invasive Cardiology*, vol. 6, No. 4, pp. 109–123 (May 1994).

Wiedermann, et al, "Intracoronary Irradiation Markedly Reduces Restenosis After Balloon Angioplasty in a Porcine Model", *JACC* vol. 23, No. 6, pp. 1491–1498 (May 1994).

Glagov, S., "Intimal Hyperplasia, Vascular Modeling, and the Restenosis Problem", *Circulation*, vol. 89, No. 6, pp. 2888–2891 (Jun. 1994).

Melkert, R., et al., "Luminal Narrowing After Percutaneous Transluminal Coronary Angioplasty. A Multivariate Analysis of Clinical, Procedural and Lesion Related Factors Affecting Long–term Angiographic Outcome in the Park study", *J. Invasive Cardiology*, vol. 6, No. 5, pp. 160–171 (Jun. 1994).

Fishman, D., et al., Abstract: "A Randomized Comparison of Coronary–stent Placement and Balloon Angioplasty in the Treatment of Coronary Artery Disease", *New England J. of Medicine*, p. 496 (Aug. 25, 1994).

Endovascular Low–Dose Irradiation Inhibits Neointima Formation After Coronary Artery Balloon Injury in Swine—A Possible Role for Radiation Therapy in Restenosis Prevention, by Ron Waksman, MD; Keith A. Robinson PhD; Ian R. Crocker, MD; Michael B. Gravanis, MD; Gustavo D. Cipolla, DVM; Spencer B. King III, MD, *Circulation*, vol. 91, No. 5, pp. 1533–1539 (Mar. 1, 1995). Submitted for publication Oct. 3, 1994.

Endovascular Low Dose Irradiation Inhibits Neointima Formation after Coronary Aftery Balloon Injury in Swine—A Possible Role for Radiation Therapy in Restenosis Prevention, by Ron Waksman, MD; Keith A. Robinson, PhD; Ian R. Crocker, MD; Gustavo D. Cipolla, DVM; Spencer B. King III, MD. Submitted for publication Mar. 25, 1994.

Nisar Syed A.M., Feder B., "Technique of After–Loading Interstitial Implants", Syed/Feder, *Radiologia Clinica* 46:458–476 (1977).

Nisar Syed et al "Combination of External and Interstital Irradiation in the Primary Management of Breast Carcinoma", *Cancer* vol. 46, No. 6, pp. 1360–1365 (1980).

Puthawala, et al, "Temporary Iridium 192 Implant in the Management of Carcinoma of the Prostate", *Endocurietherapy/Hyperthermia Oncology* 1:25–34 (1985).

Nisar Syed, et al., "Transperineal Interstitial–Intracavitary "Syed–Neblett" Applicator in the Treatment of Carcinoma of the Uterine Cervix", *Endocurietherapy/Hyperthermia Oncology* 2:1–13 (1985).

Nisar Syed A.M., et al., "Intraluminal Irradiation in the Treatment of Esophageal Cancer", *Endocurietherapy/Hyperthermia Oncology*, 3:105–113 (1987).

Faxon, et al., "Mechanism of Angioplasty and Its Relation to Restenosis", *American Journal of Cardiology* 15:5B–9B (1987).

Borok, et al., "Rule of Ionizing Irradiation for 393 Keloids", *I.J. Radiation Oncology–Biology–Physics* 15:865–70 (1988).

Kovalic/Perez, "Radiation Therapy Following Keloidectomy: A 20–Year Experience", *I.J. Radiation Oncology–Biology–Physics* 17:77–80 (1989).

McCormick, et al., "Breast Cancer", Chpt. 25 of *Interstitial Brachytheapy* 221–226 (1990).

Dawson, "Theoretic Considerations Regarding Low–Dose Radiation Therapy for Prevention of Restenosis after Angioplasty", *The Reading Hospital & Medical Center* 18(1) 4–7 (1991).

Skin, p. 261 of the American Medical Association Family Medical Guide, Editor Kunz.

Friedman and Byers, "Effect of Iridium 192 Radiation on Thromboatherosclerotic Plaque in the Rabbit Aorta," *Arch Path*, vol. 80, Sep., 1965.

Friedman, Felton and Byers, "The Antiatherogenic Effect of Iridium 192 upon the Cholesterol–fed Rabbit," *Journal of Clinical Investigation*, vol. 43, No. 2, 1964, pp. 185–192.

Schwartz, et al., "Effect of External Beam Irradiation on Neointimal Hyperplasia After Experimental Coronary Artery Injury," American College of Cardiology, *JACC*, vol. 19, No. 5, Apr., 1992; 1106–13.

B. Steidle, "Preventive Percutaneous Radiation Therapy to Avoid Hyperplasia of the Intima after Angioplasty Combined with Stent–Implantation," *Strahlenther, Onkol*, 170 (1994), 151–154 (Nr. 3).

Wiedermann, et al., "Effects of High–Dose Intracoronary Irradiation on Vasomotor Function and Smooth Muscle Histopathology," *American Physiological Society*, 1994, pp. H125–H132.

Abbas, et al., "External Beam Irradiation Inhibits Neointimal Hyperplasia Following Balloon Angioplasty," *International Journal of Cardiology*, 44 (1994) 191–202.

Liermann, et al., "Interventional Treatment and Clinics in Combination with Prophylactic Endovascular Radiation in the Therapy of Intimal Hyperplasia," *Radiologe* (1994) 34; 524–533.

Shimotakahar and Mayberg, "Gamma Irradiation Inhibits Neointimal Hyperplasia in Rats After Arterial Injury," *Stroke*, vol. 25, No. 2, Feb., 1994, pp. 424–428.

Wiedermann, et al., "Intracoronary Irradiation Markedly Reduces Restenosis After Balloon Angioplasty in a Porcine Model," American College of Cardiology, *JACC* vol. 23, No. 6, May, 1994; 1491–8.

Fischell, et al., "Low–Dose, β–Particle Emission From 'Stent' Wire Results in Complete, Localized Inhibition of Smooth Muscle Cell Proliferation," *Basic Science Reports*, Circulation, vol. 90, No. 6, Dec., 1994, pp. 2956–2963.

Friedman, "Pathogenesis of the Spontaneous Atherosclerotic Plaque," *Archives of Pathology*, vol. 76, Sep., 1963; 94–105.

Friedman, et al., "Cortisone and Experimental Atherosclerosis," *Archives of Pathology*, vol. 77, Feb., 1964; 56–72.

Friedman, et al., "Aortic Atherosclerosis Intensification in Rabbits by Prior Endothelial Denudation," *Archives of Pathology*, vol. 79, Apr., 1965; 345–356.

1) English abstract re DE 1 095 963 to Wachsmann.

2) Hilaris, B.S. et al, *Atlas of Brachytherapy* Chapter 2, "Brachytherapy Instruments," title & cover pages, p. 28, pp. 42–43, 1988.

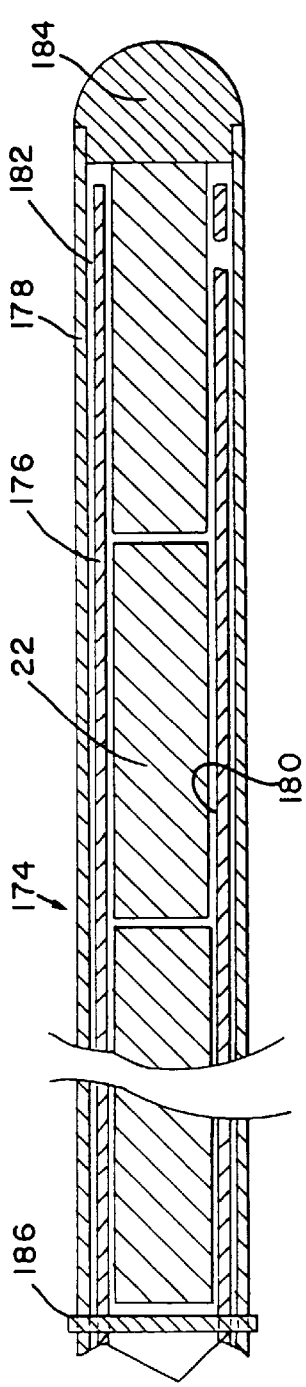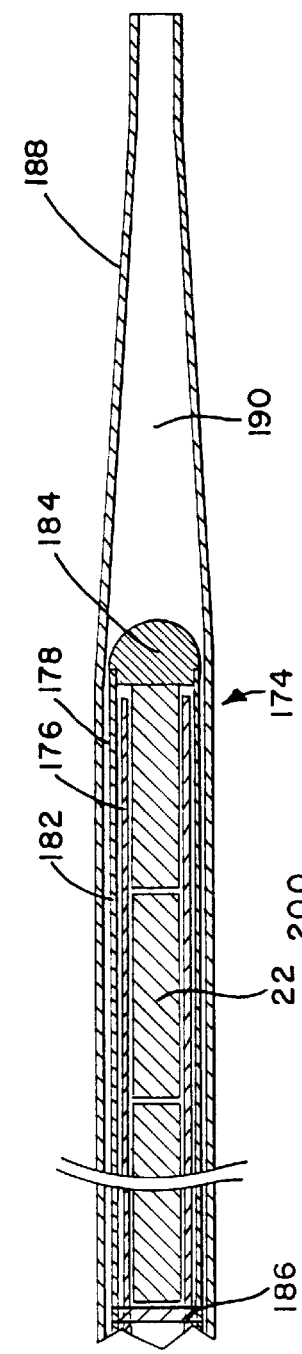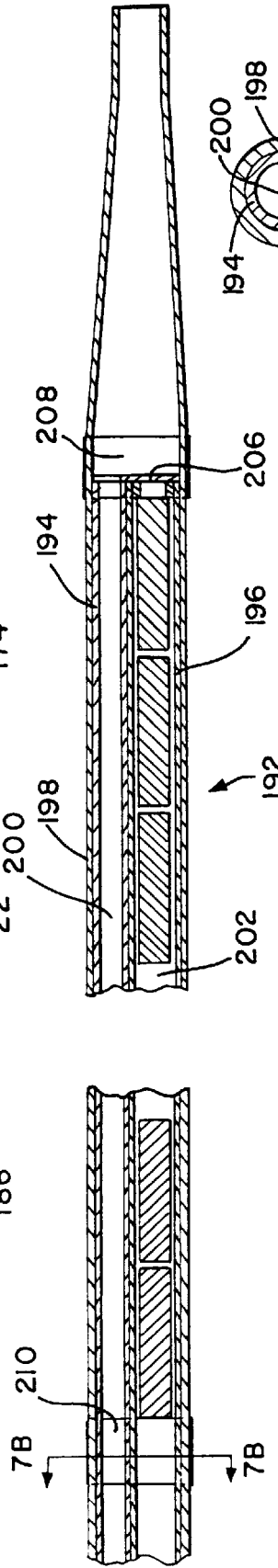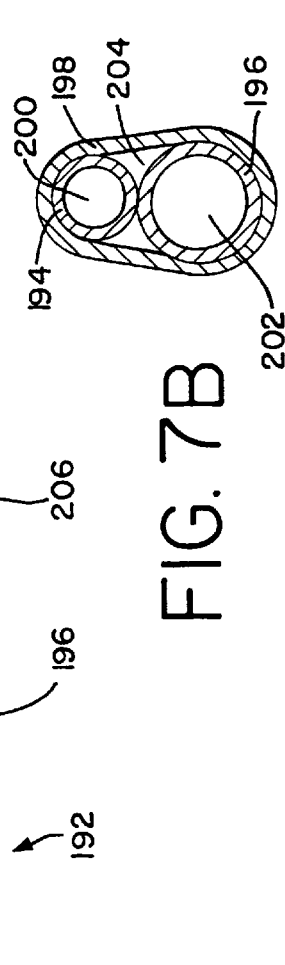

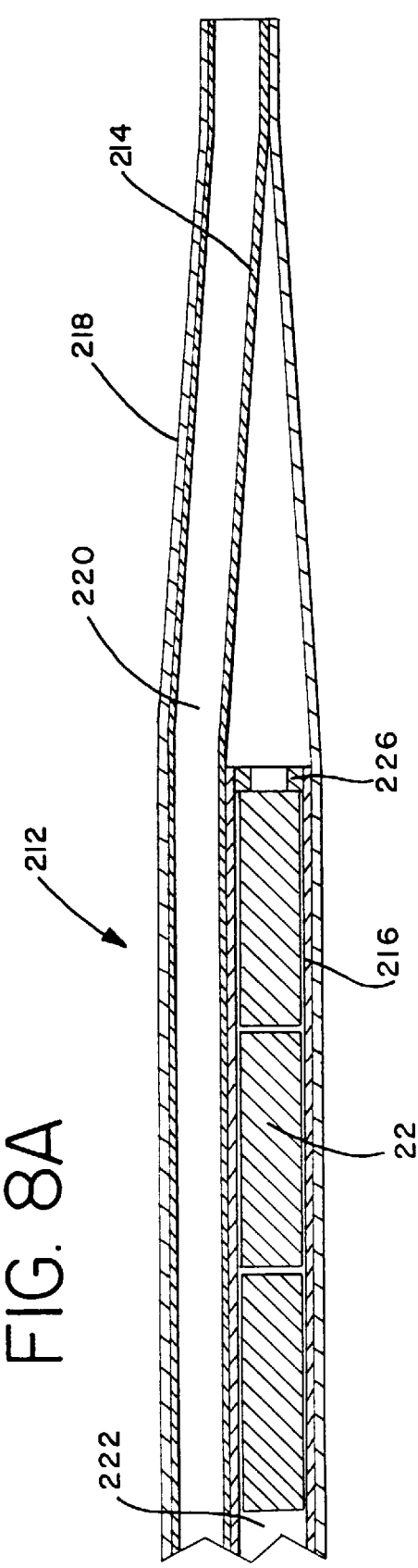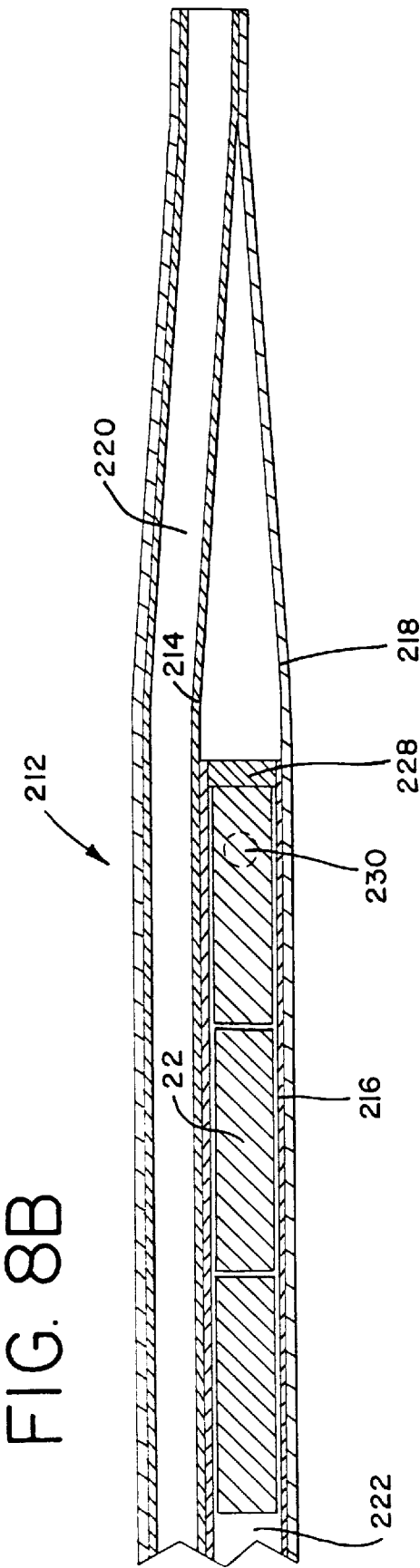

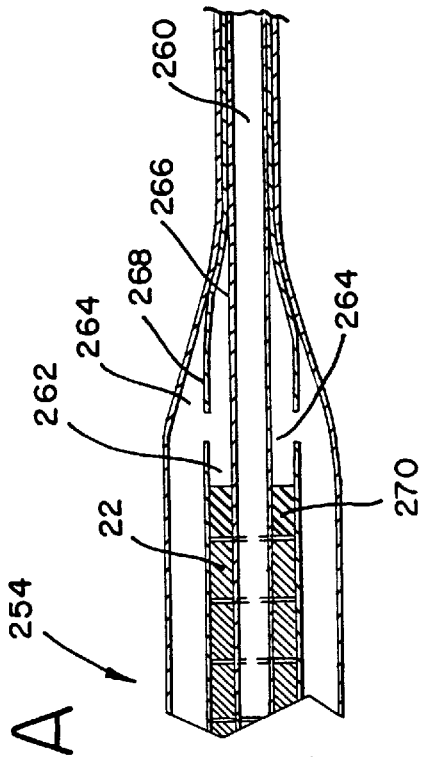
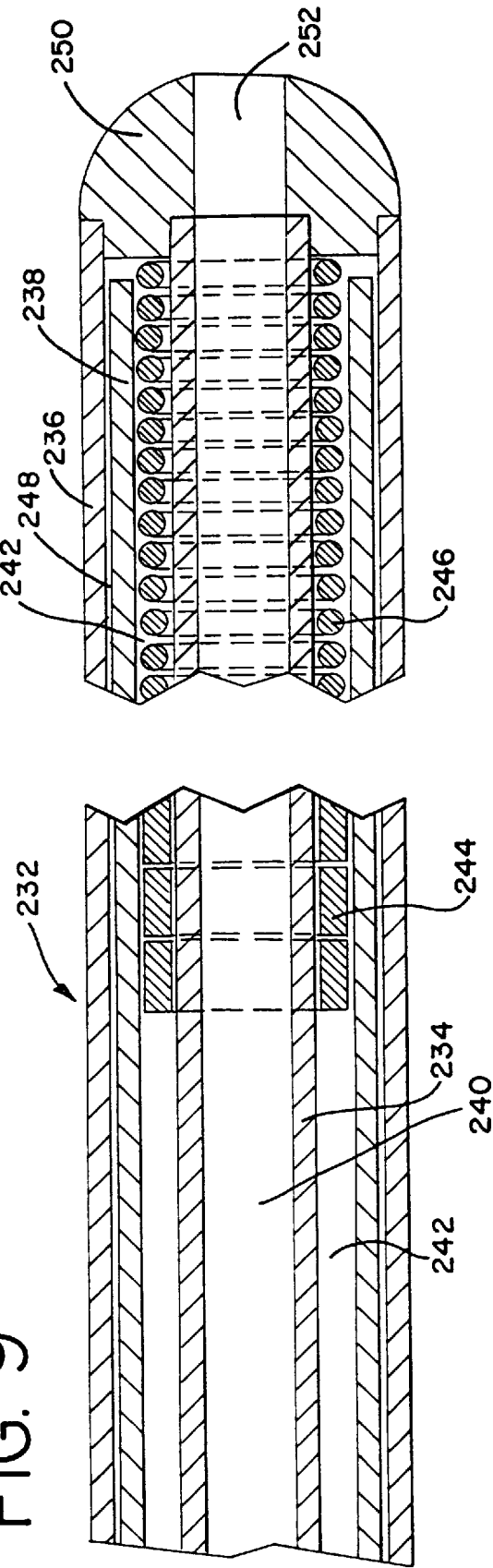
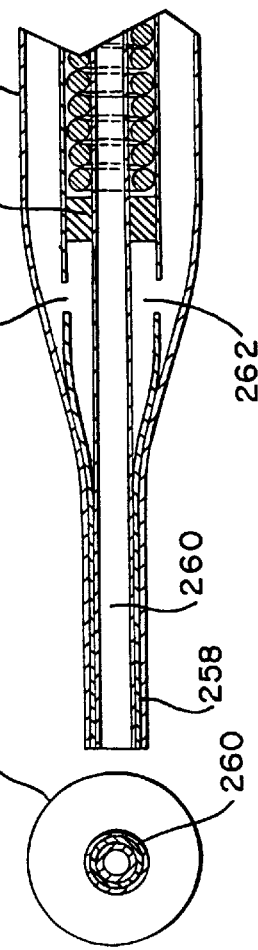
FIG. 9
FIG. 10A
FIG. 10B

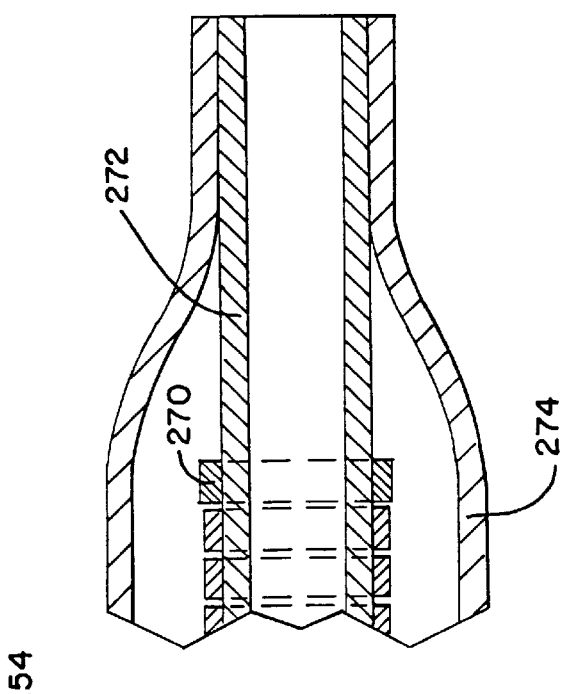
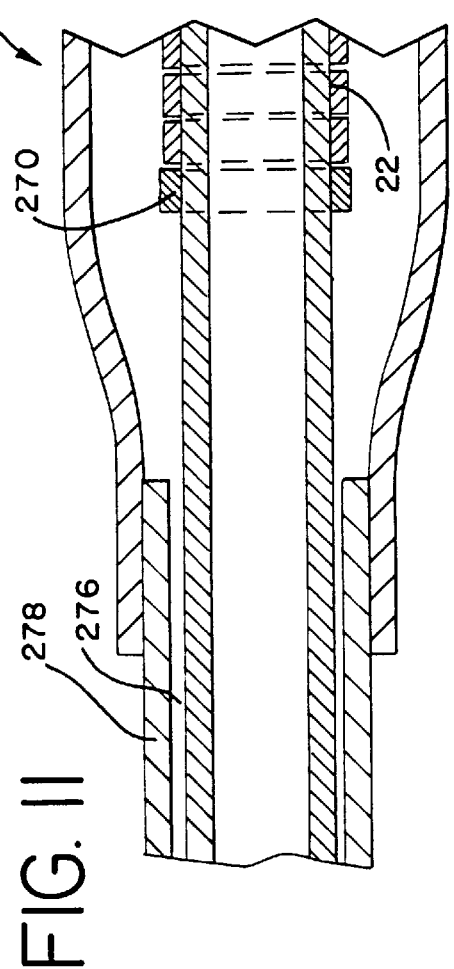
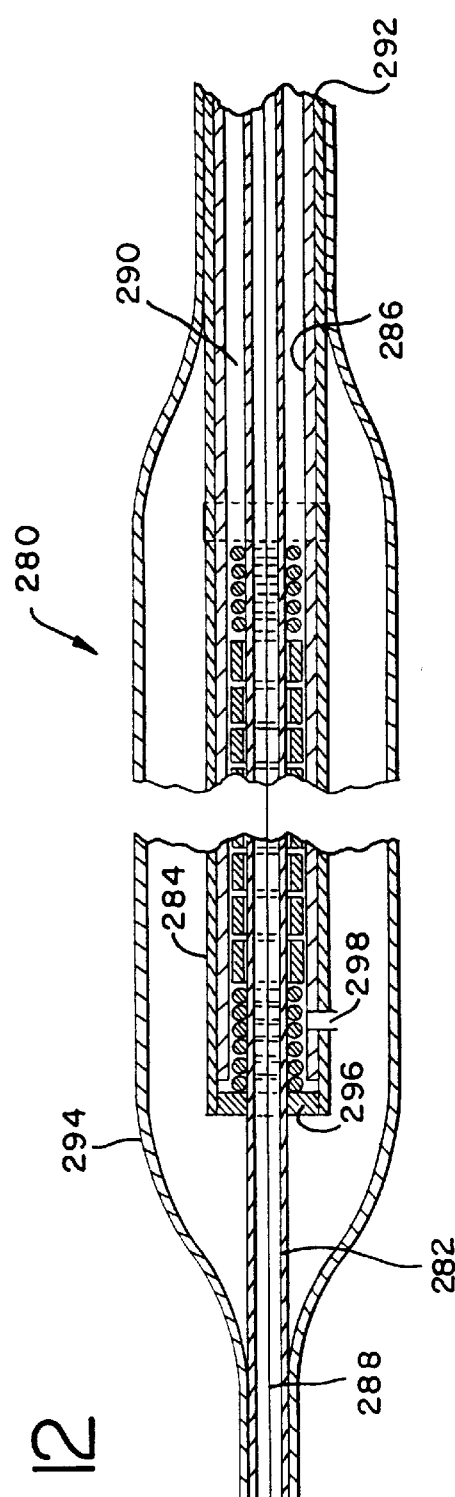
FIG. 11
FIG. 12

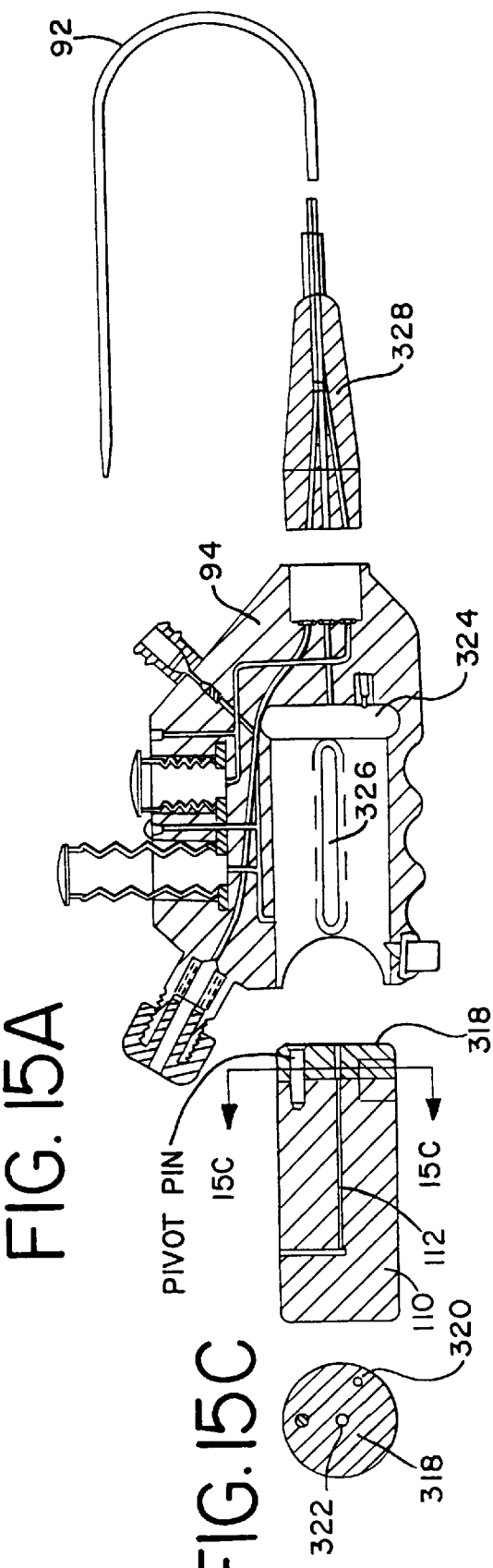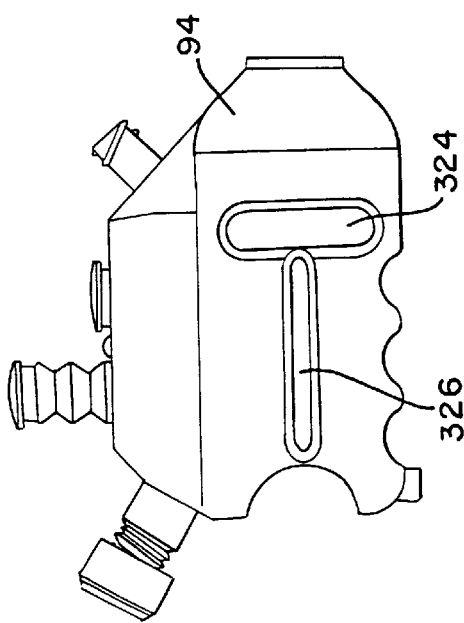

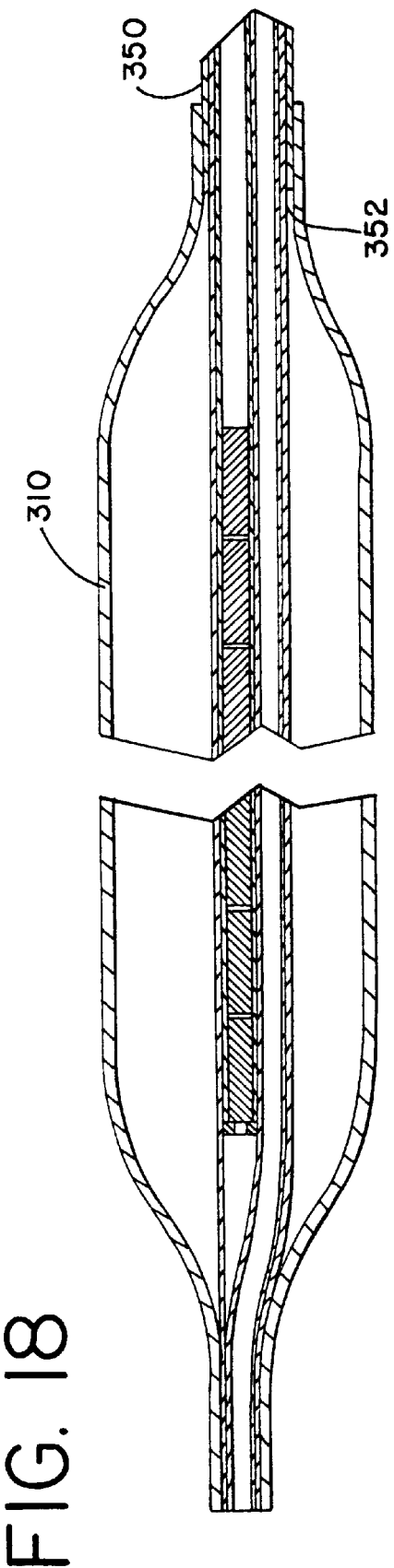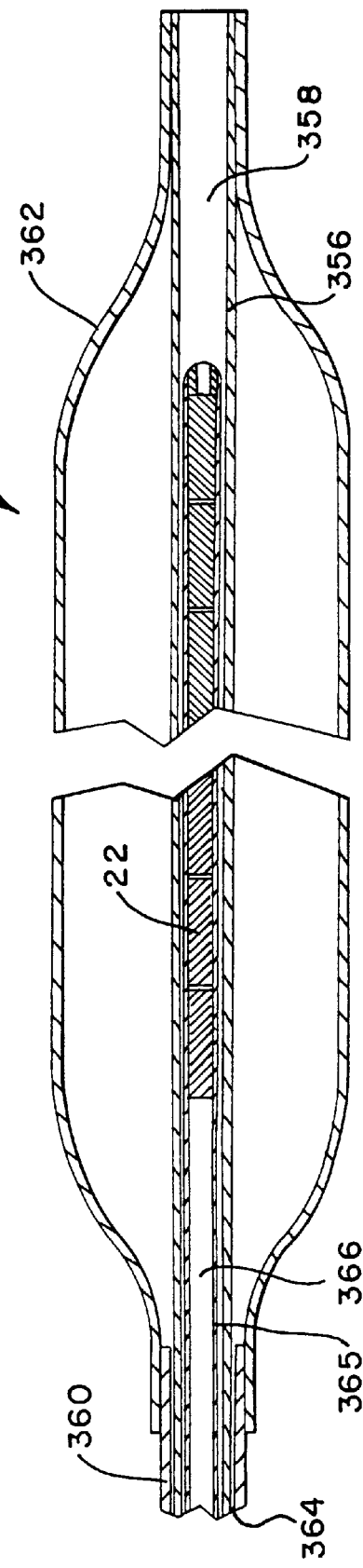

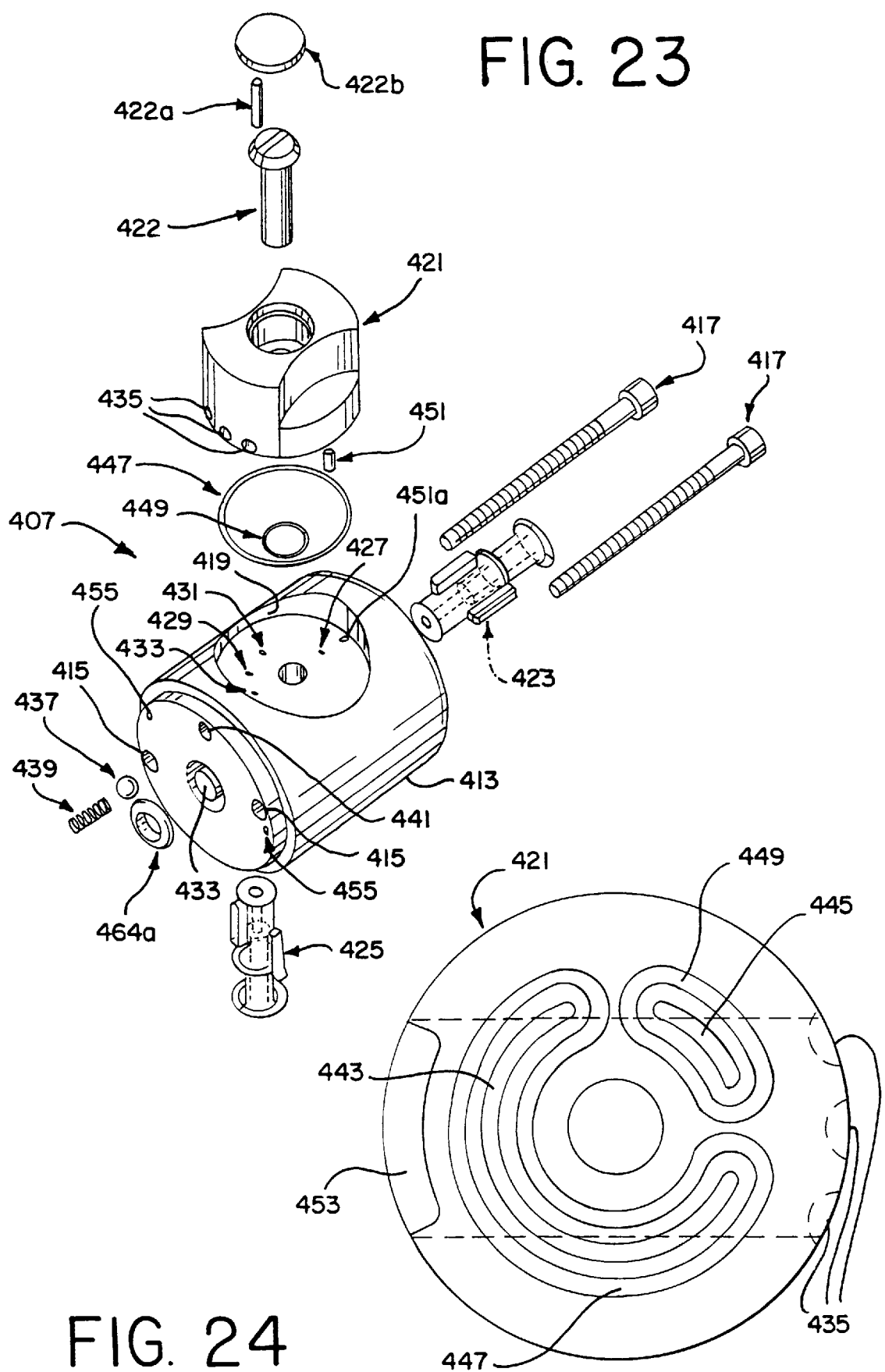

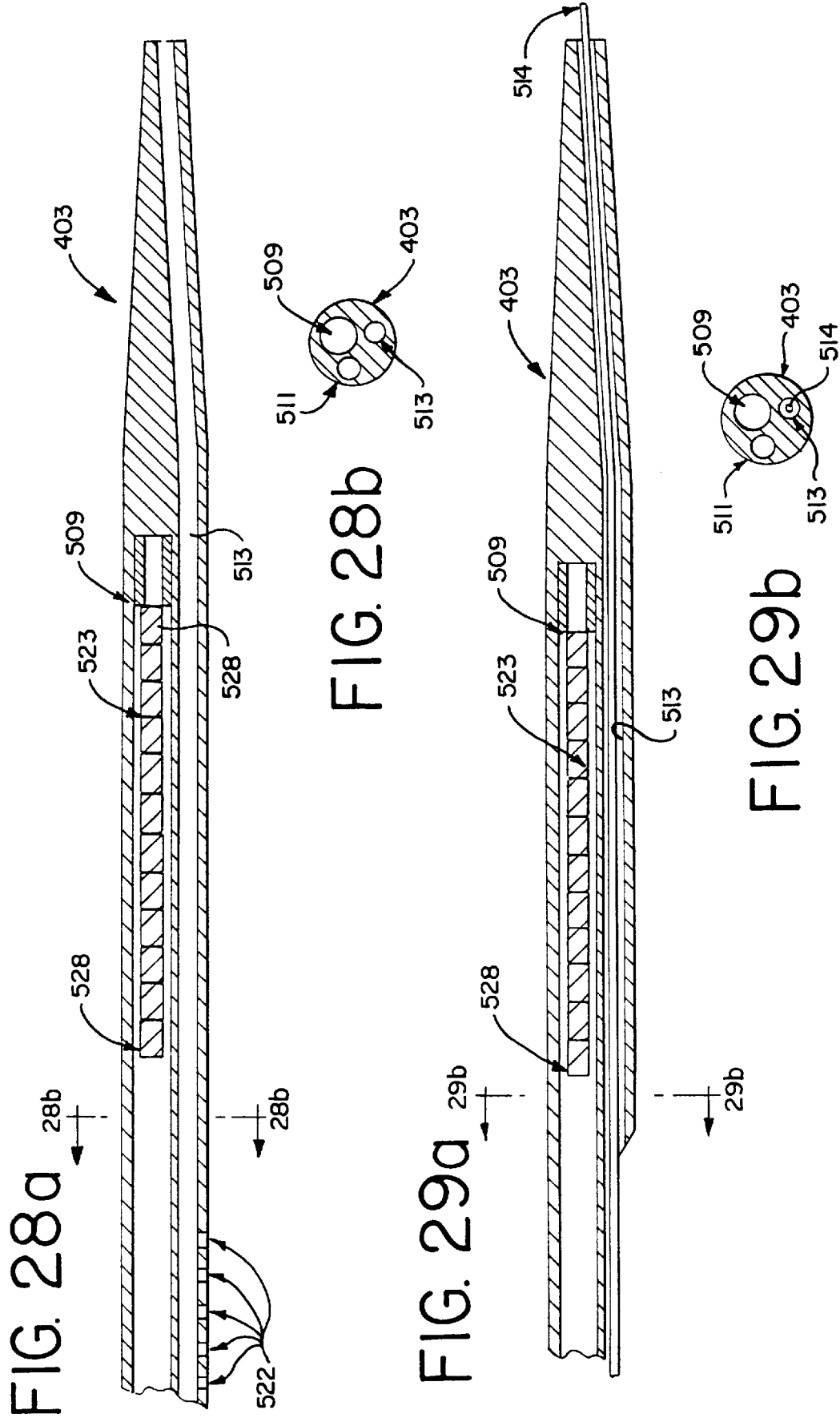

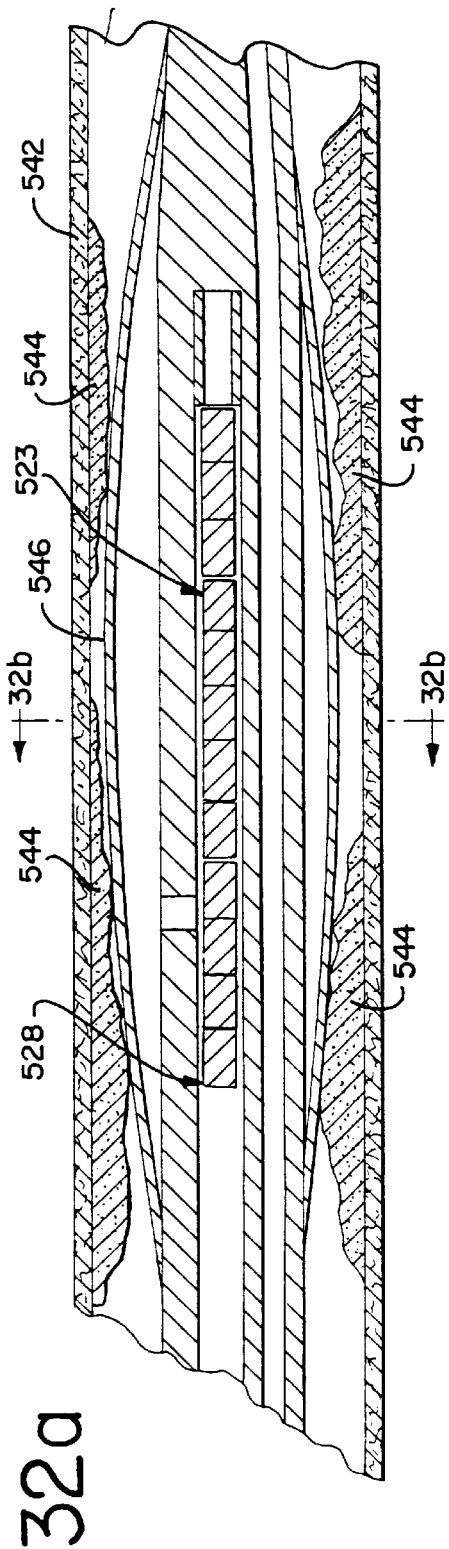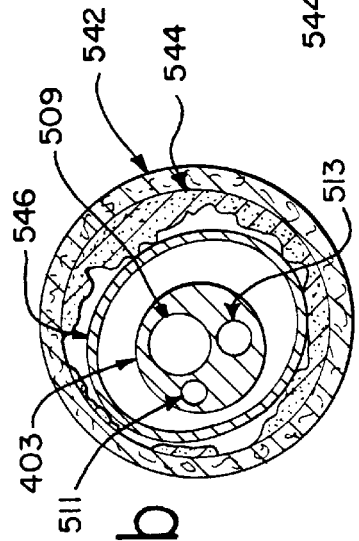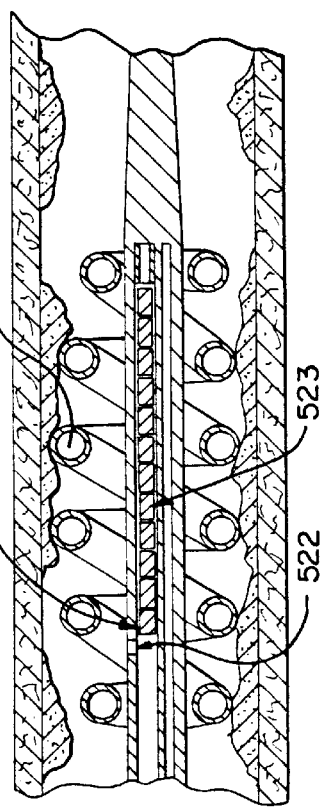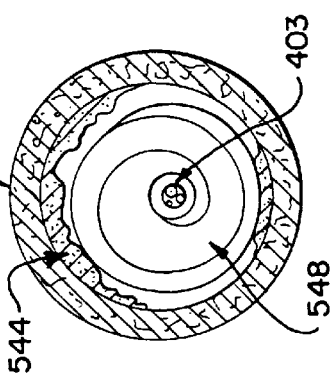
FIG. 32a
FIG. 32b
FIG. 33a
FIG. 33b

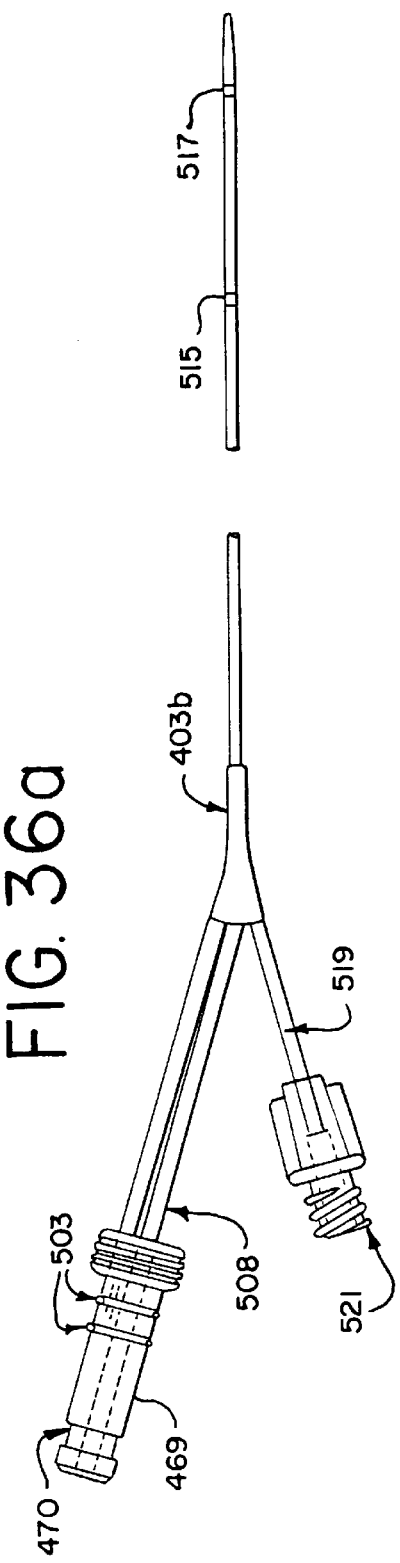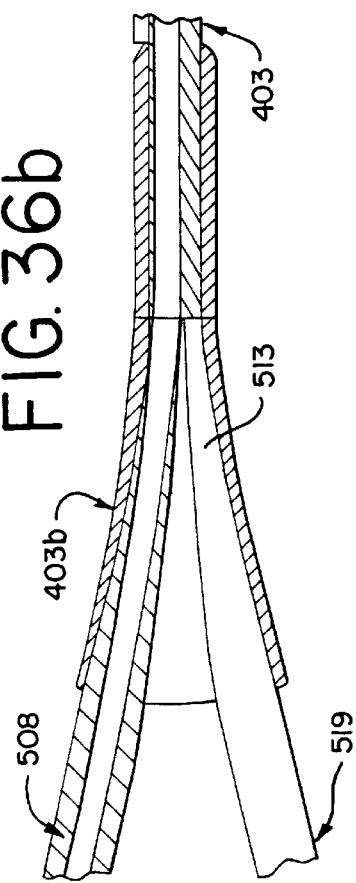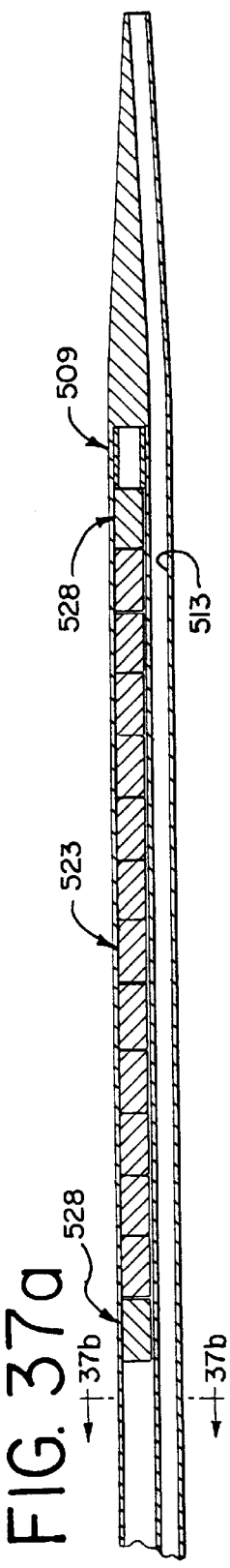

CATHETER APPARATUS FOR RADIATION TREATMENT OF A DESIRED AREA IN THE VASCULAR SYSTEM OF A PATIENT

RELATED APPLICATIONS

This application is a continuation-in-part of application Ser. No. 08/330,327 filed Oct. 27, 1994, now U.S. Pat. No. 5,683,345.

FIELD OF THE INVENTION

The present invention relates generally to the delivery of treating elements by a catheter to a selected location within the intraluminal passageways, either vascular or non-vascular, of a patient. Intraluminal passageways are defined herein as all lumens, passageways, conduits, ducts, channels, canals, vessels, and cavities within the human body. More particularly, the present invention relates to method and apparatus for the delivery of a treating element, such as a radiation source, through a catheter to a desired site, such as a coronary artery, for inhibiting wound healing response, such as restenosis following balloon angioplasty, and also for inhibiting other occurrences of cell migration, proliferation, and enlargement, including that of cancerous cells, which may not result from wound healing response.

BACKGROUND OF THE INVENTION

It is known that the human body's healing response to wounds typically includes the formation of what is commonly called scar tissues. This response also occurs within the vascular system of a person following injury to a blood vessel. An injury that provokes the formation of scar tissue may occur in various locations within the vascular system, such as in the carotid artery or in coronary bypasses, or in various ways, such as trauma from surgical or diagnostic procedures.

Just as with lumens within the vascular system, non-vascular intraluminal passageways within a human patient can experience stenosis. Procedures, such as those described below, are performed for eliminating the areas of narrowing in non-vascular body lumens, and the walls of the treated lumens most likely are injured during the process. As a result of the injury, the human body begins its healing response and an overgrowth of tissue due to increased cell proliferation renarrows the lumens.

One area of the vascular system of particular concern with respect to such injuries is coronary arteries that are subjected to procedures for removing or reducing blockages due to plaque within the arteries. Partial and even complete blockage of coronary arteries by the formation of an atherosclerotic plaque is a well known and frequent medical problem. Such blockages may be treated using atherectomy devices, which mechanically remove the plaque; hot or cold lasers, which vaporize the plaque; stents, which hold the artery open; and other devices and procedures which have the objective of allowing increased blood flow through the artery. The most common such procedure is the percutaneous transluminal coronary angioplasty (PTCA) procedures—more commonly referred to as balloon angioplasty. In this procedure, a catheter having an inflatable balloon at its distal end is introduced into the coronary artery, the uninflated balloon is positioned at the stenotic site and the balloon is inflated. Inflation of the balloon disrupts and flattens the plaque against the arterial wall, and stretches the arterial wall, resulting in enlargement of the intraluminal passageway and increased blood flow. After such expansion, the balloon is deflated and the balloon catheter removed.

PTCA is a widely used procedure and has an initial success rate of between 90 and 95 percent. However, long term success of PTCA (as well as the other artery-opening procedures referred to above) is much more limited, due largely to restenosis, or re-closing of the intraluminal passageway through the artery. Restenosis, wherein the vessel passageway narrows to approximately 50% or less of the size of the native vessel, is experienced in approximately 30 to 50 percent of the patients within six months after PTCA. Restenosis may occur for various reasons, but it is now believed that restenosis is, in significant part, a natural healing response to the vessel injury caused by inflation of the angioplasty balloon.

Vessel injury may occur in several ways during PTCA, including: denudation (stripping) of the endothelium (the layer of flat cells that line the blood vessels); cracking, splitting and/or disruption of the atherosclerotic plaque and intima (innermost lining of the blood vessel); dehiscence (bursting) of the intima and the plaque from the underlying media; stretching and tearing of the media and adventitia (outside covering of the artery) which may result in aneurysmal expansion; and injury to thr vessel smooth muscle. Such injury to the vessel typically initiates the body's own natural repair and healing process. During this healing process, fibrin and platelets rapidly accumulate in the endothelium, and vascular smooth muscle cells proliferate and migrate into the intima. The formation of scar tissue by smooth muscle proliferation, also known as intimal hyperplasia, is believed to be a major contributor to restenosis following balloon angioplasty of the coronary artery.

Prior attempts to inhibit restenosis of coronary arteries have included, among other things, the use of various light therapies, chemotherapeutic agents, stents, atherectomy devices, hot and cold lasers, as well as exposure of the stenotic site to radiation. These therapies have had varying degrees of success, and certain disadvantages are associated with each of these therapies. Although radiation therapy has shown promise, particularly in inhibiting intimal hyperplasia, the devices available for delivery of radiation sources to a stenotic site have been limited and have tended to suffer from drawbacks which limit their usefulness. Typical of the devices using radiation to treat restenosis are those shown or described in U.S. Pat. Nos. 5,059,166 to Fischell; 5,213,561 to Weinstein; 5,302,168 to Hess, 5,199, 939 to Dake; 5,084,002 to Liprie; and 3,324,847 to Zoumboulis.

SUMMARY OF THE INVENTION

The present invention is directed to apparatus and methods for delivering one or more treating elements, such as a radiation source, through a catheter to a desired location within the intraluminal passageways, either vascular or non-vascular, of a human patient and to retrieving the treating element(s) through the catheter, if so desired. The treating elements may be used to treat the intraluminal passageway through which they are delivered or may be used to treat a surrounding area of the body located within a maximum radius of the intraluminal passageway through which they are delivered. The present invention is particularly applicable, but not limited, to the treatment of coronary arteries that have been or will be subjected to PTCA or other artery-opening procedures, in order to inhibit intimal hyperplasia and reduce the risk of restenosis. Other areas of the vascular system in which the present invention is also useful include the carotid, renal, iliac, and subclavian arteries, peripheral arteries, vessels leading to and from the brain, anastomotic sites, vein grafts, and internal mammary grafts.

Bypass grafts may be treated with radiation either before or after they are implanted for bypass surgery. Non-vascular areas which the present invention is also useful include the brain ventricles, esophagus, trachea, bronchi, ureteral and urethral structures and other urological areas, vagina, uterus, and other gynecological areas, prostate gland and other male structures, biliary ducts, hepatic ducts, pancreatic ducts, and thoracic ducts. The present invention is also useful in areas of the body where endoscopic procedures are performed, and in the placement of shunts, such as dialysis shunts and transjugular intrahepatic portalsystemic shunts. Non-luminal areas of the body, including the brain, lungs, liver, gall bladder, pancreas, ovaries, cervix, endometrium, and prostate, may be treated through the delivery of treating elements via the catheter to a nearby intraluminal body passageway.

More specifically, as set forth in the appended claims, the present invention comprises an elongated flexible catheter tube having a proximal end portion adapted to remain outside the patient's body, a distal end portion adapted to be positioned at a selected location within the vascular system of the patient and a lumen extending therebetween, with the diameter of the catheter tube being sufficiently small for insertion into the patient's vascular system. The catheter tube is preferably but not necessarily adapted for positioning the distal end of the tube at the desired site by advancement over a guide wire. A port is provided at the proximal end portion of the tube, through which blood-compatible liquid may be introduced from a source of such liquid into the lumen. One or more treating elements, which may be in the form of a solid capsule, pellet or the like, such as a capsule or pellet containing radioactive material, is positionable within the lumen and is movable between the proximal and the distal end portions of the tube under the motive force exerted by the liquid flowing through the lumen.

In accordance with the present invention, a method is also provided for treating a selected area of the body of a patient wherein an elongated flexible catheter tube having a distal end portion adapted to be positioned at a selected location within an intraluminal passageway of the patient, a proximal end portion adapted to remain outside the patient's body, at least one lumen extending therebetween, and a diameter sufficiently small for insertion into the desired intraluminal passageway is introduced into an intraluminal passageway of a patient. The catheter is preferably but not necessarily introduced over a guide wire until the distal end portion of the tube is within the selected area of the vascular system. A port communicating with the first lumen is adapted for introduction of blood-compatible liquid into the lumen. One or more treating elements, such as a capsule or pellet containing radioactive material, is introduced into the lumen at the proximal end portion of the tube and is moved from the tubees proximal end portion through the lumen to the distal end portion within the selected area by flowing the blood-compatible liquid through the lumen to generate a motive force on the element so as to move it from the proximal end to the desired location at the distal end portion. There, the treating element is allowed to remain a sufficient time for treatment of the selected area, during which time the remaining portion of the catheter is free of treating elements so as to not unnecessarily expose other tissue to such treatment. After the treatment is completed, the catheter tube is removed from the patient. If the catheter tube is introduced over a guide wire, the catheter tube can be removed either over the guide wire or with the guide wire.

In another embodiment, the present invention is embodied in an angioplasty balloon catheter having proximal and distal end portions, with a lumen extending therebetween. The lumen communicates with an inflatable balloon located on the distal end portion. In accordance with the present invention, one or more treating elements, such as a radiation source, is either carried fixedly at the balloon or moved through a lumen from the proximal end portion to the distal end portion, for delivery of radiation to the stenotic site as the angioplasty procedure is actually carried out—therefore allowing what may otherwise be a two-step process to be carried out in a single step. From this summary, it should be apparent that the method of the present invention may be carried out before, during or after an angioplasty or other artery-opening procedure, whichever is deemed most desirable by the treating physician.

DRAWINGS

FIG. 6A is a partial cross-sectional view of a third embodiment of the elongated catheter tube of the present invention, showing the treating elements in the distal end portion of the tube.

FIG. 6B is a partial cross-sectional view of the FIG. 6A embodiment of the elongated catheter tube of the present invention, disposed within an outer guiding catheter which may be used to position the catheter tube of the present invention within the body of a patient.

FIG. 7A is a partial cross-sectional view of a fourth embodiment of the elongated catheter tube of the present invention, showing the treating elements disposed in the distal end portion of the tube.

FIG. 7B is a partial cross-sectional view of the elongated catheter tube of FIG. 7A taken along line 7–7B.

FIG. 8A is a partial cross-sectional view of a fifth embodiment of the elongated catheter tube of the present invention, showing the treating elements in the distal end portion of the tube.

FIG. 8B is a partial cross-sectional view of a modified version of the embodiment of the elongated catheter tube of FIG. 8A, showing the treating elements in the distal end portion of the tube.

FIG. 9 is a partial cross-sectional view of a sixth embodiment of the elongated catheter tube of the present invention showing toroidal or ring-shaped treating elements in the distal end portion of the tube.

FIG. 10 is a partial cross-sectional view of an alternative embodiment of the present invention having an inflatable balloon and treating elements fixedly positioned on the distal end portion.

FIG. 11 is a partial cross-sectional view of an alternative embodiment of the present invention having an inflatable balloon, with the treating elements disposed therein.

FIG. 12 is a partial cross-sectional view of another alternative embodiment of the present invention having an inflatable balloon, with the treating elements movable along the catheter.

FIG. 15A is a partial cross-sectional view of a further embodiment of the treatment delivery system of the present invention.

FIG. 15B is a elevational view of part of the proximal end portion of the treating system shown in FIG. 15A.

FIG. 15C is a cross-sectional view taken along lines 15c—15c of FIG. 15A.

FIG. 18 is a partial cross-sectional view of still another alternative embodiment of the present invention having an inflatable balloon, with the treating elements movable along the catheter.

FIG. 19 is a partial cross-sectional view of still another alternative embodiment of the present invention having an inflatable balloon, with the treating elements movable along the catheter.

FIG. 23 is an exploded perspective view of the rear housing and fluid control switch assembly of the transfer device of FIGS. 21 and 22.

FIG. 24 is a bottom view of the fluid control switch.

FIG. 27b is an enlarged view in partial cross section of the distal end of the delivery catheter of FIG. 27a.

FIG. 28a is an enlarged cross-sectional view of the distal end of a delivery catheter according to the present invention that permits perfusion through the guide wire lumen.

FIG. 28b is a cross-sectional view of the delivery catheter of FIG. 28a taken along line 28b—28b.

FIG. 29a is an enlarged cross-sectional view of the distal end of a delivery catheter according to the present invention that permits "rapid exchange" of the delivery catheter.

FIG. 29b is a cross-sectional view of the delivery catheter of FIG. 29a taken along line 29b—29b.

FIG. 32a is an enlarged cross-sectional view of the distal end of a delivery catheter according to the present invention located in situ and including an eccentric centering balloon.

FIG. 32b is a cross sectional view of the in situ catheter of FIG. 32a taken along line 32b—32b.

FIGS. 33a and 33b are similar to FIGS. 32a and 32b except that the centering balloon is in the shape of an eccentric coil.

FIG. 36a is a plan view of an alternate embodiment of a delivery catheter according to the present invention.

FIG. 36b is an enlarged cross sectional view of the catheter of FIG. 36a.

FIGS. 37a and 37b are cross sectional views of a catheter similar to that shown in FIG. 27c.

DETAILED DESCRIPTION

Figure 1:
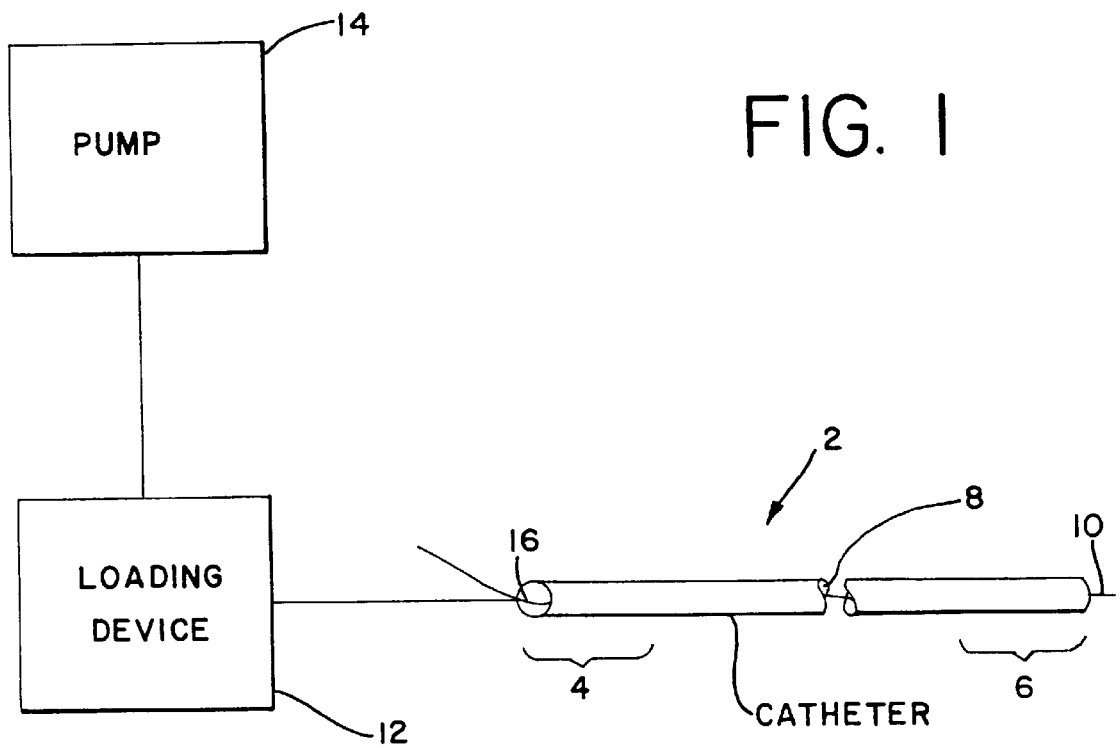
FIG. 1 is a diagrammatic representation of a catheter-based treatment delivery system embodying the present invention.

FIG. 1 depicts one embodiment of the present invention in general diagrammatic form for ease of initial understanding. The overall design of the apparatus of the present invention remains the same regardless of which intraluminal passageway will be used. However, the size of the apparatus or the materials from which it is made may be altered so that the maneuverability of the catheter in relation to the applicable lumen may be optimized. Shown in FIG. 1 is an elongated catheter 2 having a proximal end portion 4, a distal end portion 6, and at least one lumen 8 extending therebetween. The catheter is sized for insertion of the distal end portion through the vascular system of a patient to a selected area to be treated, such as the site of a balloon angioplasty procedure or other opening procedure, such as an atherectomy, in a coronary artery. This may be carried out, for example, by inserting the catheter percutaneously into a femoral artery and advancing the catheter over a typical guide wire 10 upwardly through the descending aorta, over the aortic arch, downwardly through the ascending aorta and into the particular coronary artery that has been selected for treatment, such as a coronary artery that has been subjected to PTCA or other artery-opening procedure. Guide wires and procedures used in advancing such a catheter to the point of the angioplasty procedure are well known and will not be discussed in detail.

At the proximal end of the catheter, which is located outside the patient in a percutaneous procedure such as described above, a transporting and/or loading device 12 is provided for loading a treating element, such as a pellet or capsule comprising or containing radioactive material, into the lumen 8 of the catheter 2. Additional treating elements may also be loaded such that the total length of the combined treating elements corresponds to at least the length of the stenotic area of the vasculature to be treated. The total length of the combined treating elements also could be longer than the stenotic area in order to assure that the end edges of the stenotic area are also treated. This loading procedure may also be performed manually, but a mechanical loader as described in more detail later is preferred to provide better user protection against radiation.

After the treating element is loaded into the lumen 8, pressurized blood-compatible liquid, such as sterile saline solution or sterile water, is introduced via liquid source 14 through a port 16 in the proximal end of the lumen behind the treating element. Flow of liquid through the lumen pushes the treating element along the lumen to the distal end portion, which is located at the site to be treated. The liquid which provides the motive force for moving the treating element may be allowed to exit from the distal end of the catheter or may be returned in a parallel lumen provided in the catheter or may be returned via suction through the same lumen in which the treating element travels.

After the treating element is located at the desired site, the treating element is allowed to remain for a time sufficient to treat the tissue. For radiation treatment of a stenotic site, the treating element preferably are beta-emitting radiation sources, and the residence time period will be relatively short, on the order of minutes as discussed in more detail below.

After the treatment is complete, the catheter may be removed with the treating element remaining at the distal end or, alternatively, liquid may be forced through the lumen in a reverse direction to return the treating element to the proximal end and into the loading device, if desired, before removal of the catheter. The reverse flow of fluid may be achieved by forcing liquid under positive pressure through the lumen in a reverse direction or by applying a suction, such as by withdrawing the piston of a syringe attached at the proximal end of the lumen, to the lumen.

The transporting/loading device 12 need not be connected directly to the proximal end of the catheter 2 if such direct connection would result in possible kinking of the catheter or would restrict maneuverability. In that case, an additional length of tubing (which may have the same number of lumens as the catheter) could be provided between the transporting/loading device 12 and the proximal end portion 4 of the catheter. In such event, the additional length of tubing (as well as the proximal end portion of the catheter located outside the patient) may be shielded to protect the user and/or the patient from unnecessary radiation exposure.

Figure 2A:
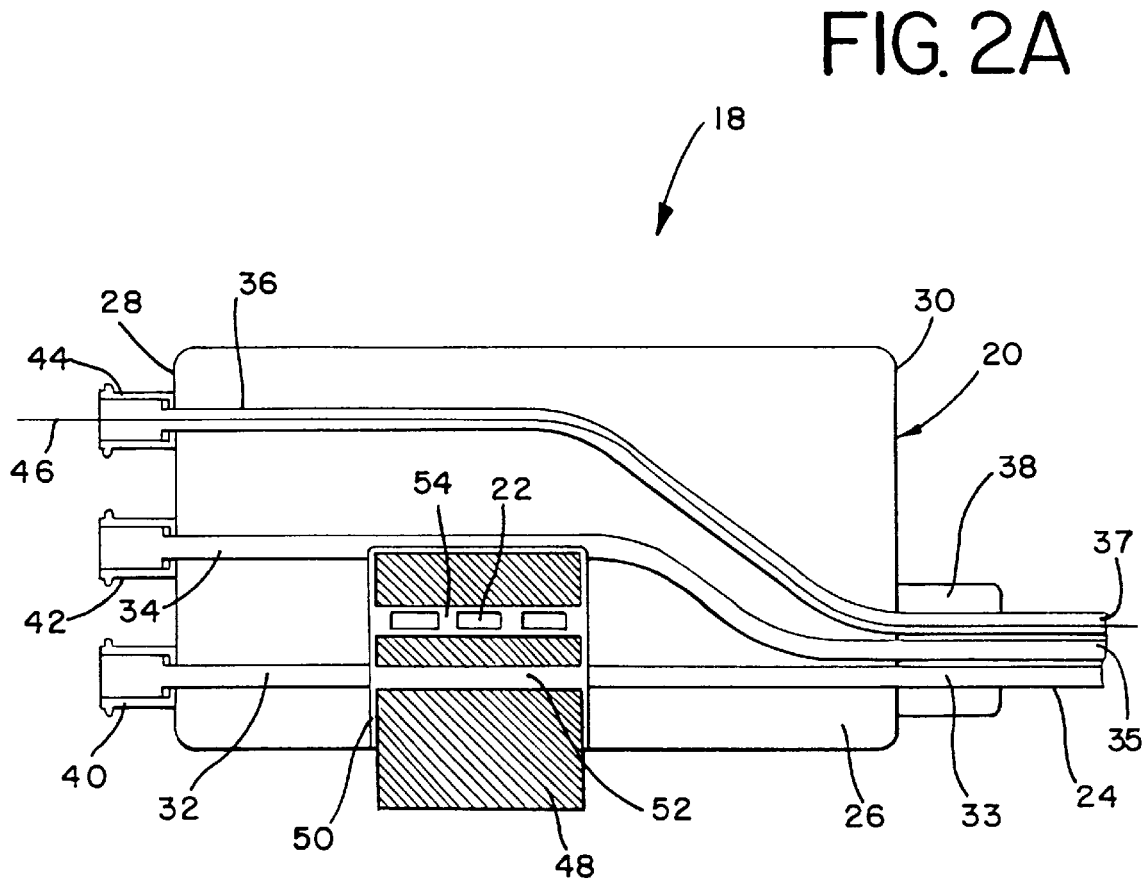
FIG. 2A is cross-sectional view of one embodiment of the proximal end portion of the treatment delivery system of the present invention.

FIG. 2A shows one actual embodiment of the proximal end of the catheter system depicted in FIG. 1. Although not limited to use with radioactive treating elements, the device shown in FIG. 2A is particularly adapted for that application.

Specifically, FIG. 2A depicts a three-lumen catheter system 18 with a loading device 20 containing treating elements 22 and connected to the proximal end of a three lumen catheter tube 24. The loading device comprises a rigid body 26 preferably of a suitable rigid polymer, having a proximal end 28, a distal end 30 and a first, a second and a third bore, 32, 34 and 36 respectively, extending therebetween. A fitting 38 located at the distal end of the body connects the first, second and third bores, respectively, with one of the three lumens 33, 35 and 37 of the catheter tube 24.

At the proximal end of the housing member, ports, such as luer connector ports, are provided for communication with bores 32, 34 and 36. A first port 40 is aligned with the first bore 32 of the body and is adapted for the entry or exit of a liquid, such as sterile saline. A second port 42 is in communication with the second bore 34 of the housing member and is likewise adapted to permit the entry or exit of liquid into the body. The third port 44 opens into the third bore of the body and is adapted to receive a guide wire 46 to aid in positioning the distal end of the catheter tube within a patient. A valve (not shown), such as a Touhy-Borst valve, may be attached to the third port to prevent leakage of fluid around the guide wire during or after insertion of the device into the patient.

For loading and/or unloading of the treating elements 22, a retaining device such as a magazine, carrier or carriage 48 is slidably positioned within a slot 50 defined in the body 26 intermediate the proximal and distal ends. The carriage is preferably constructed of the same material as the rigid body 26 and has a first through bore 52 and a second through bore 54. The first and second through bores of the carriage may be selectively aligned with the first bore 32 of the body, depending upon the lateral position of the carriage relative to the body. A carriage with only a single through bore may also be used.

By pre-loading the treating elements into the carriage, they may be conveniently handled, shipped and stored separate from the rest of the loading device. When the user is ready for the procedure, the carriage may be simply inserted into the body, thereby minimizing handling of the treating elements by and exposure to the user. The carriage is preferably made of a material and has sufficient thickness to protect the user against unnecessary exposure to radiation when the treating elements are radioactive.

As shown in FIG. 2A, carriage 48 is fully inserted into the body 26, with the first bore 52 of the carriage aligned with the first bore 32 of the body. In this position, second bore 54 of the carriage contains the treating elements 22 and is positioned within the body, thereby providing protection of the user from radiation emitted by the treating elements. In this first position, fluid, such as sterile saline, may be introduced through the first port to prime the body and catheter and remove any air contained therein, if so desired.

By sliding the carriage 48 outwardly from the body 26, the carriage is moved into a second position wherein second bore 54 of the carriage is coaxially aligned with first bore 32 of the body, and the treating elements 22 are ready for introduction into the catheter 24. In this second position, pressurized liquid, such as sterile saline, may be introduced via pump 14 through first port 40 to supply the motive force against the treating elements 22, ejecting them from second through bore of the carriage, distally through the first bore 32 of the body, and into a lumen of the catheter.

The specific design of the fluid source 14 may be chosen from various alternatives. For example, the fluid source 14 may be a simple saline-filled piston syringe attached via luer lock connector to port 40 of body 26. Manual depression of the syringe plunger would provide sufficient force to eject the treating elements and move them to the desired position in the catheter (and withdrawal of the plunger may assist in returning the treating elements to the proximal end portion after the treatment is complete). Alternatively, the motive force may be provided by a column of liquid from a suspended container of sterile saline or water, controlled by a simple roller clamp or stopcock.

Alternative configurations for the carriage (not shown) also may be used without departing from the scope of the present invention. For example, the carriage may be cylindrical and/or rotatably mountable within the body. Through bores or chambers within the carriage may be selectively brought into alignment with the bores of the body by rotating the carriage. The treating elements may be pre-loaded in the cylinder to minimize user contact and to protect the user from radiation when a radioactive treating element is employed. By providing the treating elements 22 pre-loaded into a loading device 20 or pre-loaded into a carriage 48 that may be inserted into a loading device, user contact with the treating elements is minimized, and for radioactive treating elements, the user may be shielded from radiation.

Figure 2B:
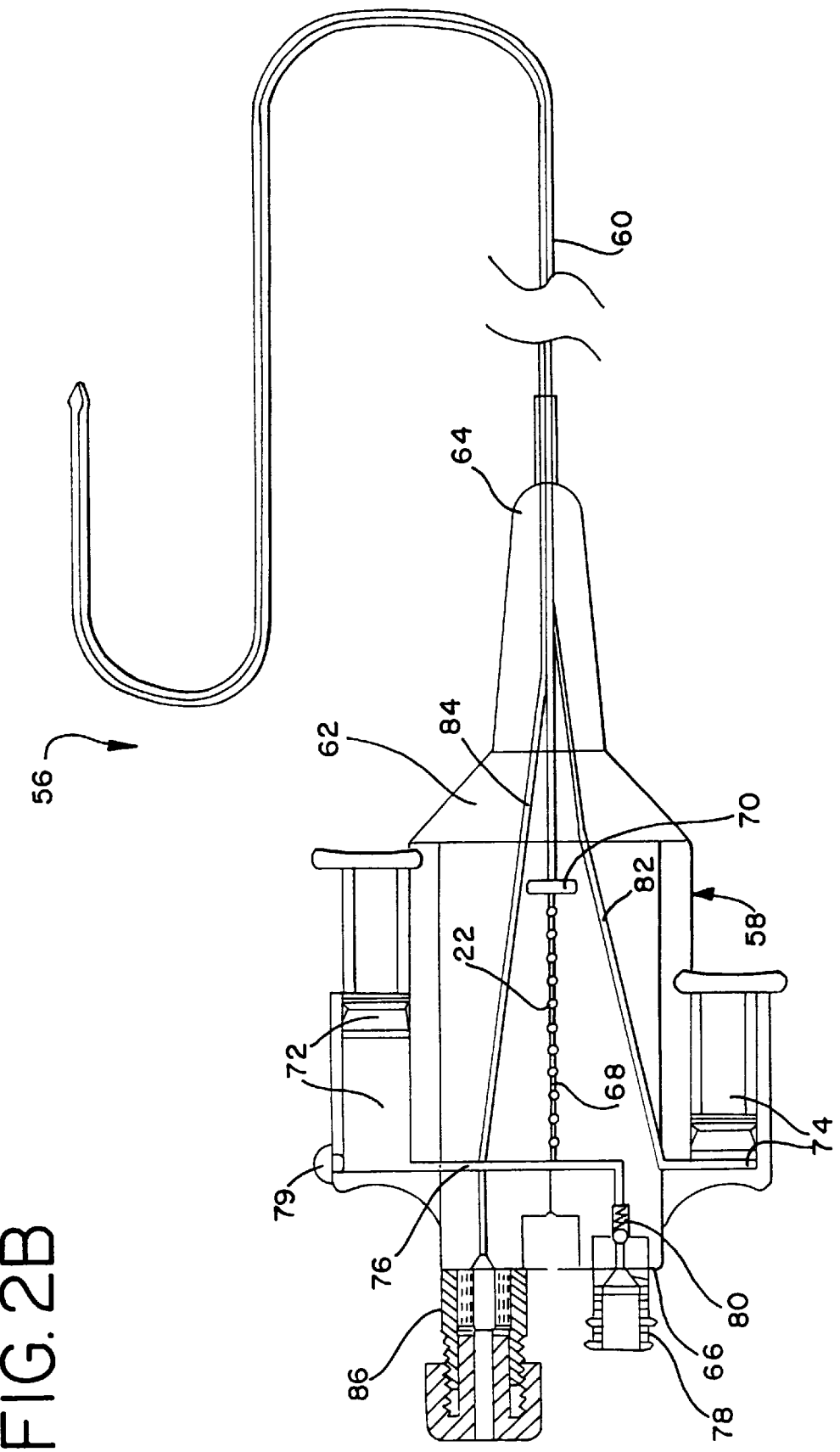
FIG. 2B is a cross-sectional view of another embodiment of the treatment delivery system of the present invention.

FIG. 2B shows a further alternative embodiment of a catheter system of the present invention. Catheter system 56 includes a combination loading device and pump 58 and a multi-lumen catheter 60. The combination pump and loading device comprises a body portion 62 having a distal end portion 64 attached to the elongated catheter tube and a proximal end portion 66 mounting connectors for fluid communication with passageways defined in the body.

The body portion 62 has a central bore or passageway 68 in which treating elements 22 are located prior to the treatment and after the treatment is completed. The central bore 68 communicates directly with one of the lumens of multi-lumen catheter 60. Discharge of the treating elements from the bore 68 is controlled by gate 70, which may be moved between positions blocking flow or allowing flow through central bore. Alternatively, the gate may contain openings of sufficiently small size to permit fluid to pass therethrough, while preventing passage of the treating elements while the gate blocks the central bore. This aids in priming the system with the treating elements in position in bore 68, if so desired.

For providing the pressurized flow of liquid to transport treating elements to and from the distal end of catheter 60, a pair of piston-cylinder arrangements are provided on opposite sides of the body portion 62. Piston-cylinder arrangement 72 provides the liquid flow for dispatching the treating elements to the distal end of the catheter and piston-cylinder arrangement 74 provides the reverse liquid flow for retrieving the treating elements therefrom.

Interior passageway 76 in the body 62 communicates between liquid inlet port 78, central bore 68 and the cylinder of dispatch piston-cylinder arrangement 72, which provides the fluid flow for moving the treating elements into and along a principal lumen of the catheter 60. One-way, spring loaded ball valve 80 within passageway permits liquid to enter through the inlet port but blocks liquid from exiting from the port. Vent 79 allows displacement air to exit from the passageway 76 when liquid is added, for priming purposes and the like, and a pressure relief valve (not shown) may be provided to prevent overpressurization of the catheter.

Interior passageway 82 in the body 62 communicates between the cylinder of the retrieval piston-cylinder arrangement 74 and a return lumen of the catheter 60. At the distal end portion of the catheter, the return lumen communicates with the principal lumen to provide a closed circulation path for the liquid that dispatches and retrieves the treating elements.

In addition, the body 62 has a third interior passageway 84 that communicates between guide wire inlet 86 and a guide wire lumen of the catheter 60. By itself, the catheter 30 may not have sufficient strength or torsional rigidity for insertion along a lengthy serpentine vascular path—in typical angioplasty procedures, the distance between the percutaneous entry point and the coronary artery may be approximately 3–4 feet (90–120 cm). To assist in positioning the distal end of the catheter at the desired location, the catheter may be advanced over a guide wire that is pre-inserted to the desired location in a manner well known to those skilled in performing angioplasty and similar procedures. The guide wire inlet preferably includes a Touhy-Borst valve or similar known device to close the guide wire inlet around the guide wire to restrict leakage of blood or other fluid from the guide wire lumen.

In use, the interior passageways, piston-cylinder arrangements, and catheter principal and return lumen are filled with sterile water or saline through the liquid inlet port 78 and one-way valve 80. In the initial position, the dispatch and retrieval piston-cylinders are oppositely positioned, with the piston of the dispatch piston-cylinder 72 in a withdrawn position, as shown in FIG. 2B, and the piston of the retrieval piston-cylinder 74 in an advanced position, also as shown in FIG. 2B. Before the treating elements can be moved to the desired position, gate 70 controlling the central bore must be opened.

By advancing the dispatch piston, the liquid in the dispatch cylinder is forced through the interior flow path 76 and into the central bore 68 containing the treating elements 22. The pressurized liquid flow ejects the treating elements from the central bore and forces the treating elements along the principal lumen of the catheter to the distal end portion located at the site to be treated. As liquid moves along the principal lumen in a distal direction, it displaces an equal amount of liquid that returns along the return lumen and enters the cylinder of the retrieval piston-cylinder arrangement 74, pushing the retrieval piston outwardly.

Retrieval of the treating elements may be accomplished by reversing the steps described above. The retrieval piston is advanced, forcing liquid in a reverse or distal direction along the return lumen and returning the fluid to the body along the principal lumen. The liquid flow moves the treating elements in a proximal or return direction along the principal lumen, returning them to the central bore of the body 62. The returning liquid enters the cylinder of the dispatch piston-cylinder arrangement 72.

With the catheter system as shown in FIG. 2B, a completely closed system is provided, and no liquid that contacts the treating elements is allowed to enter the patient's body. This may be particularly important when the treating agent is radioactive. The closed system arrangement also allows the treating elements, whether a single element or a train of treating elements, to be shifted back and forth slightly while in the distal portion of the catheter by alternately slightly depressing the dispatch and retrieval pistons. This technique may be used to provide a more uniform exposure of the selected vessel area, particularly where there is dead space between or at the ends of the treating elements.

Figure 2C:
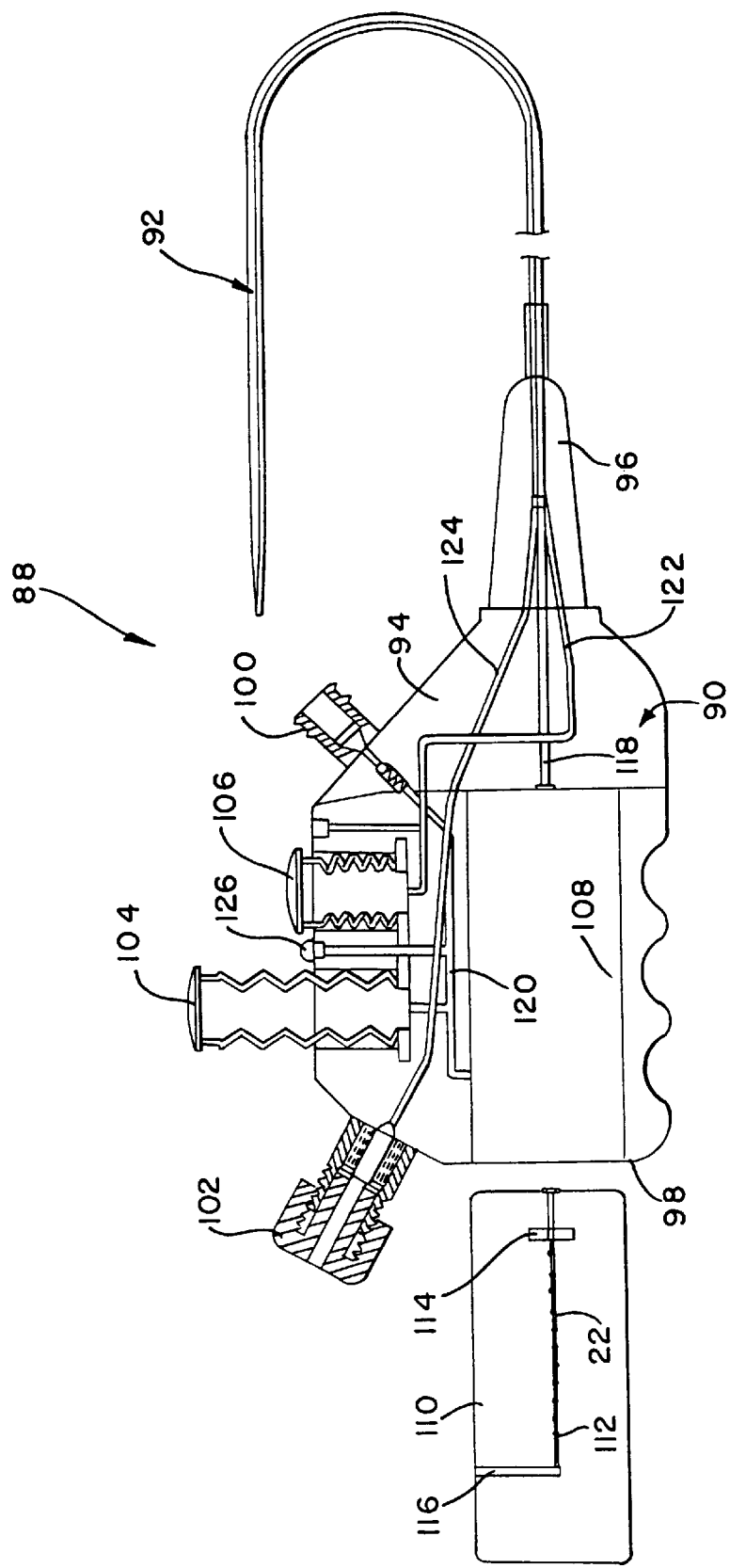
FIG. 2C is a cross-sectional view of still another embodiment of the treatment delivery system of the present invention.

A variation on the catheter system of FIG. 2B is depicted in FIG. 2C. The catheter system 88 shown there similarly includes a combination pump and loading device 90 and a multi-lumen catheter 92. The combination pump and loading device 90 also has a body portion 94 with a distal end portion 96 attached to the catheter 92, and a proximal end portion 98. In this embodiment, however, liquid inlet port 100, guide wire inlet 102 and dispatch and retrieval bellows 104 and 106, respectively, are located on one side of the body 94. This arrangement permits a large cylindrical chamber 108 to be provided, extending inwardly from the proximal end of the body, for receiving a carrier or insert 110 which is pre-loaded with treating elements 22. Alternatively, the body 94 and insert 110 could be of one piece or integral construction.

Insert 110 has a central bore 112 in which the treating elements are located, a gate 114 controlling passage of the treating elements from the central bore, and a laterally extending branch 116 of the central bore. When inserted into the chamber 108 of the body 94, central bore 112 of the insert 110 is aligned with central passageway 118 of the body 94, which communicates directly with a principal lumen of the catheter 92, and branch 116 communicates with internal passageway 120 of the body, which connects to the liquid inlet port 100 and the dispatch bellows 104.

Alternatively, the insert 110 could have a plurality of bores and be rotatably mounted in the body for selective alignment of the bores with inlet port 100 and central passageway 118. In this arrangement, one bore could be empty for fast priming of the system and another bore could contain the treating elements.

As with the embodiment in FIG. 2B, an internal liquid flow passageway 122 is provided in the body 94, communicating between the retrieval bellows and a return lumen of the catheter 92, and a guide wire passageway 124 is provided between a guide wire lumen of the catheter and guide wire inlet 102. Also similarly, a vent 126 is provided in communication with the passageway that connects with the liquid inlet port 100.

In operation, the catheter system of FIG. 2C is essentially identical to that discussed regarding FIG. 2B. The embodiment of FIG. 2C allows the treating elements to be conveniently stored separately from the remainder of the catheter system, for example in special radiation-proof containers.

It should be clear that in each of the embodiments discussed above, the body, carrier (insert or carriage) and catheter may be provided in various combinations of assemblage, as a matter of choice. For example, the body and carrier could be preassembled or even of one piece construction. Similarly, the body could be preassembled with the catheter tube, with the carrier separate for convenient storage and transportation of the treating elements. Alternatively all three elements could be separate and assembled in the desired configuration on site—this would permit the physician to select the appropriate combination depending on the desired procedure.

For radiation exposure of the desired site, the treating elements 22 contain radioactive material, preferably beta-emitting. In the preferred embodiment shown in FIG. 3, the treating elements are elongated hollow cylinders 128 which are preferably constructed of stainless steel, silver, titanium or other suitable material, and are ideally in the range of 2.5 to 5.5 mm in length. The cylindrical treating elements have rounded first and second ends with a chamber 130 extending therebetween. The inner diameter of chamber 130 is preferably in the range of 0.4 to 006 mm. A first end plug 132 closes the first end of the cylinder, while a second end plug 134 closes the second end. The end plugs are preferably less than about 1 mm in width and are affixed to cylinder 128, for example, by welding.

The outer diameter of the treating elements is preferably between approximately 0.6 and 0.8 mm, being sized, of course, to slidably fit into the respective receiving bores of the carriages, bodies and catheter lumen described above. To permit maximum mobility through the loading devices and catheters described above, the inner diameter of each of the bores or lumens the treating elements pass through should preferably be less than twice the outer diameter of the cylindrical treating elements and the outer surface of the treating elements may be coated with Teflon material or similar low-friction material to reduce friction between the treating element and the wall of the lumen in which it moves. This allows the treating elements to move quickly through the lumen, minimizes unnecessary exposure of other tissue to the treating elements and in particular minimizes radiation exposure to other tissue. Additionally, to increase the surface area of the treating elements subject to the motive force provided by fluid being passed through the system, the treating elements may also be provided with one or more annular ridges which extend outwardly about the circumference of the treating elements.

Figure 3:
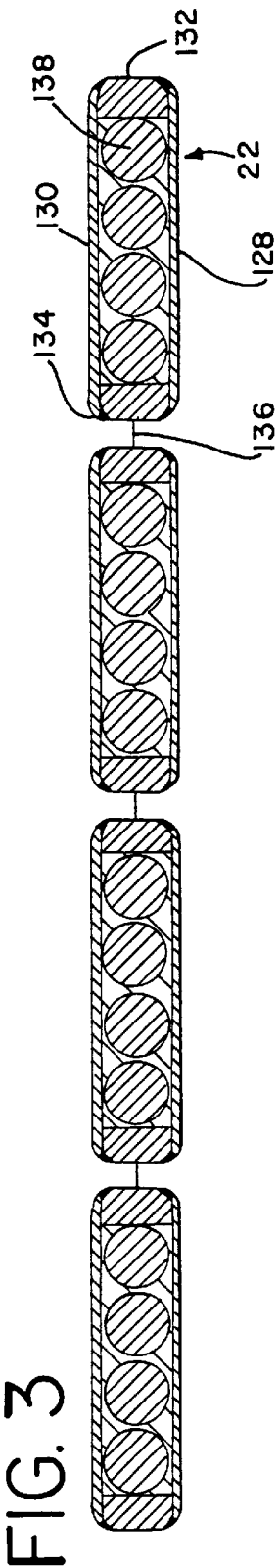
FIG. 3 is a cross-sectional view of one embodiment of the treating elements of the present invention.

To treat a length of vascular tissue, a plurality of individual, non-connecting treating elements, positioned end-to-end to form a train of treating elements, as illustrated in the attached figures, may be used. To keep the treating elements uniformly spaced from each other, and, more importantly, to prevent the treating elements from becoming too spaced apart while moving through the catheter, the individual treating elements, however, may be connected by several lengths of hard tempered spring wire 136, as is shown in FIG. 3.

Each treating element 22, as constructed above, encapsulates a therapeutic agent, such as a radiation emitting substance 138. Radiation emitting substance 138 is contained within interior chamber 130 of the treating element and may be composed of any alpha, beta or gamma particle emitting substance. Preferably, however, the radioactive source is a pure beta-particle emitter, or beta and gamma emitter. Examples of such substances include Strontium$^{90}$, Ruthenium$^{106}$, Phosphorus$^{32}$, Iridium$^{192}$, and/or Iodine$^{125}$.

The amount and strength of the radioactive material contained in the combined number of treating elements 22 should be sufficient to deliver a desired dosage of from 100 to about 10,000 rads, preferably about 700 to 5,000 rads, in about 2–10 minutes. In trials of the device, doses of between 1200 and 1600 rads have been delivered over a period of between two and four minutes. Radioactivity is generally measured in units of "Curie" (Ci), and the radioactivity of the material for the present invention is selected to provide the above dosage. For the preferred dosage, the radioactive material may have a radioactivity of approximately 0.45 and 25,000 mCi per centimeter of vessel to be treated, depending on the radiation source used. As described briefly earlier, when a train of treating elements is used which have dead space (non-radioactive) between adjacent elements, the train may be oscillated by moving the catheter slightly back and forth or by briefly repeatedly reversing the flow of liquid, resulting in a shifting back and forth of the treating elements to provide a more uniform radiation exposure of the selected area of the vessel.

The selected radioactive material may be contained within glass, foil, or ceramics, or, alternatively, within a powder or liquid medium, such as microparticles in liquid suspension When solid materials are used, the preferred outer diameter of the material is approximately 0.5 mm, allowing it to be inserted into the central chamber 130 of the treating element cylinder 128. Such radioactive materials may be formed into pellets, spheres, and/or rods in order to be placed into the chamber of the treating element.

Various alternative treating elements may also be used to contain the radioactive material without departing from the present invention. For example, the treating elements may be toroidal, spherical, or in the form of elongated rings, and in such configurations, the radioactive material may be actually impregnated in a metal and formed into the desired shape. Alternatively, a radioactive powder may be fired to fuse the material so that it may be formed into the desired shape, which may then be encapsulated in metal, such as titanium, stainless steel or silver, or in plastic, as by dipping in molten or uncured plastic. In still another embodiment, the treating elements may be formed from a ceramic material which has been dipped in a radioactive solution. In a still further alternative, the treating elements 22 may be constructed in the form of two piece hollow cylindrical capsules having a larger-diameter half with a central cavity and a smaller-diameter half also having a central cavity, the smaller half slidably received within the larger half and bonded or welded to form the capsule structure.

Turning now to a more detailed description of the catheters of the present invention, as stated previously, catheters of the present invention may be pre-attached to the loading device or, as discussed with regard to FIG. 2, a fitting such as 38 may be provided for attaching an elongated catheter tube to the loading device. Although catheters of the present invention may vary in the number of lumens or the specific construction of such lumens, those catheters have in common, a proximal end attachable to a body member such as body 26, a distal end opposite the body which is adapted to be positioned at a selected site in the body, and an elongated tubular portion therebetween. For those catheters that are not pre-attached to the loading device, the proximal end may be provided with a keyed fitting to allow attachment of only certain catheters to the fitting on the loading device. Such fittings may include those generally known in the art which will not be discussed herein, but also may include specially designed fittings which would be peculiar to this device. A specially keyed fitting would prevent the inadvertent attachment of the fitting or body to other catheters on the market which are not specifically designed to receive the treating elements and/or to prevent the treating elements from being released into the body.

As used herein, the terms "elongated tube," "elongated catheter tube" and similar phrases are intended to include a catheter possessing one or more lumens produced from a single extrusion and catheters of multiple lumens wherein the catheter is made up of several separate tubes bundled together.

Figure 4:
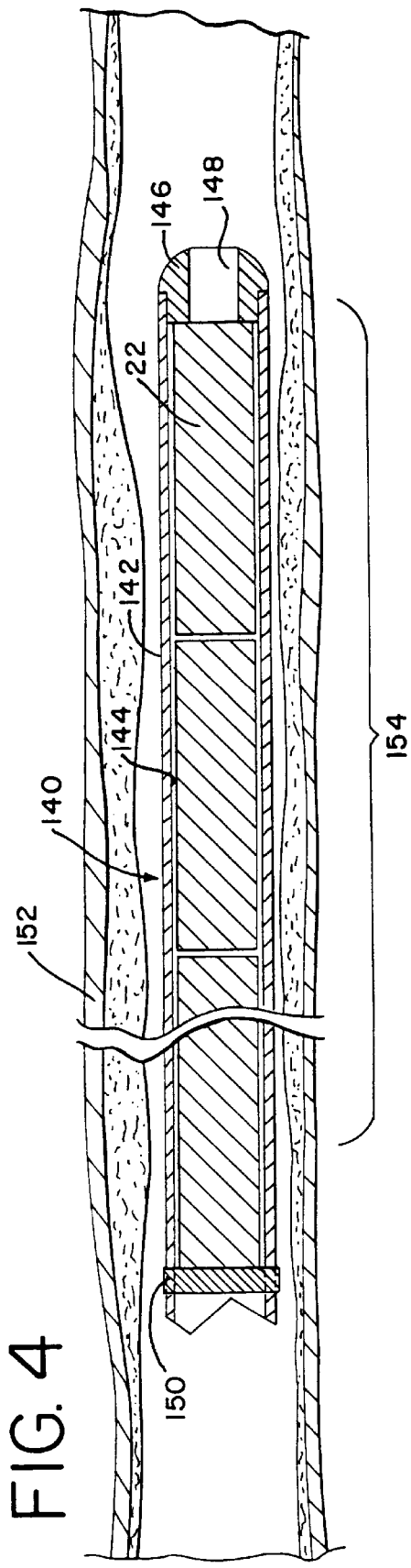
FIG. 4 is a partial cross-sectional view of one embodiment of the elongated catheter tube of the present invention, showing the treating elements disposed in the distal end portion of the tube.

FIG. 4 depicts the distal end portion of one catheter of the present invention, generally at 140, with the treating elements located in the distal end portion. In this embodiment, the catheter comprises a single tubular member 142 having a proximal end portion (not shown), a distal end portion and a lumen 144 extending therebetween. The tubular member is preferably extruded from Nylon 11 material, although other suitable plastic materials may be used. The outer diameter of the tubular member is sized according to the intended application—for example 5 French or smaller for use in treating the stenotic site of a coronary artery. The inner diameter of the lumen is correspondingly sized to receive the treating elements 22.

To prevent treating elements 22 from exiting the distal end of the tubular member, a retention projection may be provided in the lumen to block passage of the treating elements, such as an end barrier 146. Barrier 146 is a separate molded tip adhered or bonded to the distal end portion of tubular member 142. Barrier 146 preferably has a smooth rounded external surface to minimize possible abrasion to a vessel or other tissue and a central opening 148 to allow liquid flow therethrough.

To aid in placement of the catheter at the desired location, a marker band 150 is attached to the outer surface of tubular member 142 at the distal end portion. To provide a continuous smooth outer surface, a slight undercut may be provided in the surface of the catheter tube, in which the marker band resides. Although shown on the exterior surface of the catheter, the marker band may also be provided internally as well. Preferably the barrier 146 and marker band 150 are constructed from barium, a platinum-iridium compound, or like substance, which is visible by fluoroscope during placement of the catheter.

In use, still referring to FIG. 4, the distal end portion of the tubular portion is introduced into the body of a patient into a selected site, such as the coronary artery 152 following balloon angioplasty. In such instances, a guide wire will typically be pre-positioned in the patient, although a guiding catheter could also be used. The distal end of the catheter is then advanced over the guide wire, through lumen 144. The positioning of the device is made more precise due to the ability to fluoroscopically observe the barrier 146 and marker band 150 at the distal end portion of the catheter tube.

After the distal end portion of the catheter is positioned such that the previously stenosed area, generally at 154, of the coronary artery is located between the barrier 146 and marker band 150, the guide wire can be removed, and the proximal end of the catheter can be connected to a treating element loading device and/or pump, as described earlier with reference to the FIG. 2–2B embodiments.

So connected, the treating elements 22 are in direct communication with lumen 144 of the catheter and a flow path is formed therebetween. Pressurized liquid, such as from a fluid pump, syringe or other piston-cylinder arrangement, plunger, or elevated saline solution container, is then directed against the treating elements, causing them to advance along the catheter lumen until stopped by the end barrier 146.

Referring to the FIG. 2A embodiment of a loading device as an example, to move the treating elements 22 from the body 26 to the selected site in the patient, the carriage 48 is moved from the first position to the second position. This releases the treating elements into the flow path where they are carried rapidly by the motive force of the fluid therein into and through the lumen of the catheter to the distal end portion, which is located at the stenotic site. The rapid transportation of the treating elements reduces the amount of radiation which is transmitted to tissues in the body through which the elongated catheter tube extends. In this embodiment, the liquid transporting the treating elements exits through the central opening 148 in the end barrier 146.

As noted above, upon reaching the distal end portion of the elongated tube, the treating elements are prohibited from being ejected into the patient by the barrier 146. Once more, the barrier and marker band may be used to fluoroscopically visualize the released radioactive elements, and account for their location. The barrier and marker band may be specifically spaced to cover the distance of the lumen occupied by the total length of the radioactive treating elements, and the location of the elements may be confirmed by viewing a solid image between the barrier and marker band on the fluoroscope.

To maintain the treating elements within the distal end portion of the elongated tube, a constant fluid pressure through the lumen and against the treating elements may be required to counteract the effects of external blood pressure and/or gravitational forces exerted upon the treating elements, depending on the angle at which the distal end portion of the elongated tube is placed and on the specific location in the patient.

Preferably, in order to sufficiently irradiate the stenotic site of a coronary artery that has been subjected to PTCA to inhibit intimal hyperplasia, the treating elements should remain at the selected site for a sufficient time to deliver a therapeutically effective amount of radiation, which is preferably between about 100 and 10,000 rads, preferably about 700 to 5,000. The length of time required to deliver this dosage of radiation depends primarily on the strength of the radioactive source used in the treating elements and the number of treating elements employed. The radioactivity needed will depend on the strength of the source used and the emission, and may be in the range of 0.45 to 25,000 mCi depending on the source. After sufficient time, such as 2 to 10 minutes, has been allowed for treatment, the treating elements may be removed by withdrawing the catheter from the patient or by applying suction (such as by a syringe) to the proximal end of the lumen in which the treating element travels. In trials of the device, doses of between 1200 and 1600 rads have been delivered over a period of between two and four minutes.

Figure 5:
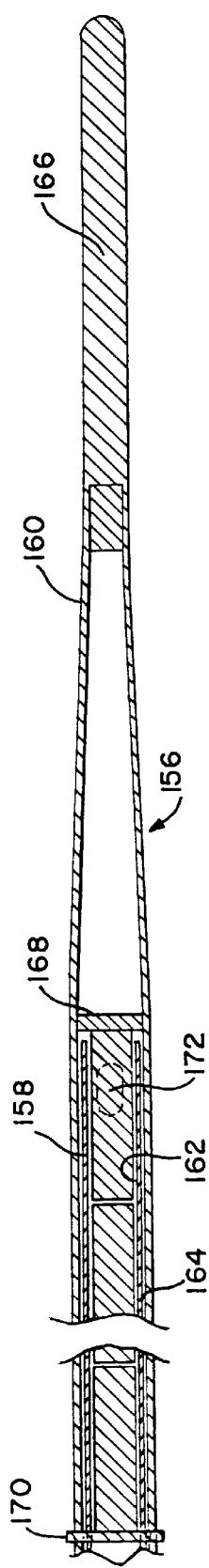
FIG. 5 is a partial cross-sectional view of a second embodiment of the elongated catheter tube of the present invention, showing the treating elements in the distal end portion of the tube.

Another embodiment of an elongated catheter tube 156 of the present invention is shown in FIG. 5. The proximal end of the catheter tube may be pre-attached to a loading device/pump or employ a fitting for keyed attachment to such a device, as described in detail earlier. Accordingly, only the distal end portion of the catheter is depicted in FIG. 5.

As shown in FIG. 5, the elongated tube 156 comprises co-axial inner and outer tubes 158 and 160 respectively. Inner tube 158 defines an inner bore or lumen 162, through which the treating elements 22 are advanced. Inner and outer tubes are spaced apart to define a return lumen 164 therebetween for return of the liquid used to advance the treating elements.

The distal end of the outer tube 160 tapers to a narrow, flexible and atraumatic tip 166 bonded to the outer tube. A radiopaque barrier 168 located slightly beyond the end of the inner tube 158 closes the outer tube 160 and blocks further proximal movement of the treating elements 22. Similarly to marker band 150 of the previous embodiment, a marker band 170 may be provided in an undercut area on the surface of outer tube 160 at a location spaced proximally from the barrier 168 to enhance placement of the distal end portion and the treating elements at the desired location.

When used to treat the site of a coronary artery where a balloon angioplasty procedure has been carried out, this catheter 156 is positioned in the previously stenosed site by a guide tube or similar device. Positioning of the distal end portion of the catheter may be viewed fluoroscopically due to the radiopaque barrier 168 and marker band 170.

If not pre-attached to a loading device/pump, the proximal end of the catheter is attached to such a device as described earlier. Without unnecessarily repeating earlier description, the treating elements 22 are advanced along the inner lumen 162 of the catheter under the force of liquid flowing therethrough. With this embodiment, instead of exiting from the distal end of the catheter, the liquid exits from the distal end of the inner lumen (or through a side aperture 172 in the wall of the inner tube) and returns through the return lumen 164 provided between the inner tube and the outer tube. The return liquid may be allowed to exit through the loading device/pump or may be collected therein, as described earlier, for alternative disposal.

Unlike the first embodiment, this embodiment is a completely closed system, in that the fluid is not released into the patient and the treating elements 22 do not contact the blood. While this eliminates the effects of blood pressure in moving the treating elements, a small but constant fluid flow may be required to maintain the treating elements in the distal end portion of the elongated catheter tube due to the gravitational effects in the event the treatment site is at a higher elevation than the proximal end of the catheter. By oscillating the liquid flow between the dispatch and retrieval pistons, the train of treating elements 22 may be shifted slightly back and forth to make the exposure along the desired area more uniform.

The radioactive treating elements remain in the distal end portion of the elongated tube for a sufficient period of time to deliver a therapeutically affective amount of radiation. As was previously discussed, this is preferably about 100–10,000 rads, in the case of inhibiting the development of intimal hyperplasia.

After a sufficient amount of radiation is delivered, the treating elements 22 may be retrieved from the distal end portion of the elongated catheter tube and returned to the loading device by introducing pressurized fluid into the return lumen. This reverses the flow of liquid and creates an oppositely directed motive force on the treating elements forcing them proximally through the inner lumen 162 for return to the loading device. The elongated catheter tube may then be removed from the patient and the procedure concluded. Alternatively, the treating elements may be removed by withdrawing the catheter from the patient.

In a third alternative embodiment of the present invention shown in FIGS. 6A and 6B, the catheter is constructed and operates similarly to that described for the FIG. 5 embodiment. Elongated catheter tube 174 comprises co-axial inner and outer tubes 176 and 178 respectively. Inner tube 176 defines an inner bore or lumen 180, through which the treating elements 22 are advanced. Inner and outer tubes are spaced apart to define a return lumen 182 therebetween for return of the liquid used to advance the treating elements.

The distal end of the outer tube 178 is not tapered, but is closed by radiopaque solid tip 184, which also serves as a barrier to the treating elements as they move along the inner lumen 180. Also similarly, a marker band 186 is provided on the surface of outer tube 178 at a location spaced proximally from the tip 174 to enhance placement of the distal end portion and the treating elements at the desired location.

The initial placement of the distal end portion of elongated catheter tube 174 is facilitated by the use of a third or guide tube 188, as is shown in FIG. 6B. As shown therein, the separate third tube 188 has a proximal end portion (not shown), a tapered distal end portion and a lumen 190 extending therebetween.

In use, the guide tube has sufficient strength or rigidity for placement or is placed into the body of a patient over a pre-positioned guide wire, so that the distal end portion of the third tubular member is located at a specific selected site within the body at which treatment is desired. Once the guide tube is positioned at the selected site, and the guide wire at least partially pulled back, the elongated catheter tube 174 shown in FIG. 6A may be inserted into lumen 190 of the guide tube.

As in the FIG. 5 embodiment, the embodiment shown in FIGS. 6A and 6B allows treating elements 22 to be hydraulically moved between the proximal and distal end portions of the elongated tube, with the direction of the hydraulic flow being determined by the pressure gradient existing between the delivery and retrieval lumens. Thus, after maintaining the treating elements at the distal end portion of the elongated catheter tube for a desired period of time, the treating elements may be retrieved by reversing the flow of fluid through the elongated tube. Following this the catheter and third or guide tube may be removed from the patient and the procedure concluded.

Another embodiment of the catheter of the present invention, particularly intended for placement at a desired location by advancement over a guide wire, is shown in FIGS. 7A and 7B. The elongated catheter tube 192 comprises a pair of inner tubes 194 and 196 that extend in a parallel side-by-side arrangement within an outer tube 198. Inner tube 194, which is of smaller diameter than tube 196, defines an inner lumen 200 for receiving a guide wire used for placement of the catheter at the desired location within the patient. Inner tube 196, which is of larger diameter, provides inner lumen 202 along which the treating elements 22 travel. Return lumen 204 is provided by the space between the inner surface of the outer tube 198 and the outer surfaces of the inner tubes 194 and 196 for return flow of liquid used to transport the treating elements.

As seen in FIG. 7A, the outer tube 198 has an open tapered distal end. An interluminal wall 206 is provided within the outer tube at the beginning of the taper and at the distal end of the inner tubes 194 and 196. The wall 206 includes an aperture in sealed communication with lumen 200 of inner tube 194, through which a guide wire may pass. The wall 206 is preferably slightly spaced from the distal end of the other inner tube 196, through which the treating elements pass, to allow liquid to exit from the end of tube 196 for return through the return lumen 206. The wall also provides a barrier to prevent the treating elements from exiting the end of tube 196.

As in the earlier embodiments, the elongated catheter tube 192 has first and second radiopaque marker bands, 208 and 210 on the outer tube to aid in placing the distal end portion at the desired location in the patient. As noted earlier, although generally depicted on the outer tube in many of the embodiments, the markers may be provided inside the catheter at any convenient location, such as on an inner tube or surface, without departing from the present invention.

In use for treating a stenotic site in a coronary artery with radiation, the proximal end of the elongated catheter 192 tube may be pre-connected to a loading device/pump or separately connected to such a device by a keyed fitting or similar arrangement, as discussed earlier. The distal end portion of the elongated catheter tube is then positioned at the selected site within the body of the patient by advancing the catheter over a pre-positioned guide wire. In this embodiment, the guide wire may be allowed to remain in position. This has the significant advantage that it is unnecessary to insert the guide wire a second time if a further catheter or device needs to be inserted after the treatment is completed.

The radiopaque marker bands 208 and 210 are visible on a fluoroscope and aid in the placement of the device. When the distal end portion of the elongated tube is positioned such that the selected site is located between marker bands 208 and 210, liquid may be pumped through the lumen 202 to move the treating elements to the distal end portion of the elongated catheter tube, where they are accounted for by the positioning of the marker bands. After sufficient irradiation has occurred, the flow through the device is reversed by reversing the flow of pressurized fluid through the return lumen causing return of the treating elements to the loading device. The elongated catheter tube may then be removed from the patient and the procedure completed.

A further alternative embodiment of the catheter of the present invention, preferably intended for placement over a guide wire, is shown in FIGS. 8A and 8B. The elongated catheter tube 212 comprises a pair of inner tubes 214 and 216 that extend in a parallel side-by-side arrangement within an outer tube 218. As in the FIG. 7 embodiment, inner tube 214, which is of smaller diameter than tube 216, defines an inner lumen 220 for receiving a guide wire used for placement of the catheter at the desired location within the patient. Inner tube 216, which is of larger diameter, provides inner lumen 222 along which the treating elements 22 travel. A return lumen similar to return lumen 204 shown in FIG. 7B is provided by the space between the inner surface of the outer tube 218 and the outer surfaces of the inner tubes 214 and 216 for return flow of liquid used to transport the treating elements, in the very same manner as depicted in FIG. 7B. In the FIG. 8 embodiment, however, inner tube 214 (for the guide wire) extends fully along the length of the outer tube 218, and is bonded to the outer tube at the distal-most location, where the outer tube is tapered.

In FIG. 8A, an internal barrier 226 is provided at the end of the inner tube 216, through which the treating elements are carried, to block the passage of treating elements from the distal end of the tube 216. A center opening in the barrier 226 allows liquid to pass from the lumen 222 of the inner tube 216 to the return lumen. Alternatively, the barrier may be solid as depicted with barrier 228 in FIG. 8B (which is otherwise the same as FIG. 8A), and an aperture 230 may be provided in the wall of inner tube 216 to permit liquid to flow between the treating element lumen 222 and the return lumen. Although not depicted in FIGS. 8A or 8B, it should be understood that the elongated catheter tube may also include a series of marker bands appropriately placed along the length of the tube to aid in accurate placement in the patient.

Another embodiment of the catheter of the present invention is shown in FIG. 9. As shown there, catheter 232 has three co-axial tubes, inner tube 234, outer tube 236 and intermediate tube 238, which all extend the full length of the catheter. Inner tube 234 has a lumen 240 for receiving a guide wire for placement of the catheter at the desired location in the patient. Inner tube 234 is spaced from intermediate tube 238 to define an annular treating element passageway 242 therebetween. In this embodiment, the treating elements are preferably ring shaped, as at 244, or donut shaped, as at 246, to allow them to slide over the inner tube 234 and along the passageway 242. To provide a return flow channel, the inner diameter of the outer tube 236 is slightly larger than the intermediate tube 238 to provide a return flow path 248 therebetween.

The end of the catheter is closed by a molded tip plug 250, preferably of radiopaque material, bonded to the ends of the inner and outer tubes 234 and 236. Center passageway 252 through the tip plug allows for the passage of a guide wire or the like for placement of the catheter at the desired location. The distal end of the intermediate tube 238 stops short of the tip plug, thereby allowing the treating element passageway 242 to communicate directly with the return flow path 248. Radiopaque marker bands, although not shown, may also be incorporated on the distal end portion of the elongated catheter tube to aid in placing the elongated tube within the body at the selected site.

After the distal end portion of the elongated tube is positioned at the desired location in the patient, a liquid, such as saline, is forced through the treating element passageway 242 and directed against the ring-shaped treating elements, moving the treating elements along the passageway over the inner tube 234 until they abut the distal tip plug 250. The radioactive elements are retained at the distal end portion of the elongated catheter tube for a sufficient time to deliver the therapeutically effective amount of radiation to the selected site. To retrieve the treating elements, the fluid flow is reversed through the flow path by forcing liquid in a distal direction through the return lumen. Following this the elongated tube can be removed over the guide wire and the procedure completed.

In a still further embodiment of the present invention, shown in FIG. 10, a catheter 254 is provided which includes both an inflatable balloon membrane 256 for carrying out a balloon angioplasty procedure and treating elements 22 fixed in the distal end of the catheter for simultaneous treatment. The catheter of FIG. 10 includes an elongated tubular portion 258, typically of extruded construction, with a guide wire lumen 260 and an inflation lumen 262. A balloon membrane is located at the distal end of the catheter tube and sealed to the exterior surface to form an inflatable balloon. Port 264 communicates between the inflation lumen and the inside of the balloon for inflating the balloon by pressurized liquid. Only the distal end portion of the catheter is shown—the proximal end of the catheter being typical of angioplasty catheter construction as is well known to those skilled in the field.

To perform radiation treatment simultaneously with a balloon angioplasty procedure, radioactive treating elements 22 are located within the balloon, between coaxial walls 266 and 268 of the distal end portion of the catheter. The treating elements are ring-shaped or donut-shaped, as described earlier, and positioned over the inner wall 266. Stop rings 270, preferably of radiopaque material, are positioned at each end of the string of treatment elements to maintain the treatment elements at a fixed location within the balloon and aid in locating the catheter at the desired location.

The strength and other characteristics of the radioactive treating elements are essentially as described earlier and will not be repeated. With this construction, the balloon angioplasty procedure and the radiation treatment of the stenotic site may be carried out simultaneously instead of sequentially, thereby further reducing the time, cost and risk associated with such procedures.

In use, catheter 254 is positioned into the stenosed area of the artery over a pre-positioned guide wire. Using the radioactive treating elements alone or in conjunction with the radiopaque end rings, the distal end portion of the catheter is positioned such that the balloon portion is located at the stenosed site. Pressurized fluid introduced into the proximal end of the inflation lumen, as with a syringe, enters through port 264, inflating the balloon. The expanding balloon membrane 256 compresses the sclerotic plaque and increases the diameter of the blood vessel. The balloon may be deflated and the distal tip retained in this position for the desired period of time to deliver an effective amount of radiation to the previously stenosed area. The device may then be removed from the patient and the procedure completed.

FIG. 11 shows a variation of the radiation delivery system of FIG. 10. In the FIG. 11 embodiment, the basic operation and construction of the catheter are the same as described with respect to that shown in FIG. 10, except that in FIG. 11, the radioactive treating elements are located on inner tube 272 and directly below balloon membrane 274. Balloon membrane may be inflated by the introduction of pressurized fluid through inflation lumen 276 defined between inner tube 272 and co-axial outer tube 278.

FIG. 12 shows the distal end portion of another balloon catheter 280 embodying the present invention. The catheter 280 employs three coaxial tubes, inner tube 282, outer tube 284 and intermediate tube 286. Inner tube 282 defines an inner lumen 288 through which a guide wire may extend for placement of the catheter at the desired location. The space between the inner tube and the intermediate tube 286 defines an annular lumen 290, through which ring-shaped or donut-shaped treating elements may pass. The space between the intermediate tube and the outer tube 284 forms a return lumen 292 for return of liquid used to transport the treating elements.

The catheter 280 also includes a balloon membrane 294 bonded at one end to the exterior surface of the outer tube 284 and bonded to the exterior surface of the inner tube 282 (which extends beyond the distal ends of the intermediate and outer tubes) at the other end. The distal end of the outer tube is closed by a barrier 296, which may be radiopaque, to block the exit of the treating elements from the distal end of lumen 290. In this embodiment, the same liquid used to transport the treating elements is also used to inflate the balloon membrane, although that is not required if a separate inflation lumen were provided. To inflate the balloon membrane, a side opening 298 or port is provided in the wall of the outer tube 284 and also in the intermediate tube 286 if desired. With this construction, pressurized blood-compatible liquid, such as sterile saline, may be used to advance the treating elements while simultaneously advancing the treating elements to the distal end portion of the catheter. The treating elements may be retrieved by reversing the flow of the liquid through the return and treating element lumen 292 and 290, respectively. Further release of pressure exerted upon the liquid will allow the balloon to deflate and the catheter to be removed.

Figure 13:
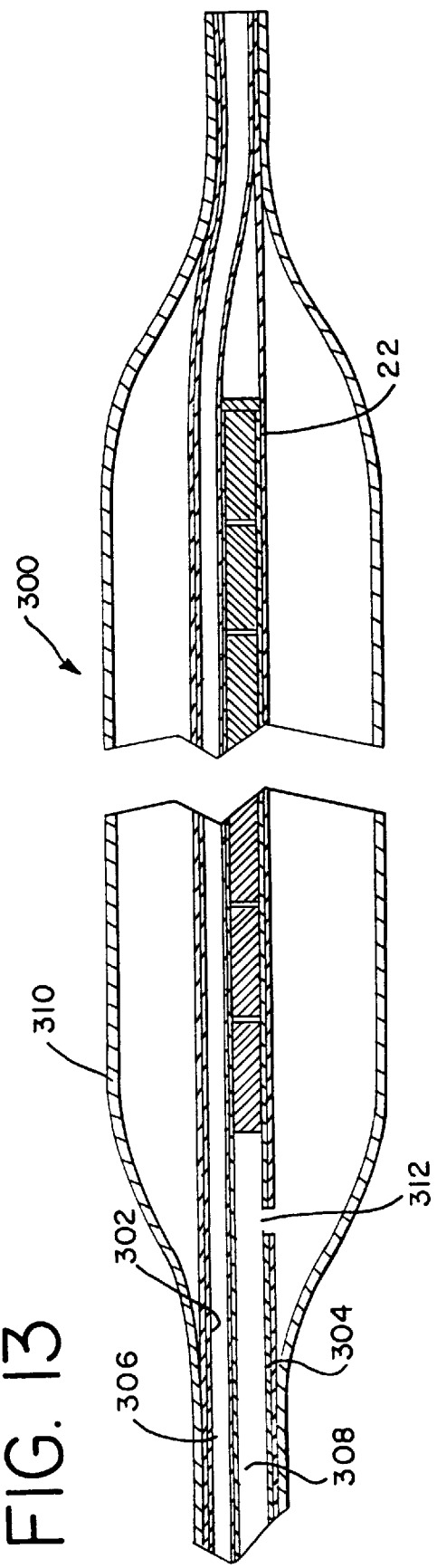
FIG. 13 is a partial cross-sectional view of a further alternative embodiment of the present invention having an inflatable balloon, with the treating elements movable along the catheter.

FIG. 13 illustrates a still further embodiment of a balloon catheter 300 which has a pair of adjacent parallel inner tubes, 302 and 304, forming guide wire lumen 306 and a treating element lumen 308. In a manner similar to FIGS. 7 and 8, the inner tubes are contained within an outer tube, and the interior space therebetween forms a return lumen. A balloon membrane 310 is bonded to the outer surface of the outer tube, forming an inflatable balloon. The balloon membrane may be inflated, through side port 312 in the wall of inner tube 304, by the same blood-compatible liquid that is used to propel the treating elements along the lumen 308. As in FIG. 12, this catheter permits expansion of the balloon membrane to carry out an angioplasty procedure within a blood vessel at the same time the treating elements are being moved to the distal end portion of the catheter (where the balloon is located) to effect radiation treatment of the tissue being subjected to the balloon angioplasty procedure.

Figure 14:
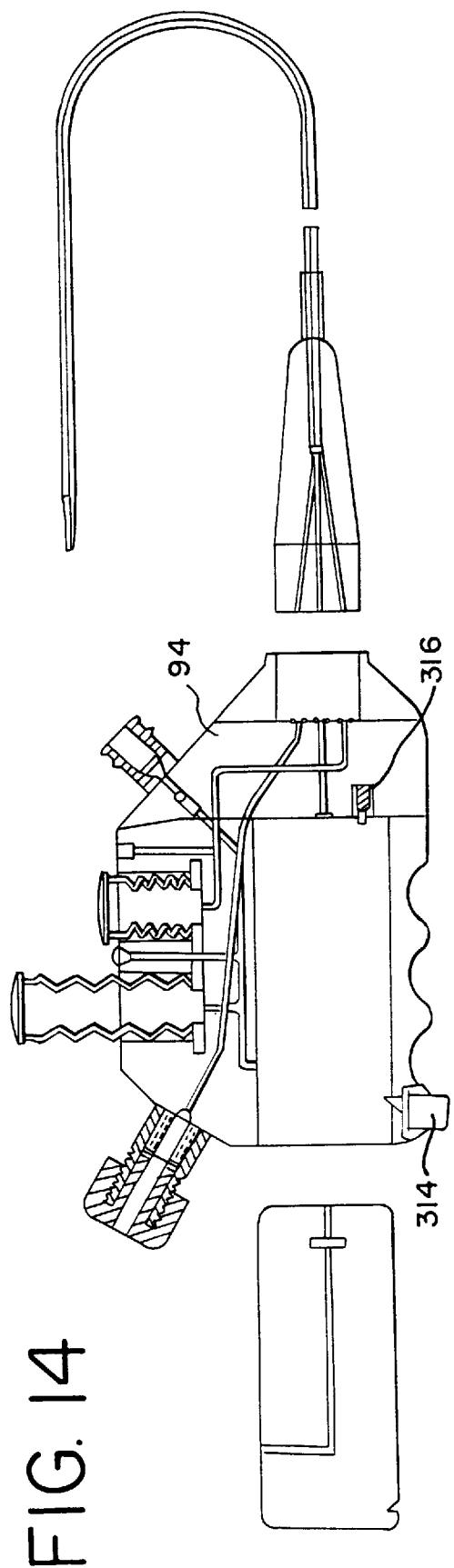
FIG. 14 is a partial cross-sectional view of another embodiment of the treatment delivery system of the present invention.

FIG. 14 shows a device that is essentially identical to that shown in FIG. 2C and described in detail earlier, except that the body member 94 includes a latch 314, such as spring loaded pin, to retain insert 110 within chamber of cavity 108. A release mechanism 316 may also be provided to release the insert.

FIGS. 15A–15C show another embodiment of treatment delivery system that is similar in many respects to the embodiment shown in FIG. 2C. In this embodiment, however, the gate 114 is in the form of a disc 318 pivotally mounted at the distal end of the insert 110. The disc includes a pair of spaced-apart apertures 320 and 322, of different sizes, therethrough, which may be moved into alignment with the center bore 112 of the insert. One of the apertures 320 is smaller in diameter than the treating elements 22, and when aligned with the bore 112 blocks the passage of treating elements from the bore while allowing liquid to pass therethrough for priming and the like. Alternatively, the disc may be pivoted to a position where the larger aperture 322 is aligned with the center bore 112, which allows the treating elements to be ejected from the insert by liquid flow pressure and advanced into and through the catheter. For shipment and storage, the disc may be positioned to fully cover the bore 112 of the insert.

In this embodiment, the body 94 includes a pair of opposed side access openings 324 for accessing the disc 318 to pivot it between the desired positions, and a pair of opposed viewing access openings 326 for visually verifying the location of the treating elements. In this embodiment, the catheter 92 has a proximal fitting 328 for attachment to the distal end of the body 94. This fitting may be keyed to assure that it is attached in the proper relationship to the body and the correct lumen of the catheter are aligned with the proper passageways of the body.

Figure 16:
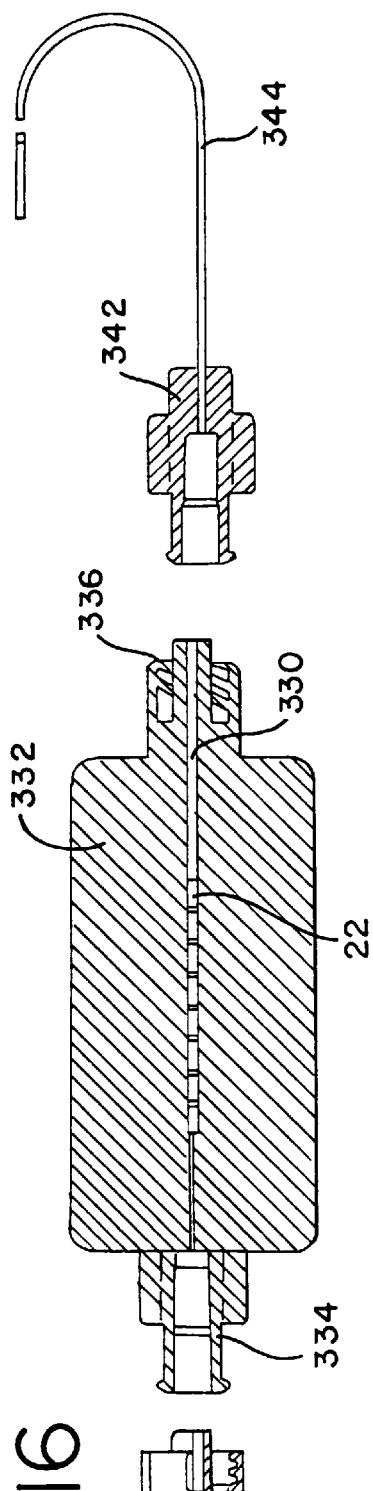
FIG. 16 is a partial cross-sectional view of various parts of a further embodiment of the treatment delivery system of the present invention.

FIG. 16 shows a simplified version of the treating system of the present invention. As shown there, the treating elements 22 are contained in a central passageway 330 of a solid body 332. Female luer lock connector 334 is provided at the inlet end of the passageway and male luer lock connector 336 is provided at the outlet end of the passageway, although a keyed fitting as described above also may be used.

During travel and storage a temporary female luer lock connector 338 is attached to the outlet connector 336. The connector 338 includes a pin 340 that extends from the connector into the passageway to hold the treating elements in place and provide a barrier against the escape of radiation. The inlet end of the passageway is smaller than the treating elements, thereby keeping the treating elements located in generally the center of the body 332.

To use this embodiment, the temporary connector 338 is removed and a female luer lock connector (or keyed connector, as discussed above) connector 342 at the proximal end of single lumen catheter 344 is attached to the outlet connector 336. A source, such as a syringe or suspended container, of blood-compatible liquid, such as saline, is attached to the inlet connector 334, and liquid is allowed to flow through the center passageway, ejecting the treating elements 22 and forcing them along the length of the catheter from the proximal to the distal end portion, which is presumable located at the site in the vascular system where treatment is desired. After the treatment is complete, the treating elements are removed by withdrawing the catheter from the patientes body or by applying a suction to the proximal end to return the treating elements by the force of reversed liquid flow.

Figure 17:
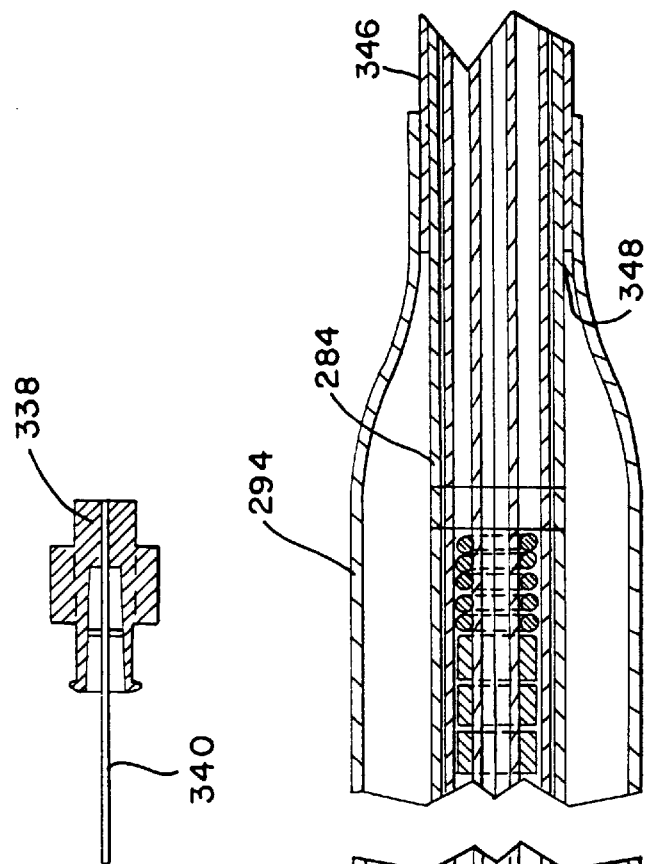
FIG. 17 is a partial cross-sectional view of another alternative embodiment of the present invention having an inflatable balloon, with the treating elements movable along the catheter.

FIG. 17 is identical to FIG. 12, except that a fourth co-axial outer tube 346 is provided over tube 284, and the end of the balloon membrane 294 is bonded to the outer tube 346 instead of the tube 284. The distal end of the outermost tube 346 terminates just inside the balloon membrane, and the space between the outermost tube 346 and the tube 284 provides an inflation lumen 348 through which pressurized fluid may flow directly into the area beneath the membrane to inflate the balloon. This construction allows a separate source of pressurized fluid to be used to inflate the balloon membrane, and inflation of the balloon membrane is not dependent on the pressure of the liquid used to move the treating elements to the distal end portion of the catheter.

Similarly, FIG. 18 is identical to FIG. 13, except that an additional tube 350 is provided over the other tubes described in connection with FIG. 13, and one end of the balloon membrane 310 is bonded to surface of the tube 350. As with FIG. 17, the space between the additional tube 350 and the tubes described earlier provides an inflation lumen 352, the distal end of which lumen opens directly in the area beneath the balloon membrane. This construction also allows a source of fluid, independent of the liquid used to move the treating elements, to be used to inflate the membrane in carrying out an angioplasty procedure.

FIG. 19 shows a still further embodiment of the distal end portion of a catheter 354 having an elongated inner tube 356 (which extends from a proximal end portion, not shown) defining an inner lumen 358. The inner tube 356 extends co-axially within an outer tube 360, the distal end of which stops short of the distal end of the inner tube. Balloon membrane 362 is attached at one end to the surface of outer tube 360 and is attached at the other end to the surface of the inner tube 356. The space between the inner and outer tubes forms an inflation lumen 364, through which liquid may be introduced to inflate the balloon.

A separate elongated catheter tube 365 is insertable into inner lumen 358 such that the distal end portion of the separate tube lies within the area of the balloon. The separate tube also has a lumen 366 extending from the proximal end (not shown) through which treating elements 22 are movable under the force of flowing liquid from the proximal to the distal end portion of the catheter (the liquid in this embodiment exits through the distal end of the lumen 358).

In keeping with a further aspect of the invention, there are seen in FIGS. 20–37 further improved embodiments of an intracoronary radiation system. As illustrated, improvements have been made to the transporting and/or loading device (herein called the transfer device), the catheter, and the interface between the two. Once again, the specific design of the fluid source may be chosen from various alternatives such as a syringe or other mechanical pump or automatic fluid injection system.

Figure 20:
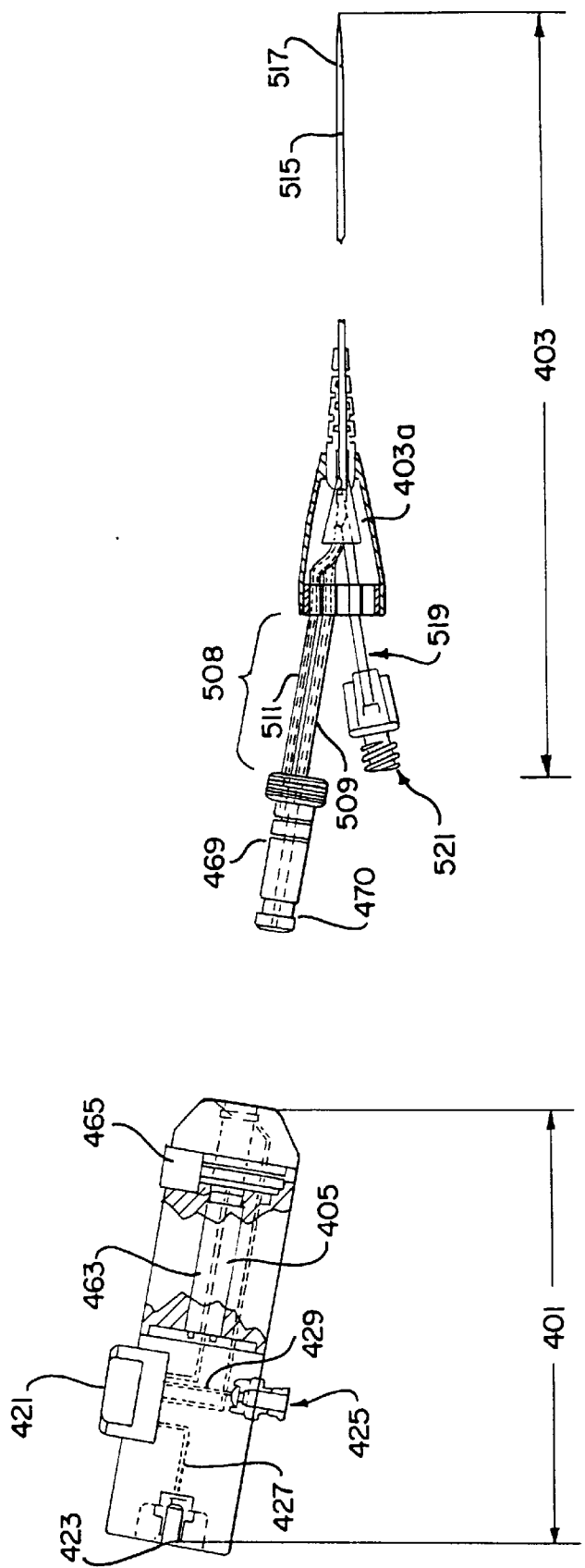
FIG. 20 is a schematic drawing of a further embodiment of an intracoronary radiation system comprising a transfer device, a radiation source train, and a delivery catheter.

As shown schematically in FIG. 20, the intracoronary radiation system comprises a transfer device, generally indicated by 401, and a delivery catheter, generally designated by 403. The transfer device 401 functions to house and shield the radiation source train, generally indicated by 405, and controls the direction of fluid flow for priming the transfer device 401 and catheter 403 to effect delivery and retrieval of the radiation elements. The radioactive source train 405 comprises two marker seeds and a plurality of radioactive treating elements or "seeds" (which are described in greater detail below). The seeds of the radioactive source train 405 may be connected together.

Figure 21A:
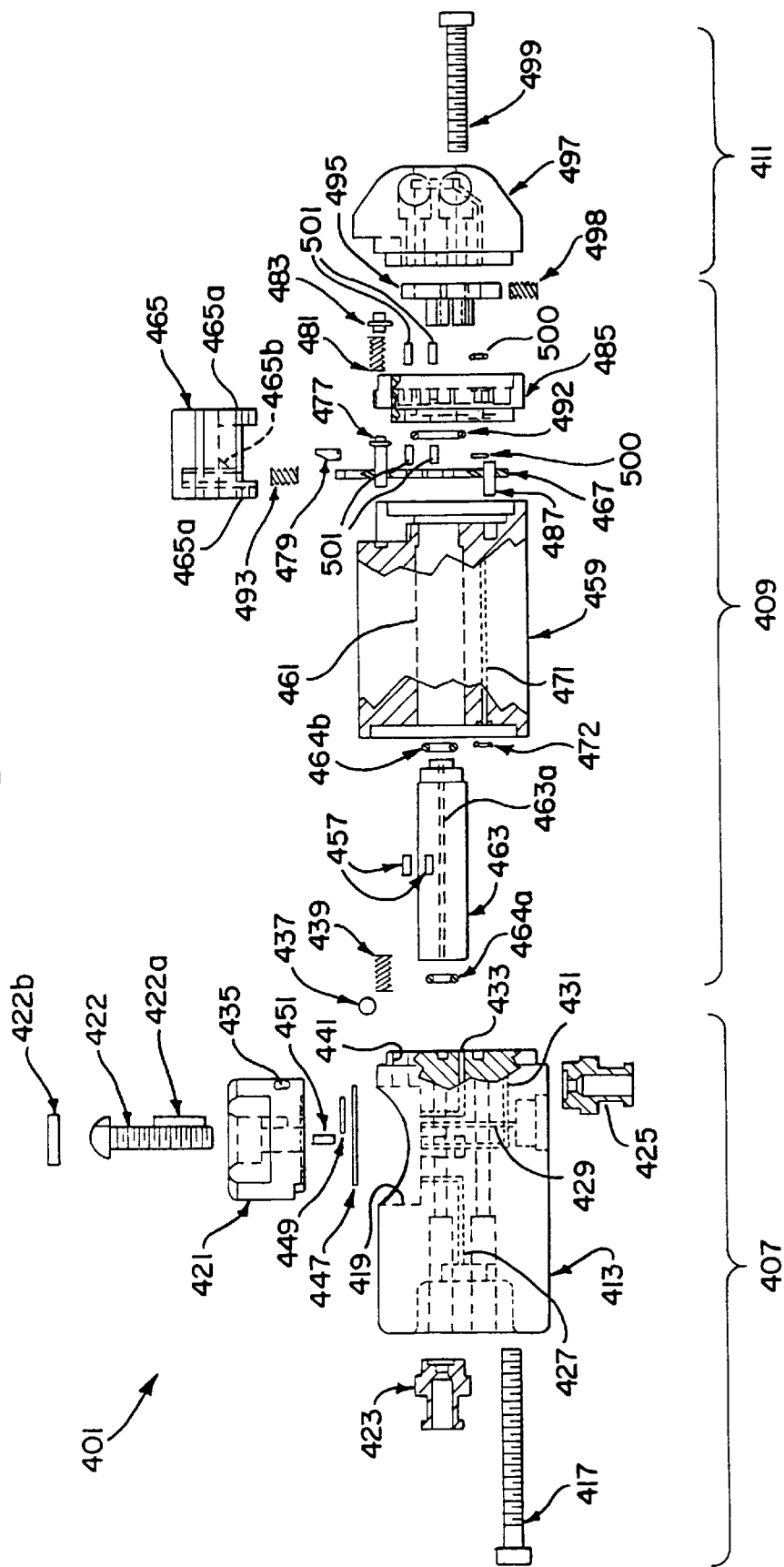
FIG. 21a is an exploded view of the transfer device of FIG. 20.
Figure 21B:
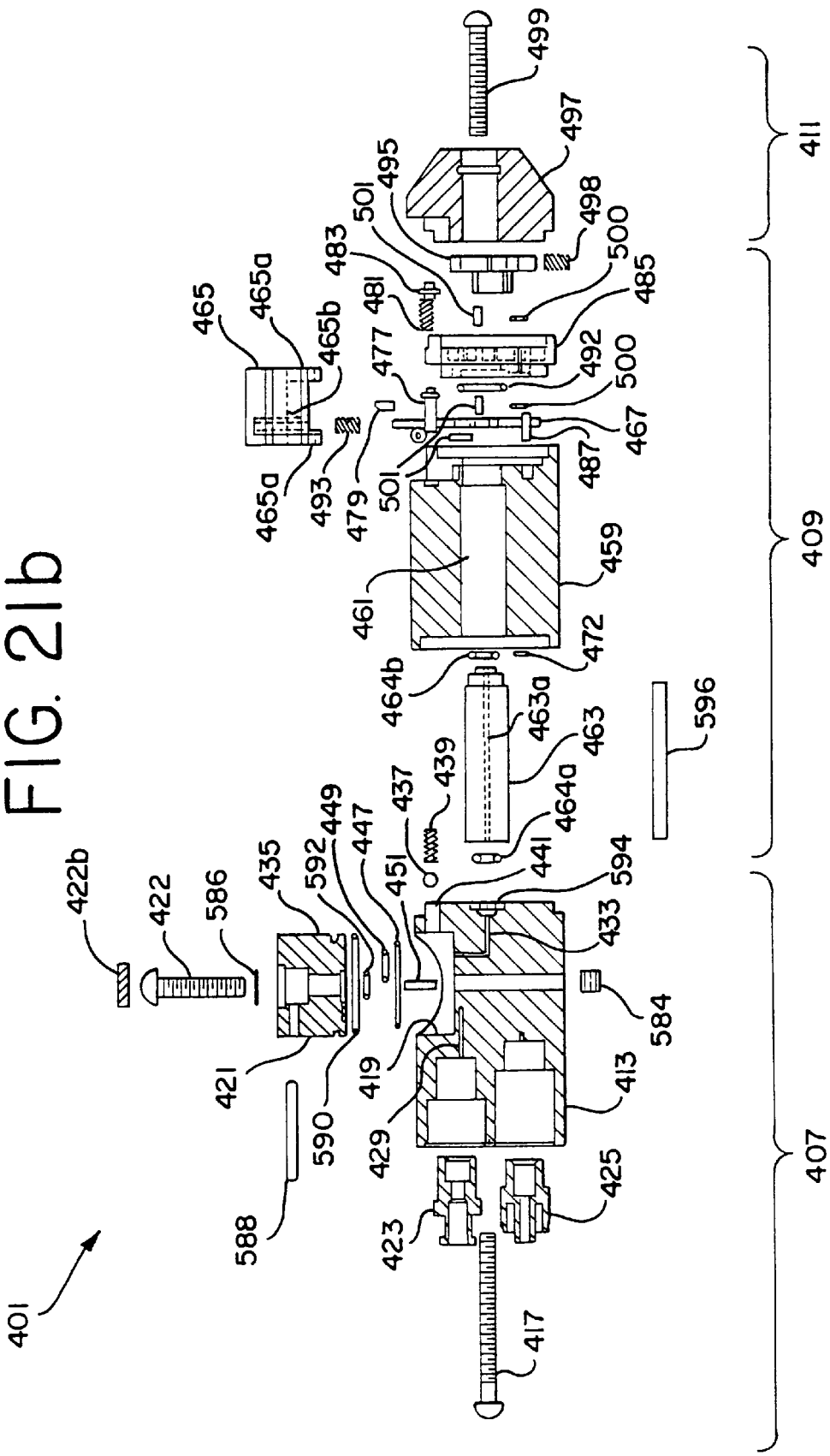
FIG. 21b is an exploded view of a further embodiment of the transfer device.
Figure 22:
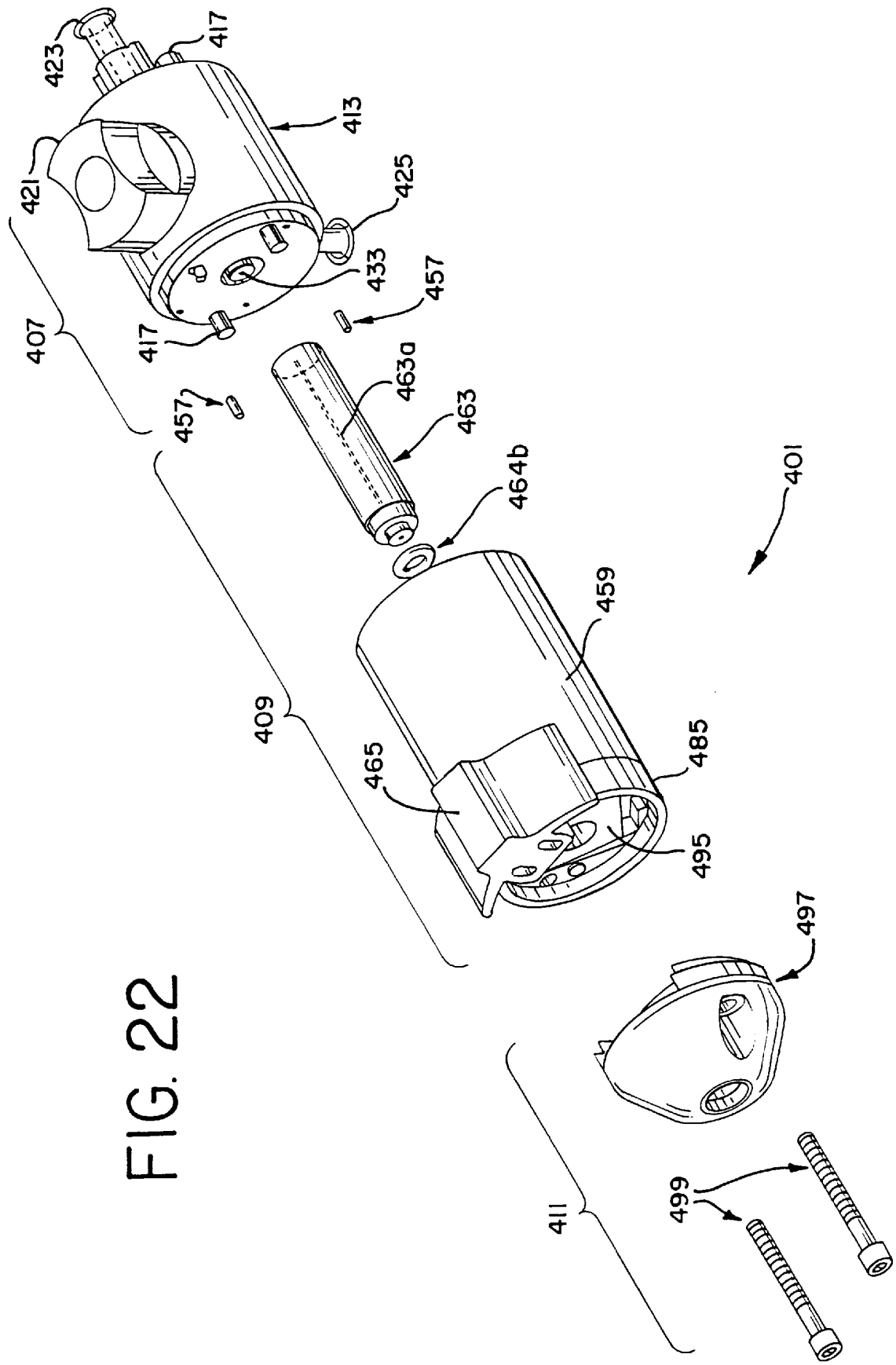
FIG. 22 is an exploded perspective view of the transfer device of FIG. 21.

The transfer device 401 is shown in exploded view in FIGS. 21a, 21b and consists of three main assemblies: rear housing and fluid control switch assembly 407, central housing and actuator switch/shuttle gate assembly 409, and front housing 411.

As best seen in FIG. 23, the rear housing 407 comprises a cylindrical member 413, preferably made of clear Lexan or clear polycarbonate. The cylindrical member 413 includes two axial through lumens 415 for positioning two stainless steel socket head screws 417 that connect the rear housing 407 to the central housing 409.

The cylindrical member 413 includes a cylindrical recess 419 for placement of the fluid control switch 421, which is discussed in greater detail below. The rear housing 407 includes two female luer fittings 423 and 425. These fittings 423, 425 may be recessed in the cylindrical member 413 and are preferably made of a polycarbonate and secured to the cylindrical member 413 by, e.g., adhesive. Luer fitting 423 is attached to the proximal end of the rear housing 407 and is in fluid communication with a fluid inlet channel 427. Luer fitting 423 connects to a liquid or gas filled device (not shown) that is used for hydraulic or pneumatic delivery and retrieval of the radiation source train 405.

Luer fitting 425 may be attached to the bottom of the rear housing 407, as seen in FIG. 21a, or may be attached to the proximal end of the rear housing 407, adjacent to luer fitting 425, as can be seen in FIG. 21b. Luer fitting 425 is in fluid communication with the fluid exit channel 429 and can optionally be connected to a fluid collection bag or reservoir (not shown). The cylindrical member 413 also includes a hydraulic return channel 431 and a seed delivery channel 433. Each of the channels 427, 429, 431, and 433 communicate with the cylindrical recess 419.

The fluid control switch 421 selectively provides access between the various channels 427, 429, 431, and 433 to introduce and/or retrieve the radioactive treatment elements and the marker seeds from the delivery catheter 403. The fluid control switch 421, which is preferably made of black Lexan or black Acetal, is generally cylindrical and has two curved portions removed from the top half of opposing sides of the switch 421 to facilitate easy manipulation of the switch. To further facilitate easy manipulation of the switch 421, the distal end of a pin arm 588 is press fitted within an opening in the fluid control switch 421. Utilizing pin arm 588 to maneuver the switch 421 provides for increased torque. A retention screw 422 extends through a central bore in the switch 421 and a bore in cylindrical housing 413 to secure the switch 421 to the cylindrical member 413. The head of the retention screw 422 is notched so that a locking pin 422a may fit through it. The locking pin 422a prevents rotational movement of the retention screw 422 so that counterclockwise movement of the fluid control switch 421 will not loosen the screw 422. It is received in a shallow hole drilled in an annular seat in the fluid control switch 421 where the head of the retention screw 422 rests. A locking cap 422b closes the central bore in the switch 421. Alternatively, to prevent rotational movement of the retention screw 422, a set screw 584 is fitting within the bore of the cylindrical housing 413 for binding with the retention screw 422 once the retention screw 422 has been extended through the central bore and washer 586 in switch 421 and the bore of the cylindrical housing 413.

In order to limit the degree to which the fluid control switch 421 can be rotated, the bottom of the switch 421 includes a fluid control slot 453 and a cooperating alignment pin 451 is secured in hole 451a in the recessed area 419 of the rear housing member 413. Optionally, the recessed area 419 of the rear housing may include the fluid control slot 453 and the cooperating alignment pin 451 can be secured within a hole in the bottom of the fluid control switch 421. The fluid control switch 421 also includes three dimples 435 that interact with a detent ball 437 and compression spring 439 to positively locate the switch in "roff", "send", and "ore-turn" positions. The detent ball 437 and compression spring 439 are housed in a short lumen 441 within the cylindrical member 413.

As best seen in FIG. 24, the bottom of the fluid control switch 421 includes a C-shaped connector channel 443 and an elliptical-shaped connector channel 445. The control switch 421 is relieved about the C-shaped and elliptical-shaped connector channels 443, 445 in order to receive O-rings 447 and 449, respectively, which seal the connector channels 443, 445 against the recess 419. To further prevent leakage around fluid control switch 421, an O-ring 590 may be received by an O-ring channel about exterior of the fluid control switch 421, and an O-ring 592 may be received by an O-ring channel about the distal opening of switch 421. The O-rings 447, 449, 590 and 592 are preferably made of Buna-N. Alternatively the O-rings 447, 449, 590 and 592 (as well as all other O-rings described herein) can be made of ethylene propylene; which has less of a tendency to swell during the sterilization process.

In operation, when the fluid control switch 421 is in the "send" position, both the fluid injection channel 427 and the seed delivery channel 433 communicate through the C-shaped connector channel 443. Simultaneously, the hydraulic return channel 431 and the fluid exit channel 429 communicate through the elliptical-shaped connector channel 445. Thus, fluid is allowed to flow through the fluid injection channel 427 through the C-shaped connector channel 443 and into the seed delivery channel 433. Fluid that bypasses the treating elements reaches the distal end of the delivery catheter 403 and returns to the hydraulic return channel 431 and is allowed, through the elliptical-shaped connector channel 445, to flow through the exit channel 429.

When the fluid control switch 421 is in the "return" position, both the fluid injection channel 427 and the hydraulic return channel 431 are aligned through the C-shaped connector channel 443. Simultaneously, both the seed delivery channel 433 and the fluid exit channel 429 are aligned through the elliptical-shaped connector channel 445. Consequently, fluid is allowed to flow through the fluid injection channel 427 into the C-shaped connector channel 443 and through the hydraulic return channel 431. As the treating elements and marker seeds are forced hydraulically from the distal end of the catheter 403 back to the transfer device 401, fluid is allowed to flow from the seed delivery channel 433 to the fluid exit channel 429 through the elliptical-shaped connector channel 445.

Figure 25:
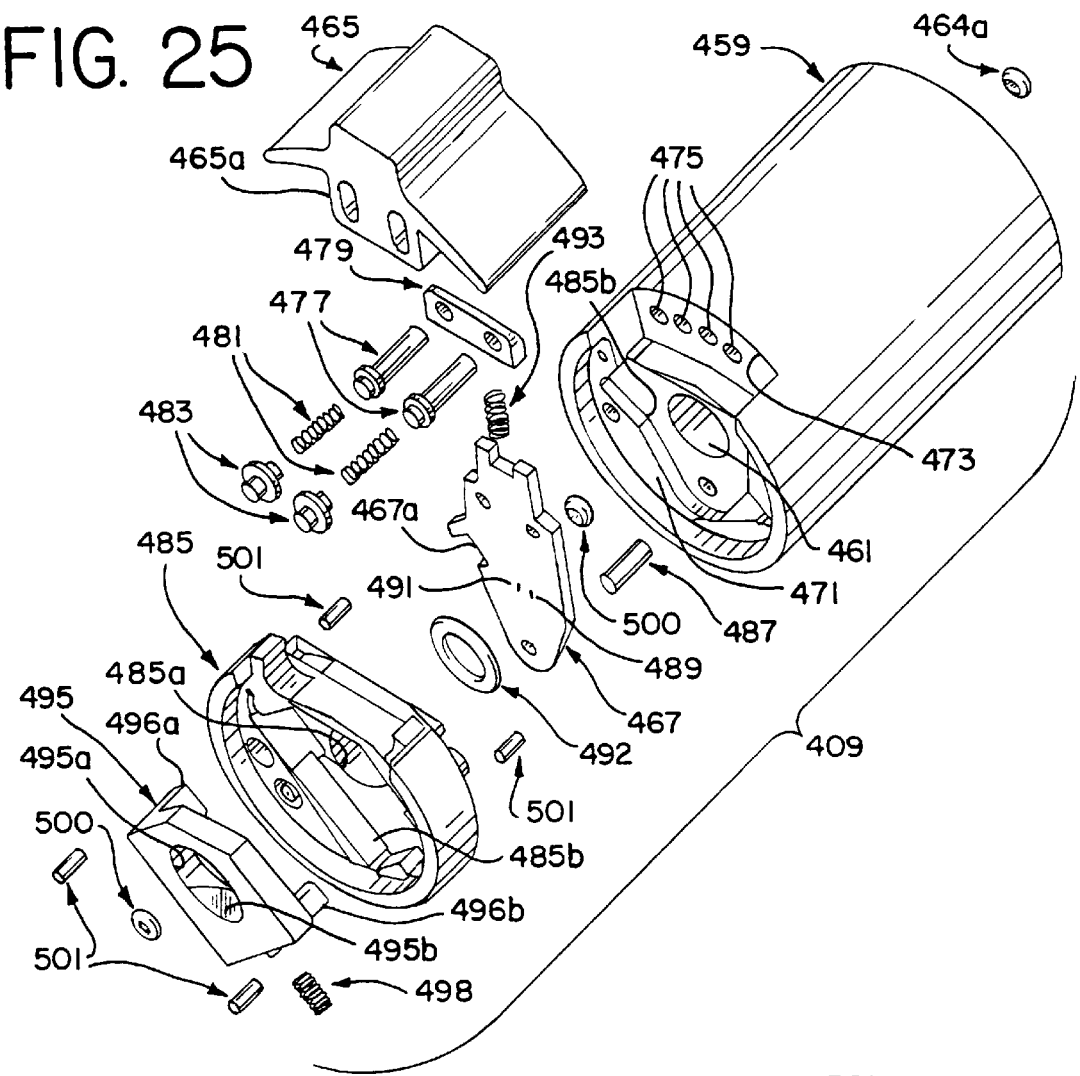
FIG. 25 is an exploded perspective view of the central housing and actuator switch assembly for the transfer device of FIGS. 21 and 22.
Figure 26A:
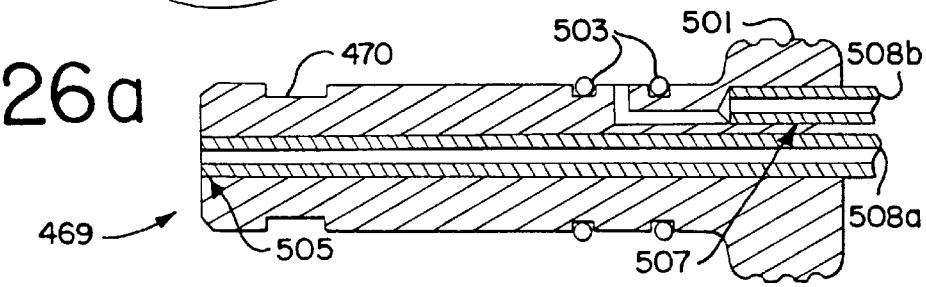
FIG. 26a is a cross sectional view of a connector for the intracoronary radiation system of FIG. 20 that connects the transfer device to the delivery catheter.
Figure 26B:
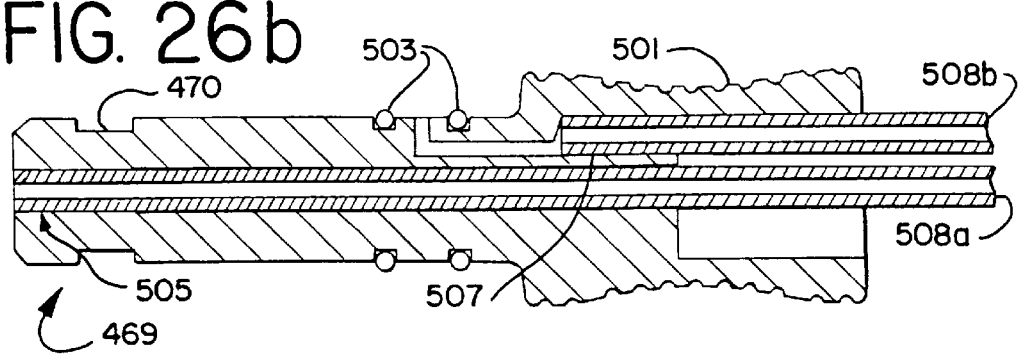
FIG. 26b is a cross sectional view of an alternate embodiment of a connector for the intracoronary radiation system of FIG. 20 that connects the transfer device to the delivery catheter.

When the fluid control switch 421 is in the "off" position, the fluid injection channel 427 is the only channel aligned with the C-shaped connector channel 443. Thus, no outlet exists for fluid flowing into the connector channel 443 from the fluid injection channel 427. Distal of the rear housing 407 and connected thereto is the central housing and actuator switch/shuttle gate assembly 409. Proper alignment of the rear housing 407 and central housing and actuator switch/shuttle gate assembly 409 is assured by alignment pins 457. As best seen in FIG. 25, the assembly 409 includes a central housing 459 having a central lumen 461 for receipt of a quartz sleeve 463 (FIGS. 21, 22) in which the radiation source train or seeds 405 are stored. An actuator switch 465 is located at the distal end of the central housing 459 that pivots a shuttle gate 467 to operate the system.

Specifically, the actuator switch 465 allows for three positions. "connect/prime", "seed transit", and "release". If a separate release button is included, then the actuator switch may allow for only the connect/prime position and the seed transit position. The connect/prime mode allows for the connection of a connector 469 (best seen in FIGS. 20, 26, and 27 discussed in greater detail below) to the transfer device 401. After connected, the connect/prime mode allows for flushing and priming of the transfer device 401 and the catheter 403 without the delivery of the radiation source train 405.

The seed transit mode allows for the delivery of the radiation source train 405 to, and retrieval from, the distal end of the catheter 403. The seed transit mode of the actuator switch 465 cannot be accessed unless the connector 469 has been locked into the transfer device 401. This prevents inadvertent delivery of the radiation source train to any location other than the delivery catheter 403.

The release mode permits the removal of the connector 469 from the transfer device 401. In order to prevent accidental removal of the delivery catheter 403 from the transfer device 401 prior to the completion of the treatment procedure, the release mode is spring loaded and must be held in position while removing the connector 469.

Turning again to FIG. 25, the central housing 459 is cylindrical in shape and preferably made of clear Lexan or clear polycarbonate. A central through-lumen 461 houses the quartz sleeve 463, which is preferably made of natural or synthetic quartz or quartz glass (fused quartz) or other material consisting of natural or synthetic fused silica, and has a lumen extending the entire length thereof, designated by 463*a*. The radiation source seeds are stored within the lumen 463*a* when the seeds are not being delivered to the treatment site. In order to more easily discern the presence of the radiation source seeds within the quartz sleeve 463, the lower half of the sleeve 463 can be covered with a white film 596, preferably vinyl or Tyvek®, to create a contrasting background for the source seeds. Care should be taken not to obscure the top view of the radiation seeds. Additionally or alternatively, a magnifying piece (not shown) may either encase the quartz sleeve 463, or lie along or be embedded in the top of the quartz sleeve 463, to permit better visualization of the radiation source seeds and marker seeds. The quartz sleeve 463 is used to shield the radiation emitting from the radiation source train so that the transfer device 401 can be handled safely. The quartz material does not break down as a result of storing the radiation-emitting treatment seeds and also remains clear so that the seeds can be visually detected. The quartz rod is of sufficient thickness to block at least 99% of the radiation. In practice, a thickness of 1 cm has been found to be sufficient. To provide a seal for the prevention of fluid leaks, O-ring 464*a* fits within an annular slot at the distal end of the rear housing 407, while O-ring 464*b* is located at the distal end of the quartz sleeve 463. As seen in FIG. 21*b*, a rear housing insert 594 with a lumen therethrough may be added as an intermediate member for providing fluid communication between the seed delivery channel 433 and the lumen 463*a* of quartz sleeve 463. The lumen of the rear housing insert is sufficiently small in diameter such that the treating elements cannot pass through it and enter into the rear housing 407.

A smaller, off-axis, through-lumen 471 extends through the central housing 459 and is a continuation of the hydraulic return lumen 431 in the rear housing 407. Fluid leakage between the connection of the return lumen 431 in the rear housing 407 and the return lumen 471 in the central housing 459 is prevented by means of an O-ring 472, preferably made of Buna-N. The central housing 459 is recessed to receive the actuator switch 465 at 473. Four shallow holes 475 are machined in the recessed area 473 of the central housing that receive positioning pins 477 to positively lock the actuator switch 465/shuttle gate 467 in position for one of the three modes discussed above.

If the "release" mode is spring loaded, there are four positioning pin holes 475. The positioning pins 477 rest in the second and fourth holes when the actuator switch is in the "connect/prime" mode. In the "seed transit" mode, the positioning pins 477 rest in the first and third holes. In the "release" mode, the positioning pins 477 do not rest within any of the holes. One of the positioning pins 477 is aligned with the third or fourth hole, but the other positioning pin aligns with the solid portion past the fourth hole. The solid portion stops movement of the positioning pins 477 so that they cannot engage with either of the holes. Once it is no longer forced towards the "release" mode, the actuator switch 465 is biased by the spring and returns to the "connect/prime" mode, where the positioning pins 477 rest in the second and fourth holes.

Alternatively, there can be five positioning pin holes 475, in which case the pins rest in the second and fourth holes for the "connect" mode, the first and third holes for the "seed transit" mode, and the third and fifth holes for the "release" mode, with the actuator switch 465 locking into place for the "release" mode.

In practice, the positioning pins 477 are inserted into a sliding plate 479 made of Delrin. The sliding plate 479 has a beveled side and two through holes that receive the pins 477. The sliding plate 479 is oriented beveled-side up between two legs of the actuator switch 465. The positioning pins 477 are biased into position by compression springs 481. One end of each compression spring 481 rests on the head of a positioning pin 477 while the other end rests on the head of an engagement pin 483. The shuttle gate 467, sliding plate 479, positioning pins 477, compression springs 481, and the engagement pins 483 are maintained in proper position between the proximal and distal legs of the actuator switch 465.

The actuator switch 465 is made of a hard plastic material, such as Delrin or Acetal, and has a generally rectangular mid-section with two curved arms extending outwardly and downwardly therefrom to provide a nob-like section for grasping by the user. Extending below the nob-like portion are two rectangular legs 465*a* having elongated holes drilled therethrough for receipt of the engagement pins 483 in the distal leg and positioning pins 477 in the proximal leg. Also extending from the bottom of the actuator switch 465 between the rectangular legs 465*a* is an angled projection 465*b* (FIG. 21) that mates with the sliding plate 479 when the actuator switch 465 is depressed.

Also secured to the positioning pins 477, and thus the actuator switch 465, is the shuttle gate 467. The shuttle gate 467 is pivotally attached to the central housing 459 by an axis pin 487. The shuttle gate 467 also includes a seed hole 489 and a prime/flush hole 491. The seed hole 489 is large enough to allow the radioactive elements to pass therethrough and is positioned so that it aligns with the through-lumen of the quartz sleeve 463 only when the actuator switch 465 is in the "seed transit" mode. The prime/flush hole 491 is sized small enough so that it does not permit the radioactive elements to pass therethrough. Prime/flush hole 491 is adjacent to the seed hole 489 and aligns with the through lumen of the quartz sleeve 463 only when the actuator switch 465 is in the connect/prime mode. Thus, fluid will pass through the prime/flush hole 491, but the seeds will not. An O-ring 492, preferably made of Buna-N, prevents leakage between the seed hole 489 and prime/flush hole 491 of the shuttle gate 467 and the connector 469.

Alternatively, the shuttle gate 467 could have a single hole that, depending upon its position, would allow the passage of either only fluid (the actuator switch 465 being in the connect/prime mode) or fluid and treatment seeds (the actuator switch 465 being in the seed transit mode).

A compression spring 493 biases the actuator switch 465 away from the shuttle gate 467. When the actuator switch 465 is pressed downward against the force of the compression spring 493, the angled projection 465b on the underside of the switch 465 engages the beveled side of the sliding plate 479 to force the sliding plate 479 and positioning pins 477 toward the distal end of the transfer device 401. The positioning pins 477 are thus moved out of engagement with the positioning holes 475 to permit movement of the actuator switch and shuttle gate to the various modes.

The assembly of the actuator switch 465 and shuttle gate 467 is configured so that the actuator switch 465 may be moved from one mode to another only when the connector 469 is locked into place. To this end, a collar housing 485 holds a collar 495. A front housing 497 located at the distal part of the transfer device 401 (FIGS. 21, 22) functions to secure the collar 495 and collar housing 485 to the central housing 459 by means of socket head screws 499. Alignment of the front housing 497, collar 495, and collar housing 485 (as well as the central housing 459) is insured by alignment pins 501. O-rings 500, preferably made of Buna-N, are located on opposite sides of the collar housing to prevent fluid leakage from the return channel. While the collar housing 485 and front housing 497 are preferably made of clear Lexan, the collar 495 is preferably made of white Delrin.

The collar housing 485 and the collar 495 both have cylindrical through-holes 485a and 495a, respectively, which are sized to receive the connector 469. The through-hole 495a in the collar 495 also has a sloped relief 495b of a parabolic shape on the distal face of the collar 495. The collar 495 also includes two legs 496a and 496b that extend from the proximal phase of the collar that are slidingly received within two hollow areas in the collar-shaped recessed area 485b of the collar housing 485. A compression spring 498 biases the collar 495 so that the central hole 495a does not normally align with either the central hole 485a in the collar housing 485 or the central lumen of the front housing 497.

The connector 469 works together with the collar 495/collar housing 485 and the shuttle gate 467 as follows. Before the connector 469 is inserted into the transfer device, the leg 496a of the collar 495 is positioned to prevent the shuttle gate 467 from pivoting in the direction for the seed transit mode. When the connector 469 is inserted into the transfer device, the proximal tip of the connector 469 contacts the sloped relief 495b of the collar 495 to slide the collar against the force of the compression spring 498. The leg 496a moves against a niche 467a at the edge of the shuttle gate 467, still inhibiting movement of the shuttle gate so that it cannot be positioned in the seed transit mode, but allowing the connector 469 to slide through the through-hole 495a of the collar 495 and through-hole 485a of the collar housing 485.

The connector 469 includes an undercut area 470 (FIG. 26). Once this undercut area 470 is inside the through-hole 495a of the collar 495, the compression spring 498 forces the collar to slide in the reverse direction so that the wall of the through-hole 495a of the collar 495 comes into contact with the undercut area 470. In this position, the through-hole 495a of the collar 495 is no longer in alignment with the central lumen 461 of the housing 459. The connector 469 is now completely locked into the transfer device and cannot be removed when the actuator switch is in either the connect/prime mode or the seed transit mode. The leg 496a also no longer blocks the pathway of the shuttle gate 467 and it can be positioned in either the connect/prime or seed transit mode.

To release the connector 469, the actuator switch is moved to the release mode in which the shuttle gate pivots so that it hits leg 496b of the collar 495, forcing the collar to move against the force of the spring 498 and disengage the edge of the through-hole 495a of the collar 495 from the undercut 470 in the connector 469. The through-hole 495a of the collar 495 then moves into alignment with the through-hole 485a of the collar housing 485 and the central lumen of the front housing 497, allowing the connector 469 to be disconnected by pulling it out of the transfer device.

The connector 469 functions to connect the delivery catheter 403 to the transfer device 401 so that the lumens of the catheter are aligned with the appropriate channels of the transfer device. In practice, the connector 469 is made of clear polycarbonate and includes a handle portion 501 (best seen in FIGS. 26a, 26b) which may be corrugated so as to produce a non-slip surface. The connector is undercut in two places as indicated by 503 to allow for the proper positioning of two O-rings. The connector 465 includes a seed lumen 505 and a fluid return lumen 507.

Figure 38:
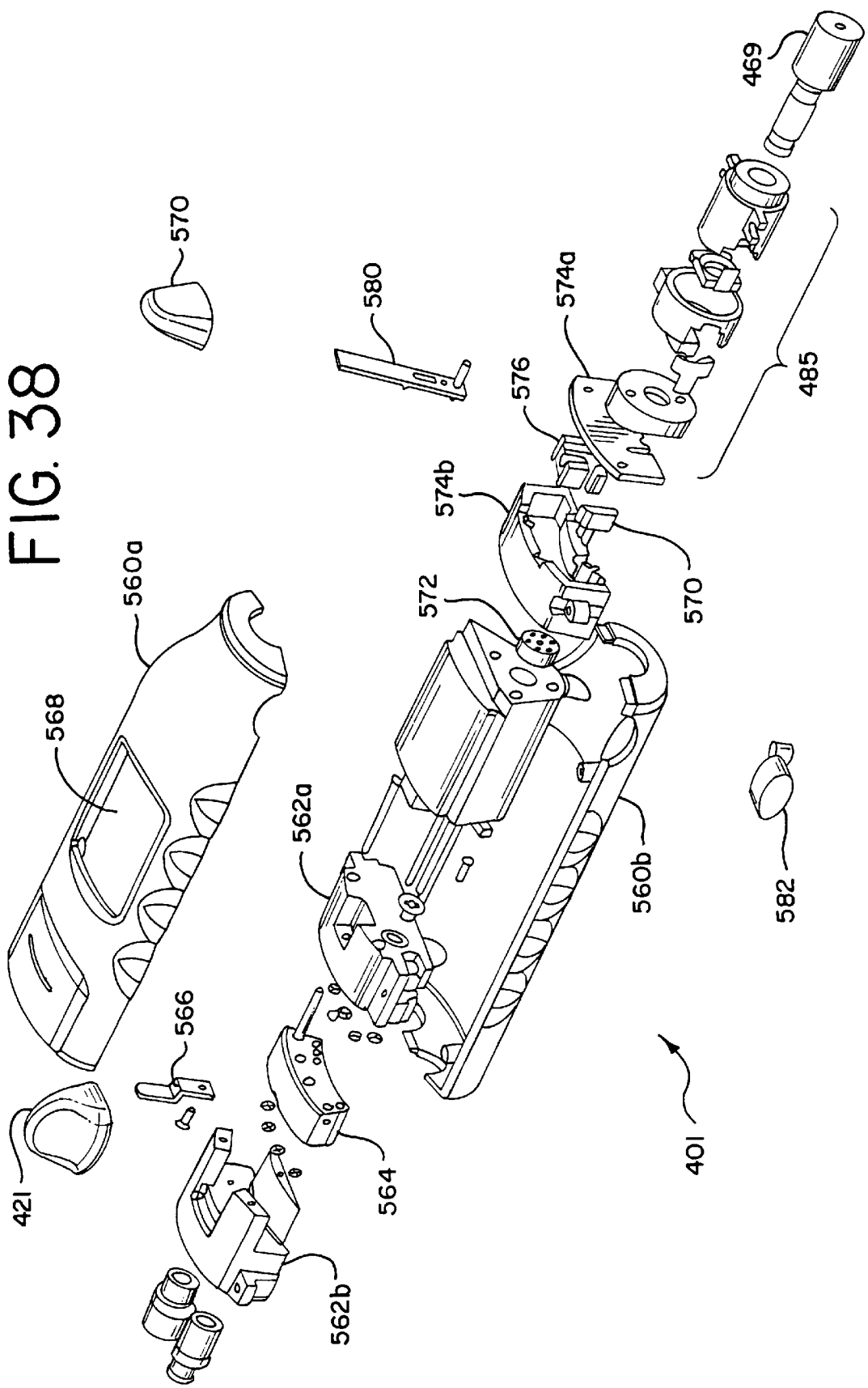
FIG. 38 is an exploded perspective view of a further embodiment of a transfer device according to the present invention.

Turning to FIG. 38, there is seen an alternate embodiment of a transfer device 401 in which the rear housing, central housing, and front housing are combined to form a single unit with an upper housing 560a and lower housing 560b. With identical reference numerals being used for similar structure, the housing members 560a, 560b encase a fluid control switch assembly 407 comprising a front and rear manifold, 562a, 562b, respectively, that encase a fluid control valve 564. A control lever 566 is operatively connected to the fluid control switch 421 to control fluid flow. As illustrated in FIG. 38, the fluid control switch 421 controls the position of the fluid control valve by sliding motion, rather than rotational motion. Correctly positioning the fluid control switch 421 allows one to align the fluid control valve 564 with the desired lumen of the front manifold 564a.

Downstream of the fluid control valve 564 is a quartz sleeve 463 that houses the radiation source train. A view port 568 in the upper housing member 560a permits visual verification of the source train when it resides within the quartz sleeve 463.

At the distal end of the quartz sleeve is an alternate design of an actuator switch 570 that functionally corresponds to the actuator switch 465 described above. However, in the embodiment illustrated in FIG. 38, the actuator switch 570 operates in conjunction with a soft gate 572 (or, alternatively, a pin gate—not shown) mounted to a two-part gate mechanism housing 574a, 574b. The soft gate 572 is cylindrical, made of an elastomeric material, and includes a seed lumen therethrough. The seed lumen within the gate 572 is sufficiently small in diameter so that the seeds cannot pass through it. The soft gate 572 designed to protect a treating element if it should accidentally be left within the pathway of the gate when an attempt to close the gate is made.

Contained within the housing 574a, 574b are a sliding ramp 576 and a spring assisted plunger 578, which are manipulated by means of the gate lever 580 and actuator switch 570. As the gate lever 580 of the soft gate 572 is pressed downward and to one side by the actuator switch 570 ("open gate model") the sliding ramp 576 maneuvers the plunger 578 (hollow pin) forward toward the proximal end of the transfer device so that it enters the centered lumen within the soft gate 572. The plunger completely fills the lumen of the soft gate and is of a large enough diameter that the seeds can pass therethrough. As the gate lever 580 is released ("closed gate mode"), the compressed spring expands, disengaging the plunger 578 from the soft gate seed lumen and sending it and the sliding ramp back to their original positions. The seed lumen of the gate 572 reduces to its original diameter and the seeds can no longer pass through the gate.

Alternatively, if a pin gate is used instead of a soft gate, as the gate lever of the pin gate is pressed downward and slid to one side ("open gate mode"), a rotating shaft with an eccentric rotation (i.e, a cam) and seed lumen therethrough is rotated so that the pin no longer occupies any part of the seed lumen. The seeds can now be delivered to the distal end of the catheter. As the gate lever is released ("closed gate model"), the rotating shaft is rotated so that the pin fully occupies the lumen and prevents delivery of the seeds. The pin does not, however, prevent fluid flow. Also, the pin gate includes a leaf spring which controls the force with which the pin moves. If a seed is in the pathway of the pin gate and an attempt is made to close the gate, the seed will not be damaged as a result of the leaf spring's control over the pin. Upon contact with the seed, the pines motion will be halted, leaving the seed undamaged.

Downstream of the actuator switch 570 is a collar mechanism, indicated by 485. The collar mechanism is similar in function to the collar assembly shown in FIG. 25 in that it receives the connector 469 to secure the catheter (not show) to the transfer device. Neither the pin gate nor the soft gate can be positioned in the "seed transit mode" unless the connector 469 has been fully inserted and locked into the front housing of the transfer device.

A separate release button 582 may be included for disengaging the connector 469 from the transfer device. To prevent seeds from inadvertently being displaced from the transfer device, the release button 582 can only be activated when the gate 580 is in a closed position. Any attempt to activate the release button 582 when the gate 580 is in the "seed transit" mode will not be successful. When the gate 580 is positioned to the "seed transit" mode, the collar mechanism 485 rotates such that the connector 469 cannot be disengaged from the transfer device.

The actuator switch 570 and the connector release button 582 may be positioned in relation to one another such that the actuator switch 570, when being positioned in the "seed transit" mode, slides over the release button 582 making it inaccessible while the gate 580 is opened.

Figure 39:
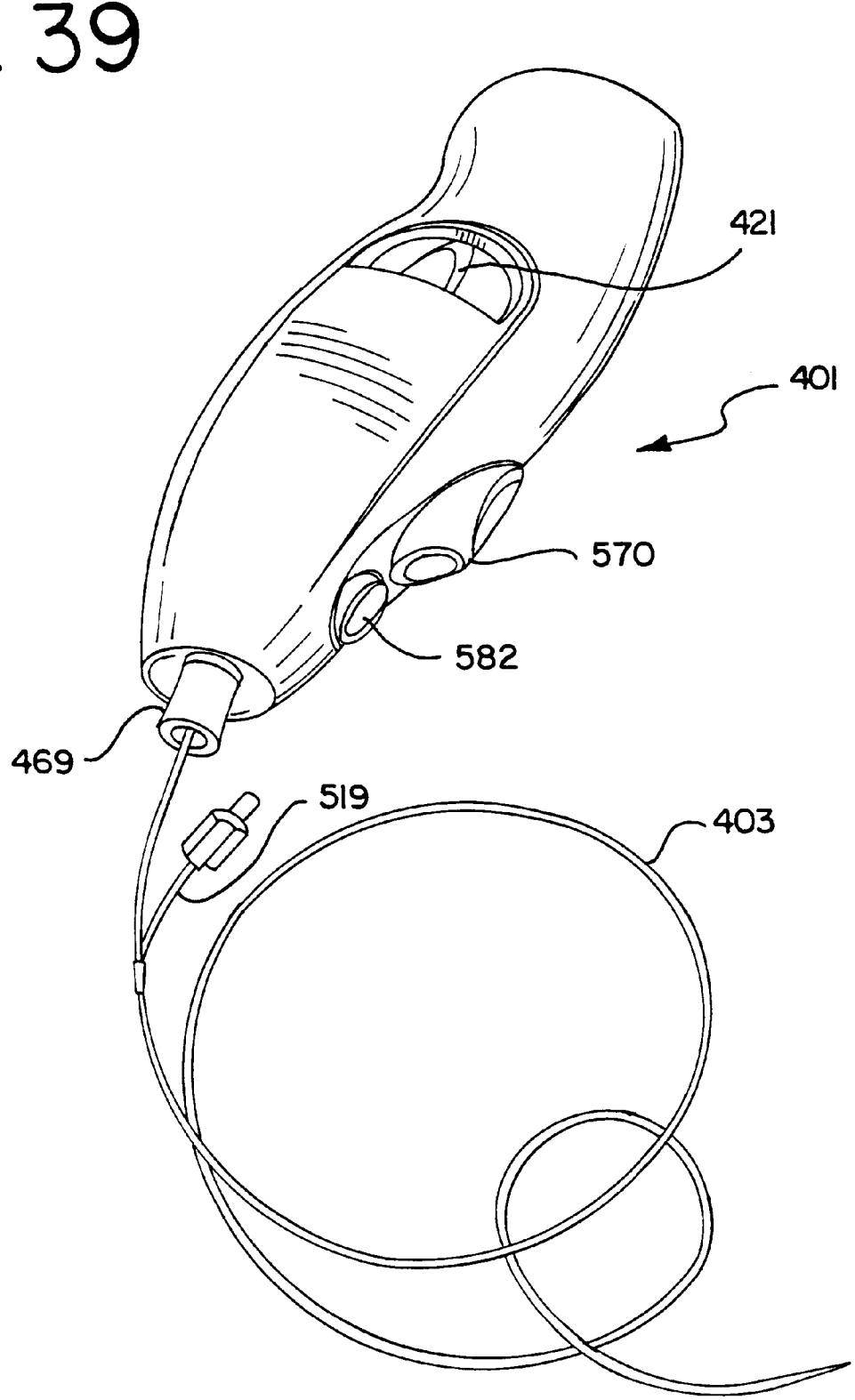
FIG. 39 is a perspective view of a further embodiment of an intracoronary radiation system comprising a transfer device and a delivery catheter.

As can be readily appreciated, the interior configuration of the transfer device is dictated by the mechanical functions of its various components. However, the exterior can be ergonomically configured, as shown in FIG. 39, to be more comfortably held in the operator's hand.

Figure 27C:
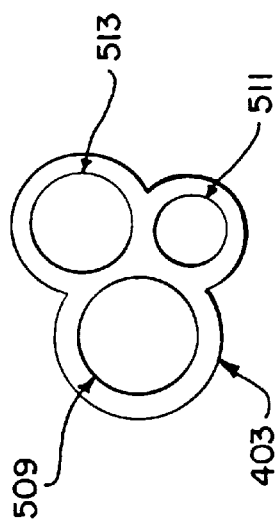
FIG. 27c is an enlarged cross-sectional view of an alternate embodiment of a delivery catheter.
Figure 27B:
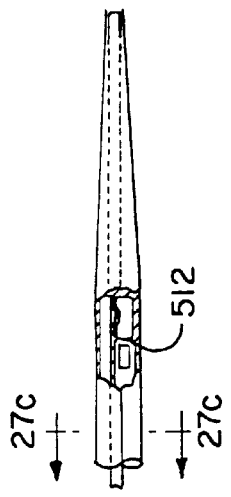
Figure 27A:
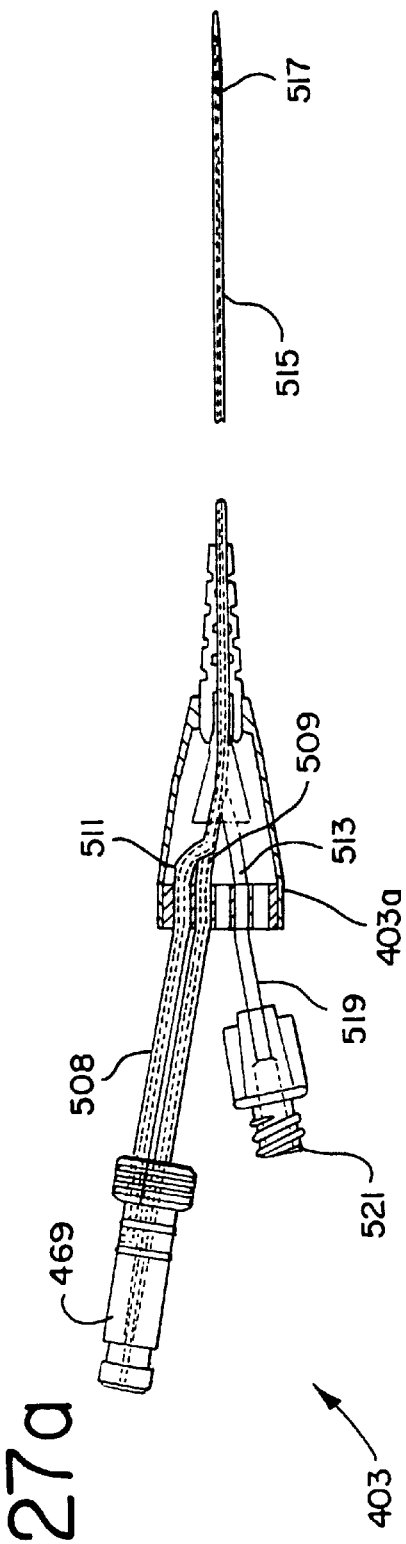
FIG. 27a is a plan view in partial cross section of the delivery catheter of FIG. 20 with the connecter of FIG. 26 attached.

Distal of the connector 469 is the catheter 403. Similar to the catheters discussed above, catheter 403 has three lumens: a seed lumen 509, a fluid return lumen 511, and a guide wire lumen 513 (FIG. 27). Similar to the catheter illustrated in, e.g., FIG. 5, the seed lumen 509 and fluid return lumen 511 communicate at the distal end of the catheter through an interluminal connector 512 (best seen in FIG. 27b). The connector 512 is preferably made of stainless steel tubing and is located in the seed lumen 509 to also serve as a barrier that stops the treating elements from advancing further within the catheter.

As illustrated (FIGS. 20, 27a), the catheter 403 communicates with the connector 469 by means of an extension 508. The extension 508 comprises two separate tubes 508a, 508b having lumens that align with the seed and fluid return lumens 505 and 507, respectively, in the connector 469. As illustrated, the extension tube 508a fully lines the seed lumen 505, while the extension tube 508b partially lines the fluid return lumen 507. The extension 508 is preferably made of Tecoflex Ea-100A resin and is connected at its distal end to the delivery catheter 403 through an optional trifurcation housing 403a in which each of the seed, fluid return, and guide wire lumens 509, 511 and 513 converge. A catheter 403 without a housing for its trifurcation is shown in FIGS. 36a, 36b. Instead, a heat shrinkable sleeve 403b encloses the junction of the various lumens 509, 511, 513 to provide added strength.

The catheter 403 is preferably made in a single extrusion of Pebax 5533-SA-00 with a matte finish to reduce frictions Alternatively, Besno Pebax blends, Hytrel, or a material resistant to gamma sterilization, such as polyolfin, could be used. The material is uniform along the entire length of the catheter body, including the tip. As best seen in FIGS. 27c, the outside of the catheter 403 can be in the shape of a three-leaf clover, rather than cylindrical. This results in the catheter 403 having less "dead" space than a cylindrical three lumen catheter and will also permit more blood to perfuse past the catheter when in use.

The guide wire lumen 513 of the catheter 403 extends to the distal tip of the catheter so that a guide wire can be used to position the catheter at a selected site within the patient's body. The guide wire lumen 513 may include an extension 519 that includes a standard luer 521. The luer 521 permits a valve to be fitted to the guide wire extension 519, thus permitting insertion of the guide wire, drug perfusion, and saline flush of the guide wire lumen 513, while preventing blood from exiting the proximal end of the guide wire lumen 513. Similar to the catheters described above, the seed lumen 509 and fluid return lumen 511 are sealed to each other so that the fluid or gas used to deliver or retrieve the treating elements does not exit the distal end of the catheter into the body of the patient.

Additionally, in order to allow the patient's blood to more easily perfuse past the delivery catheter 403, holes 522 (FIG. 28a) can be drilled from the outside wall of the catheter through to the guide wire lumen 513. The holes 522 create passageways for the blood within the vessel to travel through the guide wire lumen and exit at the distal tip of the catheter. The distal end of the catheter 403 is also tapered from the perfusion holes to the distal tip of the catheter. Once the delivery catheter 403 has been properly placed, the guide wire can be moved back proximal of the perfusion holes 522 so that the guide wire lumen 513 can be unobstructed so as to allow for more blood flow. Alternatively, the delivery catheter 403 could have a separate lumen with holes for perfusion. In either case, the catheter could incorporate a valve (not shown) in the guide wire or perfusion lumen to prevent the blood from flowing back to the proximal end of the catheter.

Radiopaque markers 515, 517, such as those described above, are located at the distal end of the catheter 403 approximately three centimeters apart (depending on the length of the series of treating elements) to assist in proper placement of the catheter and the treating elements used therewith. Suitable inks for producing the radiopaque markers include those manufactured by a Creative Materials, Inc, of Tynsboro, Massachusetts and are identified by the product numbers 114–29, 113–49, and 256–04 c.

As illustrated in FIGS. 27, 28a, the guide wire lumen 513 extends the entire length of the catheter. However, as shown in FIG. 29a, the guide wire lumen 513 can be configured to extend only from the distal tip of the catheter to a location proximal the distal tip to obtain the "rapid exchange" benefits similar to those described in U.S. Pat. No. 4,762,129 issuing to Bonzel. The guide wire lumen 513 preferably extends from the distal tip to a location proximal of the radiopaque marker 515, so that when the guide wire 514 is retracted (so as not to interfere with the radiation emitted from the treating elements) the guide wire 514 still engages the guide wire lumen 513.

Figure 30:
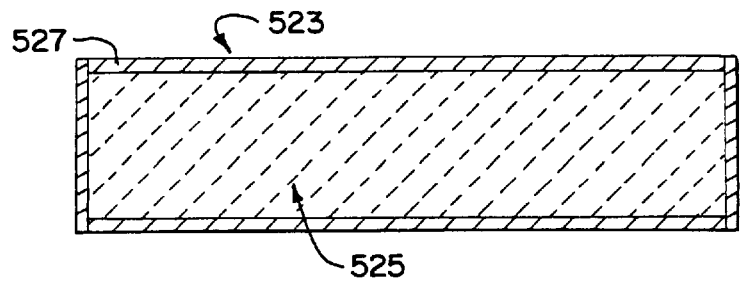
FIG. 30 is a cross-sectional view of a radioactive seed to be used with the delivery system of FIG. 20.

Turning to FIG. 30, there is seen a radioactive treating element 523, which can be used as an alternative to the treating elements 22 described above. The treating elements 523 comprise a radioactive material sintered into a ceramic rod 525, which is then encapsulated in a cylindrical stainless steel capsule 527. In practice, 12 independent, non-connected treating elements 523 are used in a series, with each element being approximately 2.5 mm in length so that the total length of the source train is 3 cm. However, the seed length and the number of seeds may vary so that the total length of the source train is equal to or longer than the length of the lesion to be treated. Preferred radioactive sources include beta-emitting sources such as Strontium-90, Yttrium-90, Ruthenium-106, Thulium-170 and Tungsten-185. Gamma-emitting sources, such as Iridium-192, may also be used. Such radioactive sources are dissolved within a solvent, such as chloride or sodium nitride into which a ceramic rod is dipped. The ceramic rod is then heated so as to sinter the radioactive material into the ceramic. The ceramic rod is then encapsulated within a hollow, stainless steel cylinder, with a cap secured at each end by, e.g., welding, adhesives, or solvent bonds. Sharp edges are removed from the capsule, and a coating can be applied to the exterior surface so as to reduce the frictional coefficient associated with the capsule during delivery through the catheter. The walls of the cylinder may be sufficiently thick to block one type of radiation emitted from a particular radioactive source, while allowing a second type of radiation (a daughter element) to penetrate the cylinder.

Marker seeds 528 (FIGS. 28a, 29a) can be positioned on either side of the radioactive source train to assist in locating and positioning the treating elements. The marker seeds 528 may be made of gold, gold-plated stainless steel, or synthetic ruby, each of which can be seen under fluoroscopy.

Figure 31A:
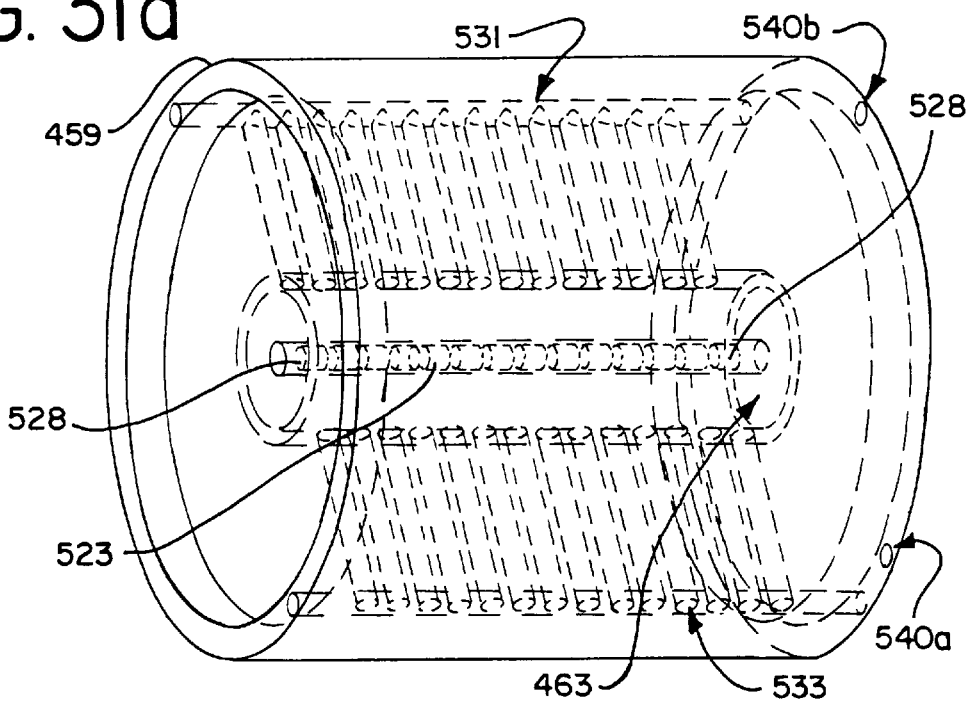
FIGS. 31a and 31b are a perspective view and an exploded perspective view of a fiber optic seed verification system that may be associated with the central housing of the transfer device.
Figure 31B:
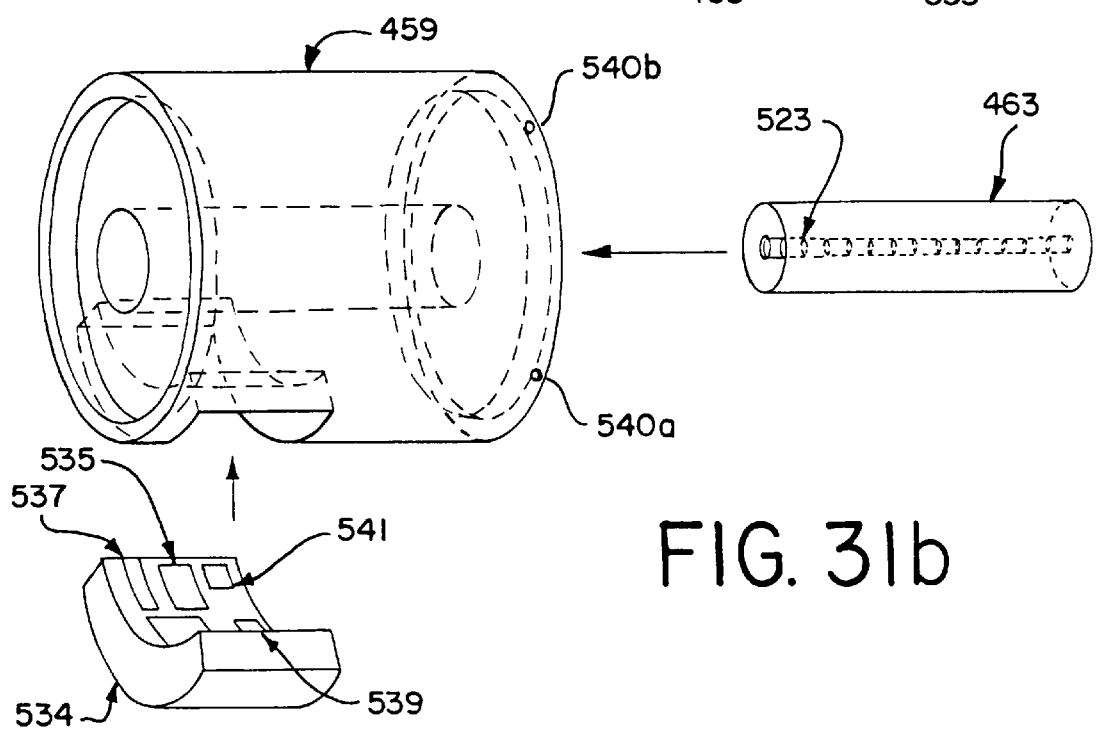
Figure 34:
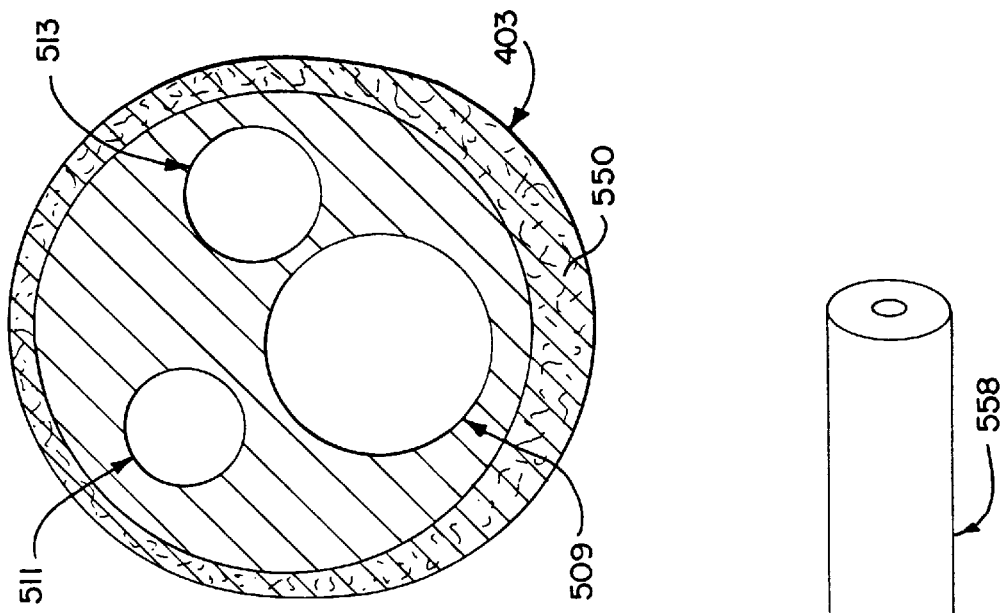
FIG. 34 is a cross sectional view of the distal end of a delivery catheter according to the present invention that has a radiation-blocking coating.

In order to verify the position of the treatment seeds 523 and marker seeds 528, the central housing 459 of the transfer device 401 can optionally include a fiber optic device associated with the central lumen 463a of the quartz sleeve 463. Turning to FIGS. 31a and 31b, there is seen a quartz sleeve 463 in which twelve treating elements or seeds 523 and two marker seeds 528 rest end-to-end. The central housing 459 includes fourteen fiber optic transmission elements 531 and fourteen fiber optic receiver elements 533, (i.e., one pair for each treating element and marker seed comprising the radioactive seed train), which are positioned on diametrically opposite sides of the lumen 463a.

Operatively connected to the fiber optic elements 531, 533 is a modular circuit board 534 (FIG. 31b) that includes a battery 535, a light source 537, an interface unit 539, and a light receiver/logic module 541. The light source 537 produces either a visible or a non-visible light energy which is transmitted via the fiber optic transmitting elements 531. (Alternatively, reflective light energy can be used.) When a radioactive seed 523 is not present in the transfer device between the fiber optic transmission element 531 and its matching receiving element 533, light energy is transmitted across the lumen 563a at that point and received by the receiving element 533, which transmits it to the light receiver/logic module 541. The logic module concludes that a seed is missing from the sleeve 529 and sends an output to the interface unit 539 indicating the same. When all the seeds are present inside the sleeve 529, all light transmissions are blocked. The logic module 541 determines that all seeds are present (since no light was received) and sends an output to the interface unit 539 indicating the same. If each of the fiber optic elements 531, 533 is separately wired to the light receiver/logic module 541, then the number of missing seeds can be determined. The circuit board 534 may include a digital display on its exterior side so that the general absence of seeds, or the number of seeds missing, can be displayed. The interface unit 539 can optionally be replaced with green and red light emitting diodes (LED's) 540a and 540b (FIG. 31a) so that when a seed is not present, the red LED 540a is illuminated, and when all seeds are present, the green LED 540b is illuminated.

In an alternative embodiment, (not illustrated) a single pair of transmitting element 531 and receiving element 533 can be used to verify the position of the radioactive elements 523. The fiber optic pair 531, 533 is positioned just proximal to the distal end of the central housing and counts the number of seeds that have passed by, recording the number of times the light energy is blocked. A micro chip with memory counts the number of seeds which have either entered or exited from the central housing and a logic module reads the number to indicate whether all the seeds have been returned to the transfer device or, alternatively delivered to the catheter. In a further alternative, a timer can be added to ensure that the seeds are properly counted. If the seed length and speed velocity are known, then the time it takes for the seed (or seeds) to pass through transmitting light can be calculated and the logic module can determine how many seeds have passed by the fiber optic pair 531, 533.

Applicants believe that in order to obtain uniform dosage of the radiation from the source train, it may be important to center the radiation source within the walls of the vessel to be treated. If the radiation sources are not centered within the vessel wall, then the radiation dosage may not be uniform (The center of the blood vessel is not necessarily the same as the center of the passage way therethrough. A stenotic vessel has a narrow lumen because of plaque or tissue that has formed along the vesseles interior wall. In many cases, the plaque or tissue is not uniform in size or shape along the vessel wall. Thus, the lumen of the vessel is non-concentric in relation to the vessel wall.)

The radiation source can be passively centered within the vessel wall by using a catheter with a sufficiently large outer diameter in relation to the diameter of the vessel. The difference of the vessel's diameter and the catheter's diameter determines the degree of movement the catheter will be afforded once it is positioned within the vessel. The radiation source can be centered or approximately centered within the vessel wall 542 between the plaque 544 by e.g., the use of at least one concentric or non-concentric compliant balloon 546, (FIGS. 32a, 32b) (i.e., eccentric in relation to the catheter 403). When using a catheter 403 that has a non-concentric seed lumen 509, the seed lumen 509 is closer to one side of the vessel wall 542 and the centering balloon 546 needs to be eccentric even if the vessel lumen is concentric with respect to the vessel wall 542. If the catheter has a concentric seed lumen, a concentric balloon can be used only if the vessel lumen is concentric in relation to the vessel wall. While the balloon 546 is illustrated as extending radially around the entire circumference of the catheter, it could extend radially about a partial circumference of the catheter. If the radiation elements 523 are not centered in the vessel wall, then the catheter 403 may be partially or fully rotated during delivery of the radiation dose so as to not overexpose any one area of the vessel to be treated.

While a variety of balloon shapes could be used, an eccentric coiled balloon 548 (FIGS. 33a, 33b) has the advantage of allowing the patient's blood to perfuse past the catheter 403 and balloon 548. The centering balloon could have a separate inflation lumen, or the existing seed lumen or hydraulic return lumen could be used as the inflation lumen, in which case the seed or hydraulic return lumen must be in fluid communication with the balloon. The centering balloon, in addition, may be used as a dilation balloon and a stent deployment balloon. Alternatively, coatings that at least partially block emitting radiation (FIG. 34) could be applied to the distal end of the catheter. The thickness and location of the coating 550 can be varied about the periphery of the outside wall of the catheter 403 in order to have the vessel wall receive a uniform radiation dose.

The plaque along a treatment site may also not be of uniform composition (i.e. calcified and non-calcified plaque). Thus, it may be desirous to use radioactive seeds 523 with different activity levels depending upon the composition of the plaque in the area of the vessel to be treated. Such a variable radiation profile may also be desirable either before or after the placement or removal of a stent to treat the "end effect" of the stent on the vessel wall (i.e., the formation of intimal hyperplasia within pocketed areas along the vessel wall at the ends of the stent).

Figure 35:
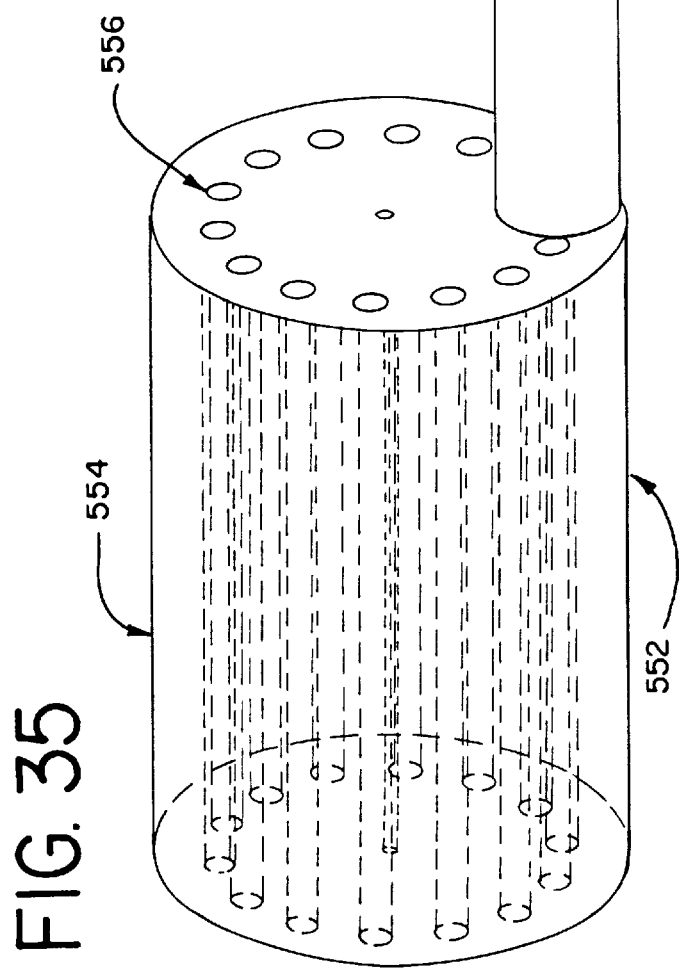
FIG. 35 is a perspective view of a device to permit the user to create a radiation source train in which the activity level of the seeds comprising the source train can be varied.

Turning to FIG. 35, there is seen a dosimetry device 552 that permits the fabrication of radioactive source trains in which the number of seeds and the activity level of the various seeds comprising the radioactive source train is custom selected. Specifically, the dosimetry device 552 comprises a rotatable cylinder 554 having a plurality of storage chambers 556 (14 as illustrated) in which each storage chamber 556 houses a plurality of radiation elements 523 of the same activity. (However, the activity of the elements and/or the radioactive source may differ from chamber to chamber and the elements may include non-active or passive elements.) A storage chamber may also house a plurality of marker seeds. By rotation, the cylinder 554 can be positioned so that the individual chambers 556 can be aligned with a transfer sleeve 558 which includes means for moving the treatment elements from the various chambers 556 into the lumen of a transfer sleeve 558. The customized source train can be manually loaded into the transfer sleeve 558 or can be loaded by an automatic controlling unit, including a microprocessor in which the physician defines the appropriate radiation dosimetry profile and the automatic system assembles the customized train and loads them into the transfer sleeve 558. After the desired source train is fabricated, the transfer sleeve is detached from the dosimetry device 552 and the radioactive source train is loaded into the quartz sleeve 463 of the transfer device 401. Alternatively, the dosimetry device 552 may be integral with the transfer device 401.

The operation of the transfer device 401 of FIGS. 20–25 can be summarized as follows: Initially, the fluid control switch 421 is in the "off" position and the actuator switch 465 is in the "connect/prime" mode. The connector 469 then is inserted into the distal end of the transfer device 401 until it locks into place, as described above. The seed lumens 433, 463a, 505, 509 and the return lumens 431, 471, 507, 511 are primed by positioning the fluid control switch 421 in either the "return" mode or "send" mode, while the actuator switch 465 remains in the "connect/prime" mode. The treating elements 523 can be delivered to and maintained in the distal end of the catheter 403 by positioning the fluid control switch 421 in the "send" position and the actuator switch 465 in the "seed transit" mode.

The treating elements 523 are retrieved and repositioned within the transfer device 401 by positioning the fluid control switch 421 in the "return" position, while the actuator switch 465 remains in the "seed transit" mode. After the treating elements 523 are repositioned within the transfer device 4011, the connector 469 can be disconnected by positioning the fluid control switch 421 in the "off" position and the actuator switch 465 in the spring-loaded "release" mode.

A treatment procedure utilizing the transfer device 401 and delivery catheter 403 of FIGS. 20–34 can be summarized as follows: Prior to radiation treatment, a sterile sleeve is placed over the transfer device 401 (if, for some reason, the transfer device has not been already sterilized) and the operator confirms that the fluid control switch 421 is set to "off" and the actuator switch 465 is set to "connect/prime." The connector 469 is then inserted into the distal end of the transfer device 401.

The fluid control switch 421 is then set to "send" or "return", while the actuator switch 465 remains in the "connect/prime" position. A saline-filled syringe or other fluid (i.e. liquid or gas) supply is then connected to the fluid injection port 423 of the transfer device 401 and positive fluid pressure is applied. As a result, the various channels of the transfer device 401 and the closed lumens of the catheter 403 are primed and flushed with saline. Proper flushing is confirmed by the exit of saline from the fluid exit port 425 of the transfer device 401.

The connector 469 is then disconnected from the transfer device 401 by positioning the fluid control switch 421 in the "off" position and the actuator switch 465 in the "release" position. The transfer device can then be placed in a shielded area for temporary storage until ready for use.

The guide wire lumen 513 of the catheter 403 is then primed and flushed by connecting a saline-filled fluid supply to the guide wire extension fitting 521, 519, and saline is forced through the lumen 513 until it exits at the distal tip of the catheter 403.

The delivery system is now ready for performing a radiation treatment. If the radiation treatment is to follow another procedure, (e.g., balloon or laser angioplasty, drug delivery, stent or shunt placement, coronary artery bypass graft, or atherectomy), any guide wire and/or guiding catheter used for that procedure is left in place while the other catheters are removed. If the guide wire used in the procedure before the radiation treatment is not the proper size for the guide wire lumen 513 of the delivery catheter 403, then a guide wire 514 of the proper size will be exchanged for the one already in place. If the radiation treatment is to precede another procedure, such as those identified above, then an appropriately-sized guide wire and guiding catheter is introduced into the patient's vascular system and advanced until their distal ends reach the treatment site. The delivery catheter 403 is then inserted and advanced through the guiding catheter over the guide wire 514 to the radiation treatment site. Fluoroscopy is used to properly place the delivery catheter 403 at the treatment site and placement of the catheter 403 is verified by aligning the proximal and distal radiopaque markers 515, 517 with the ends of the treatment area. The guide wire 514 is then retracted to just proximal of the treatment site and the proximal radiopaque marker 515 so as to not interfere with the radiation emissions of the treatment elements 523.

The transfer device 401 is then connected to the catheter 403 by means of the connector 469. To do so, the operator confirms that the fluid control switch 421 is in the "off" position and the actuator switch 465 is in "connect/prime" position and the connector 469 is inserted into the distal end of the transfer device 401 to connect the delivery catheter 403 to the transfer device 401, as described above. A liquid or gas supply, such as a saline-filled syringe or gas pump, is connected through the luer lock 423 to the fluid inlet channel 427 of the transfer device 401. A fluid of a higher viscosity than saline may be used to insure that the individual treatment seeds of the source train travel as a group through the seed transit lumen. (A pressure gauge and pressure release valve (not shown) can be embedded in the proximal end of the transfer device 401 to insure that the fluid pressure does not exceed dangerous levels (e.g. more than 100 psi).) The delivery catheter may include an angioplasty balloon at its distal end to perform angioplasty at the treatment site just prior to, during, or just after radiation delivery. A radiation delivery catheter including an angioplasty balloon may have a separate lumen for inflating/deflating the balloon. If so, the operations of the transfer device are unaffected and the balloon is separately inflated either before, during, or after the radiation delivery. Deflation of the balloon may occur at anytime after inflation of the balloon. If there is not a separate inflation lumen, then the balloon must be in fluid communication with either the seed lumen and/or the fluid return lumen so that when the radiation elements are delivered hydraulically/pneumatically, the balloon simultaneously inflates. To deflate the balloon, a negative pressure must be applied to the fluid access port of the transfer device. If the angioplasty is to occur prior to the delivery of the radiation elements or after retrieval of the radiation elements, the actuator switch 465 must be positioned in the "connect/prime" mode to prevent the seeds from being delivered while the balloon is being inflated. If the catheter 403 includes a centering balloon (such as the eccentric centering balloon 546 of FIGS. 32*a*, 32*b* or the coiled centering balloon 548 of FIGS. 33*a*, 33*b*), and there is a fourth lumen for inflation of the centering balloon, then a fluid supply is connected to the inflation lumen and positive fluid pressure is applied to inflate the centering balloon.

If the operator wishes to confirm the operation of the system prior to performing the radiation treatment, the operator may attach a transfer device 401 which contains only non-active or passive seeds to the catheter 403 via the connector 469. The passive seeds are then delivered to and retrieved from the distal end of the catheter 403. If the catheter 403 includes either an angioplasty balloon or a centering balloon, it is not necessary to inflate the balloon when testing the system. If the system is determined to be working properly, the transfer device 401 containing dummy seeds is replaced by one containing radioactive seeds.

The operator is now ready to deliver the radiation elements 523 to the treatment site. To do so, the operator positions the fluid control switch 421 in the "send" mode and the actuator switch 465 to the "seed transit" mode. A shield such as a sterile (lead) drape, may be placed over the extension tubings and the portion of the catheter 403 outside of the patient's body to shield those in the room from radiation exposure when the treatment elements 523 travel from the transfer device 401 to the portion of the catheter 403 inside the patient's body. With pure beta-emitting sources, a plastic drape may be used for shielding purposes. Then, either saline or gas is injected into the fluid injection port 423 of the transfer device 401 to propel the radiation elements 523 to the distal end of the delivery catheter 403. Fluoroscopy and marker seeds are again used to ensure proper placement of the radiation elements 523. If the catheter 403 has a centering balloon but no separate inflation lumen for the balloon, the saline injected into the fluid injection port of the transfer device 401 will also inflate the balloon in addition to delivering the treatment elements 523.

The radiation elements 523 are then maintained at the treatment site for a prescribed amount of time, preferably between 1–10 minutes. This treatment time is calculated prior to the radiation procedure and the radiation elements may be maintained at the treatment site by maintaining a sufficient fluid pressure in the delivery catheter, either manually or by the use of a fluid bag or locking syringe.

If the catheter 403 includes a centering balloon with a separate lumen for inflation, then, once the prescribed dose has been delivered, the fluid control switch 421 is positioned in the "return" mode, a positive fluid pressure is applied, and the treatment elements 523 are returned to the transfer device, as verified by the operator seeing the marker seeds 528 located within the quartz sleeve 463 or, alternatively, as verified by a fiber optic seed verification system 529, as shown in FIG. 31.

A negative fluid pressure is applied to the separate inflation lumen to deflate the centering balloon. If the catheter 403 does not include a separate inflation lumen for the centering balloon, then, once return of all the radiation elements is confirmed, a negative pressure is applied to the fluid injection port 423 so that the balloon will deflate.

After the return of all the radiation elements 523 to the quartz sleeve 463 is confirmed, the fluid control switch 421 is set to the "off" position and the actuator switch 465 is set to the spring-loaded "release" position. The transfer device 401 is then disconnected from the connector 469. The delivery catheter 403 is then withdrawn and post catheterization procedure practices and techniques, or other procedures (e.g. balloon or laser angioplasty, atherectomy, drug delivery, or stent or shunt placement) are performed.

In addition to the vascular system, the distal end of the catheter may be introduced into any one of the intraluminal passageways within the human body to treat that passageway or its surrounding areas. The overall design and function of the apparatus of the present invention remains the same among its various uses within all of the human body's intraluminal passageways. However, the size of the apparatus or the materials from which it is made may be altered so that the maneuverability of the catheter in relation to the applicable lumen may be optimized. Other than the placement of the distal end of the catheter, methods for treating a selected area of the body by delivering treating elements via a catheter to a desired location within an intraluminal passageway of the human body are identical to the method provided for treating a selected area of the vascular system. The catheter is preferably, but not necessarily, inserted over a guide wire and through a guiding catheter.

In treating the biliary tract and its surrounding areas, the distal end of the catheter may be introduced percutaneously into one of the three main biliary ducts, which includes the common bile, common hepatic, and cystic ducts. The cystic duct and the common hepatic duct join to form the common bile duct. Transjugular access to the common bile duct may be an alternative route. The distal end of the catheter enters a hepatic vein via the internal jugular vein in the neck and entry into the common bile duct is achieved through a percutaneous puncture across the wall of the hepatic vein. As a second alternate route, the common bile duct may be accessed through the papilla of Vater, an opening into the lumen of the duodenum. After the catheter is accessed within the biliary tract, it is positioned at the desired location with the biliary tract. Surrounding areas that may be treated include the liver, pancreas, gall bladder, and duodenum.

In treating the pancreas and the pancreatic ducts, the distal end of the catheter is positioned within one of the pancreatic ducts. The pancreatic ducts communicate with the duodenal papilla of the duodenum; thus, the catheter may be positioned within the pancreatic ducts through a percutaneous transduodenal approach.

The distal end of the catheter is inserted into the exterior opening of the urethra and guided to a desired location within the urinary tract to treat urinary structures, such as the kidneys, renal pelvis, ureters, urinary bladder, and urethra. Surrounding areas of the urethra, such as the prostate, may also be treated by introducing the catheter into the urinary tract via the urethra. Alternatively, the prostate may also be treated by a transperineal or transrectal insertion of the catheter.

To treat areas of the female reproductive system, the distal end of the catheter is introduced transvaginally into the female reproductive tract and positioned at a desired location. Although a transvaginal approach is the least invasive, the female reproductive tract may be accessible through a transperineal insertion of the catheter. Such areas of the vagina, uterus, cervix, fallopian tubes, ovaries, and the endometrium may be treated by delivering the treating elements via the catheter to a desired location within the female reproductive tract.

In treating the esophagus, the distal end of the catheter is introduced into the mouth until it touches the posterior wall of the pharynx. The patient is then asked to swallow and the catheter is moved gently onward into the esophageal lumen. The distal end of the catheter is then positioned at the desired location for treatment.

In treating the trachea, bronchi, and lungs, the distal end of the catheter is introduced into the trachea via the nasal cavities. Once in the trachea, the catheter is either positioned at a desired location within the trachea or is further advanced to a desired location within the bronchi of the lungs.

Although the present invention has been described in terms of certain specific embodiments, it is understood that various changes and modifications may be made without departing from the present invention, and reference should be made to the appended claims to determine the proper scope of this invention.

What is claimed is:

1. A catheter for delivering treatment elements to a selected site within the intraluminal passageways of a body in combination with a treatment element, the catheter comprising an elongated tubular member having first, second, and third lumens therein, a proximal end, and a distal end, said first lumen having a diameter sufficiently large between said proximal and distal ends of said tubular member to permit slidable passage of at least one treatment element between said proximal and distal ends, said first and second lumens being in fluid-tight communication with each other at said distal end of said tubular member, the distal end including at least one balloon for centering said distal end of the catheter within the selected site, said balloon being selectively inflatable through one of said lumens, and at least one treatment element comprising a pellet slidably received within said first lumen.

2. The catheter of claim 1 wherein the balloon has an asymmetrical shape.

3. The catheter of claim 1 wherein said balloon is in the form of a spiral.

4. The catheter of claim 1 wherein the distal end includes perforations between the exterior of the catheter and a lumen therein so as to permit perfusion of bodily fluid through the catheter.

5. The catheter of claim 1 wherein the catheter has a cloverleaf-shaped cross section.

6. The catheter of claim 1 wherein said third lumen is sized to receive a guide wire, said third lumen extending along said catheter for a predetermined length at the distal end of said catheter.

7. A catheter for the delivery of radiation-emitting treatment elements to and retrieval from a selected site within the intraluminal passageways of a body, the catheter comprising an elongated tubular member having at least one lumen therein, a proximal end, and a distal end, the distal end having a radiation-blocking coating, said coating being applied so as to selectively block or transmit radiation from the treatment elements through the catheter to the selected site.

8. The catheter of claim 7 wherein the distal end includes perforations between the exterior of the catheter and a through lumen therein so as to permit perfusion of bodily fluid through the catheter.

9. The catheter of claim 7 wherein the catheter has a cloverleaf-shaped cross section.

10. The catheter of claim 7 wherein the catheter includes a lumen for receiving a guide wire, said lumen extending along said catheter for a predetermined length at the distal end of said catheter.

11. A catheter for delivering treatment elements to a selected site within the intraluminal passageways of a body in combination with a treatment element, the catheter comprising:

at least one elongated flexible tube with an outer wall including a proximal end, a distal end for positioning at the selected site within the intraluminal passageway, and defining first, second, and third lumens, said first lumen having a diameter sufficiently large between said proximal and distal ends of said tube to permit slidable passage of at least one treatment element between said proximal and distal ends, said first and second lumens being in fluid-tight communication with each other at said distal end of said tube, said communication being effected through a reinforcing connector, and at least one treatment element comprising a pellet slidably received within said first lumen.

12. The catheter of claim 11 wherein said third lumen is open at said distal end of said tube for receiving a guide wire and includes at least one aperture between the outer wall of said tube and the third lumen to facilitate perfusion of fluids past the catheter.

13. The catheter of claim 11 further comprising at least one longitudinally extending recess along the outer wall of said tube to permit perfusion of fluids past the catheter.

14. The catheter of claim 13 further comprising three longitudinally extending recesses, said tube having a clover leaf-shaped cross section defined by said recesses.

15. The catheter of claim 11 further comprising a connector for attaching said catheter to a transfer device of the type having first and second lumens, said connector for aligning said first and second lumens in said catheter with said first and second lumens of said transfer apparatus.

16. The catheter of claim 15 wherein said connector includes an interfering surface to secure said connector to said transfer device.

17. The catheter of claim 11 wherein said third lumen is open at its distal end and extends between said distal end and a location proximal of said distal end.

18. The catheter of claim 11 further comprising a fourth lumen having at least one aperture therein between said lumen and the outer wall of said tube to permit perfusion of fluid through said catheter.

19. The catheter of claim 11 further comprising at least one radiopaque marker at said distal end of said tube for aligning said distal end and treatment elements with the selected site, and said third lumen is open at said distal end of said tube for receiving a guide wire, said proximal end of said third lumen being proximal to said radiopaque marker.

20. The catheter of claim 11 wherein said tube has an outside diameter sufficiently large with respect to said intraluminal passageway to passively center the treatment elements within the intraluminal passageway.

21. The catheter of claim 15 further comprising a radiation blocking coating at said distal end.

22. A catheter for delivering treatment elements to a selected site within the intraluminal passageways of a body in combination with a treatment element, the catheter comprising:

at least one elongated flexible tube with an outer wall including a proximal end, a distal end for positioning at the selected site within the intraluminal passageway, and defining first, second, and third lumens, said first lumen having a diameter sufficiently large between said proximal and distal ends of said tube to permit slidable passage of least one treatment element between said proximal and distal ends, said first and second lumens being in fluid-tight communication with each other at said distal end of said tube, at least one balloon at said distal end for centering said distal end of the catheter within the selected site, said balloon being selectively inflatable through one of said first, second or third lumens, and at least one treatment element comprising a pellet slidably received within said first lumen.

23. The catheter of claim 22 wherein said balloon has an asymmetrical shape.

24. The catheter of claim 22 wherein said balloon is in the form of a spiral.

25. The catheter of claim 22 wherein said balloon extends radially around a partial circumference of said tube.

26. The catheter of claim 22 wherein said balloon comprises a dilitation balloon.

27. The catheter of claim 22 wherein further comprising a fourth lumen, said fourth lumen being open at said distal end of said tube for receiving a guide wire and including at least one aperture between the outer wall of said tube and said fourth lumen to facilitate perfusion of fluids past the catheter.

28. The catheter of claim 27 wherein said fourth lumen is open at its distal end and extends between said distal end and a location proximal of said distal end.

29. The catheter of claim 22 further comprising at least one longitudinally extending recess along the outer wall of said tube to permit perfusion of fluids past the catheter.

30. The catheter of claim 29 further comprising three longitudinally extending recesses, said tube having a clover leaf-shaped cross section defined by said recesses.

31. The catheter of claim 22 further comprising a connector for attaching said catheter to a transfer device of the type having first and second lumens, said connector for aligning said first and second lumens in said catheter with said first and second lumens of said transfer device.

32. The catheter of claim 31 wherein said connector includes an interfering surface to secure said connector to said transfer device.

33. The catheter of claim 28 further comprising a fourth lumen having at least one aperture therein between said lumen and the outer wall of said plastic tube to permit perfusion of fluid through said catheter.

34. The catheter of claim 22 further comprising at least one radiopaque marker at said distal end of said tube for aligning said distal end with the selected site, and a fourth lumen, said fourth lumen being open at said distal end of said tube for receiving a guide wire, said proximal end of said fourth lumen being proximal to said radiopague marker.

35. A catheter for delivering treatment elements to a selected site within the intraluminal passageways of a body comprising:

least one elongated flexible tube with an outer wall including a proximal end, a distal end for positioning at the selected site within the intraluminal passageway, and defining first, second, and third lumens, said first and second lumens being in fluid-tight communication at said distal end of said tube, said communication being effected through a reinforcing connector, and at least one longitudinally extending recess along the outer wall of said tube to permit perfusion of fluids past the catheter.

36. The catheter of claim 35 further comprising three longitudinally extending recesses, said tube having a clover leaf-shaped cross section defined by said recesses.

* * * * *

UNITED STATES PATENT AND TRADEMARK OFFICE
CERTIFICATE OF CORRECTION

PATENT NO. : 5,899,882
DATED : May 4, 1999
INVENTOR(S) : Ron Waksman; Thomas D. Weldon; Raphael F. Meloul; Richard A. Hillstead; Jonathan J. Rosen; David S. Halpern; Charles E. Larsen It is certified that error appears in the above-indentified patent and that said Letters Patent is hereby corrected as shown below:

On the cover page, in item [75] Inventors, delete "George K. Bonnoitt, Jr., Decatur, GA;"

On the cover page, in item [75] Inventors, delete "Ian R. Crocker, Stone Mountain, GA;"

Signed and Sealed this

Twenty-sixth Day of October, 1999

Attest:

Q. TODD DICKINSON

Attesting Officer

Acting Commissioner of Patents and Trademarks